US012357604B2

(12) United States Patent
Wong et al.

(10) Patent No.: US 12,357,604 B2
(45) Date of Patent: Jul. 15, 2025

(54) TOPICAL FORMULATIONS OF CANNABINOIDS AND USE THEREOF IN THE TREATMENT OF PAIN

(71) Applicant: INMED PHARMACEUTICALS INC., Vancouver (CA)

(72) Inventors: Hayes Wong, North Vancouver (CA); Sazzad Hossain, Richmond (CA); Brian Cairns, Vancouver (CA); Karen Ann Long, Vancouver (CA); Alexandra Mancini, West Vancouver (CA)

(73) Assignee: INMED PHARMACEUTICALS INC., Vancouver (CA)

( * ) Notice: Subject to any disclaimer, the term of this patent is extended or adjusted under 35 U.S.C. 154(b) by 75 days.

(21) Appl. No.: 16/649,119

(22) PCT Filed: Sep. 21, 2018

(86) PCT No.: PCT/CA2018/051194
§ 371 (c)(1),
(2) Date: Mar. 19, 2020

(87) PCT Pub. No.: WO2019/056123
PCT Pub. Date: Mar. 28, 2019

(65) Prior Publication Data
US 2020/0289458 A1 Sep. 17, 2020

Related U.S. Application Data

(60) Provisional application No. 62/562,166, filed on Sep. 22, 2017.

(51) Int. Cl.
| | | |
|---|---|---|
| *A61K 31/352* | (2006.01) | |
| *A61K 31/01* | (2006.01) | |
| *A61K 31/045* | (2006.01) | |
| *A61K 31/05* | (2006.01) | |
| *A61K 31/08* | (2006.01) | |
| *A61K 31/343* | (2006.01) | |
| *A61K 31/397* | (2006.01) | |
| *A61K 31/415* | (2006.01) | |
| *A61K 31/4178* | (2006.01) | |
| *A61K 45/06* | (2006.01) | |
| *A61K 47/24* | (2006.01) | |

(52) U.S. Cl.
CPC .......... *A61K 31/352* (2013.01); *A61K 31/01* (2013.01); *A61K 31/045* (2013.01); *A61K 31/05* (2013.01); *A61K 31/08* (2013.01); *A61K 31/343* (2013.01); *A61K 31/397* (2013.01); *A61K 31/415* (2013.01); *A61K 31/4178* (2013.01); *A61K 45/06* (2013.01); *A61K 47/24* (2013.01)

(58) Field of Classification Search
None
See application file for complete search history.

(56) References Cited

U.S. PATENT DOCUMENTS

| | | |
|---|---|---|
| 6,284,788 B1 | 9/2001 | Mittendorf et al. |
| 6,573,292 B1 | 6/2003 | Nardella |
| 6,825,209 B2 | 11/2004 | Thomas et al. |
| 6,921,722 B2 | 7/2005 | Ogure et al. |
| 7,109,216 B2 | 9/2006 | Kruse et al. |
| 7,294,645 B2 | 11/2007 | Barth et al. |
| 7,314,886 B2 | 1/2008 | Chao et al. |
| 7,446,122 B2 | 11/2008 | Chao et al. |
| 7,504,522 B2 | 3/2009 | Davidson et al. |
| 7,700,634 B2 | 4/2010 | Adam-Worrall et al. |
| 8,778,950 B2 | 7/2014 | Jones et al. |
| 9,133,128 B2 | 9/2015 | Fulp et al. |
| 9,173,867 B2 | 11/2015 | Travis |
| 9,284,303 B2 | 3/2016 | Gijsen et al. |
| 9,376,367 B2 | 6/2016 | Herkenroth et al. |
| 9,394,267 B2 | 7/2016 | Attala et al. |
| 2005/0266061 A1 | 12/2005 | Stinchcomb et al. |
| 2010/0035978 A1* | 2/2010 | Guy ................ A61P 29/02 514/454 |
| 2010/0273895 A1 | 10/2010 | Stinchcomb et al. |
| 2015/0126595 A1 | 5/2015 | Smith |

(Continued)

FOREIGN PATENT DOCUMENTS

| | | | | |
|---|---|---|---|---|
| EP | 1588697 A1 * | 10/2005 | ............. | A61K 47/32 |
| EP | 1645270 B1 | 4/2006 | | |

(Continued)

OTHER PUBLICATIONS

Cumella et al. (ChemMedChem, 7: 452-463, 2012).*
Amaya et al., "Induction of CB1 cannabinoid receptor by inflammation in primary neurons facilitates antihyperalgesic effect of peripheral CB1 agonist", Pain, vol. 124(1-2), pp. 175-183 (2006).
Annoymous, "CBD For Skin Conditions—Cannabidiol Salve, Balms, Creams", buycbdoilonline, Jun. 13, 2014, pp. 1-8; (URL:http://www.buycbdoilonline. Info/2014/06/cbd-skin-conditions), Retrieved from the Internet on Jan. 31, 2019.
Appendino G et al. "Antibacterial cannabinoids from *Cannabis sativa*: a structure-activity study", J Nat Prod., 71:1427-1430 (2008).
Booker et al., "Evaluation of Prevalent Phytocannabinoids in the Acetic Acid Model of Visceral Nociception", Drug Alcohol Depend, vol. 105(1-2), pp. 42-47 (2009).

(Continued)

*Primary Examiner* — Bong-Sook Baek
(74) *Attorney, Agent, or Firm* — Todd Lorenz

(57) ABSTRACT

Pharmaceutical compositions comprising one or more cannabinoids and a pharmaceutically acceptable carrier are disclosed. The compositions are in a form suitable for topical administration, and are useful in the treatment of pain. The cannabinoids suitable for use include cannabidiols, cannabinols, and various other naturally occurring and synthetic cannabinoids. The compositions may also further include anti-inflammatory agents, steroids, or terpenoids. In preferred embodiments, the cannabinoids incorporated in the compositions are cannabidiol (CBD) and cannabinol (CBN) while the carriers are selected from the group consisting of Labrasol™, Transcutol™, lecithin, lysolecithin, isopropyl palmitate, and isopropyl myristate.

7 Claims, 17 Drawing Sheets

(56) References Cited

U.S. PATENT DOCUMENTS

| | | | | |
|---|---|---|---|---|
| 2015/0297556 A1* | 10/2015 | Smith | ............... | A61K 47/08 |
| | | | | 424/449 |
| 2016/0303039 A1* | 10/2016 | Smith | ............... | A61K 9/0014 |
| 2020/0197357 A1* | 6/2020 | Touitou | ............... | A61K 47/24 |

FOREIGN PATENT DOCUMENTS

| | | | | |
|---|---|---|---|---|
| WO | WO 2005/120478 A1 | 12/2005 | | |
| WO | WO 2006/111424 A1 | 10/2006 | | |
| WO | WO-2007001891 A1 * | 1/2007 | ............ | A61K 31/352 |
| WO | WO 2007/148094 A1 | 12/2007 | | |
| WO | WO 2010/013240 A1 | 2/2010 | | |
| WO | WO 2010/126501 A1 | 11/2010 | | |
| WO | WO 2012/160358 A1 | 11/2012 | | |
| WO | WO 2015/068052 A2 | 5/2015 | | |
| WO | WO 2016/090287 A2 | 6/2016 | | |
| WO | WO2016090287 * | 6/2016 | | |
| WO | WO 2017/055846 A1 | 4/2017 | | |
| WO | WO 2017/158539 A1 | 9/2017 | | |
| WO | WO 2017/190249 A1 | 11/2017 | | |

OTHER PUBLICATIONS

Bose et al., "Two Mechanisms Regulate Keratin K15 Expression In Keratinocytes: Role of PKC/AP-1 and FOXM1 Mediated Signalling", PLoS One, vol. 7(6):e38599 (2012).
Boukamp et al., "Normal keratinization in a spontaneously immortalized aneuploidy human keratinocyte cell line", J. of Cell Biology, vol. 106, pp. 761-771 (1988).
Chen et al., "Organ-level quorum sensing directs regeneration in hair stem cell populations", Cell, vol. 161(2), pp. 277-290 (2015).
Coulombe et al., "Epidermolysis bullosa simplex: a paradigm for disorders of tissue fragility", J of Clinical Investigation, vol. 119(7), pp. 1784-1793 (2009).
Cosmetic Bench Reference 1996, Cosmetics & Toiletries, published by Allured Publishing Corporation, pp. 1.19-1.22 (1996).
Dvorak et al., "Histamine induced responses are attenuated by cannabinoid receptor agonist in human skin", Inflamm. Res., vol. 52, pp. 238-245 (2003).
Feng et al., "Antagonism of cannabinoid receptor 2 pathway suppresses IL-6-induced immunoglobulin IgM secretion", BMC Pharmacol Toxicol, 15:30 (2014).
Formukong et al., "Analgesic and Antiinflammatory Activity of Constituents of *Cannabis sativa* L.", Inflammation, vol. 12, pp. 361-371 (1988).
Gaffal et al., "Anti-inflammatory activity of topical THC in DNFB-mediated mouse allergic contact dermatitis independent of CB1 and CB2 receptors", Allergy, 68(8):994-1000 (2013).
Gardner et al., "Autocrine and paracrine regulation of lymphocyte CB2 receptor expression by TGF-beta", Biochem Biophys Res Commun., 290(1):91-6 (2002).
Hatzfeld, M & Franke, WW, "Pair Formation and Promiscuity of Cytokeratins: Formation in Vitro of Heterotypic Complexes and Intermediate-sized Filaments by Homologous and Heterologous Recombinations of Purified Polypeptides", J Cell Biol, vol. 101, pp. 1826-1841 (1985).
Howlett et al., "International Union of Pharmacalogy. XXVII. Classification of Cannabinoid Receptors", Pharmacolgical Reviews, vol. 54, pp. 161-202 (2002).
InMed Pharmaceuticals, "InMed Expands Pipeline with Initiation of Program Targeting Epidermolysis bullosa simples (EBS)", Feb. 3, 2015.
InMed Pharmaceuticals, "InMed provides update on progress of its development program for epidermolysis bullosa", Nov. 4, 2015, retrieved from https://www.inmedpharma.com/news-media/news/2015/inmed-provides-updated-on-progress-of-its-development-program-for-epidermolysis-bullosa/.
Khilnani, G. and Khilnani, A. K., "Inverse Agonism and its therapeutic significance", Indian J. Pharmacol., vol. 43(5), pp. 492-501 (2011).

Kozela E et al., "Cannabinoids decrease the th17 inflammatory autoimmune phenotype", J Neuroimmune Pharmacol., 8(5):1265-76 (2013).
Lettner et al., "MMP-9 and CXCL8/IL-8 Are Potential Therapeutic Targets in Epidermolysis Bullosa Simplex", PLoS One, 8(7):e703 (2013).
Lloyd et al. "The Basal Keratin Network of Stratified Squamous Epithelia: Defining K15 Function in the Absence of K14", J Cell Biol., 129: 1329-1344 (1995).
Lodzki et al., "Canabidiol-transdermal delivery and anti-inflammatory effect in a murine model", Journal of Controlled Release, vol. 93, pp. 377-387 (2003).
Mazzalupo et al., "Role for Keratins 6 and 17 During Wound Closure in Embryonic Mouse Skin", Dev Dyn. 226(2): 356-65 (2003).
Paladini et al., "Onset of re-epithelialization after skin injury correlates with a reorganization of keratin filaments in wound edge keratinocytes: defining a potential role for keratin 16", Journal of cell biology, 132:381-397 (1996)
Paudel et al, "Cannabidiol bioavailability after nasal and transdermal application: effect of permeation enhancers", Drug Development and Industrial Pharmacy, vol. 36, No. 9, pp. 1088-1097 (2010) Perinatology, vol. 44, No. 2, pp. 243-245 (2014).
Perinatology, vol. 44, No. 2, p. 243-245 (2014).
Pini et al., "The role of cannabinoids in inflammatory modulation of allergic respiratory disorders, inflammatory pain and ischemic stroke", Curr Drug Targets, 13(7):984-93 (2012).
Pucci et al., "Epigenetic control of skin differentiation genese by phytocannabinoids", British Journal of Pharmacology, vol. 170, No. 3, pp. 581-591 (2013).
Radoja et al., Thyroid Hormones and Gamma Interferon Specifically Increase K15 Keratin Gene Transcription, Mol Cell Biol:, 24(8): 3168-3179 (2004).
Ramot et al., "A novel control of human keratin expression: cannabinoid receptor 1-mediated signaling down-regulates the expression of keratins K6 and K16 in human keratinocytes in vitro and in situ", Peer J. 19;1:e40 (2013).
Rawal et al., "Effect of cannabidiol on human gingival fibroblast extracellular matrix metabolism: MMP production and activity, and production of fibronectin and transforming growth factor b", J Periodontal Res., 47(3):320-9 (2012).
Richardson et al., "Cannabinoids reduce hyperalgesia and inflammation via interaction with peripheral CB1 receptors", Pain, 75(1):111-9 (1998).
Roth et al., "Cytokines as genetic modifiers in K5−/− mice and in human epidermolysis bullosa simplex", Hum Mutat, 30(5):832-41 (2009).
Rotty and Coulombe, "A wound-induced keratin inhibits Src activity during keratinocyte migration and tissue repair", Journal of Cell Biology, 197:381-389 (2012).
Rueda et al., "The CB1 Cannabinoid Receptor Is Coupled to the Activation of c-Jun N-Terminal Kinase", Mol Pharmacol., 58(4):814-20 (2000).
Ständer et al., "Topical cannabinoid agonists. An effective new possibility for treating chronic pruritus", Hautarzt., 57(9):801-7 (2006).
Stinchcomb et al., "Human skin permeation of Δ8-tetrahydrocannibonal cannabidiol and cannabinol", J. of Pharmacy and Pharmacology, vol. 56, pp. 291-297 (2004).
Soderstrom et al., "Cannabinoids Modulate Neuronal Activity and Cancer by CB1 and CB2 Receptor-Independent Mechanisms", Frontiers in Pharmacology, vol. 8(720), pp. 1-28 (2017).
Teixeira-Clerc et al., "CB1 cannabinoid receptor antagonism: a new strategy for the treatment of liver fibrosis", Nat Med., 12(6):671-6 (2006).
Toth et al., "Endocannabinoids modulate human epidermal keratinocyte proliferation and survival via the sequential engagement of cannabinoid receptor-1 and transient receptor potential vanilloid-1", Journal of Investigational Dermatology, 131: 1095-1104 (2011).
Turner CE and Elsohly MA, "Biological activity of cannabichromene, its homologs and isomers", J Clin Pharmacol., 21(8-9 Suppl):283S-291S (1981).

(56) References Cited

OTHER PUBLICATIONS

Uitto et al., "Progress toward Treatment and Cure of Epidermolysis Bullosa: Summary of the DEBRA International Research Symposium EB2015", Journal of Investigative Dermatology, vol. 136, No. 2, pp. 352-358 (2016).

Wagner et al., "Gene expression analysis of an epidermolysis bullosa simplex Dowling-Meara cell line by subtractive hybridization: recapitulation of cellular differentiation, migration and wound healing", Exp Dermatol., 21(2):111-7 (2011).

Wagner et al., "Imbalance of intermediate filament component keratin 14 contributes to increased stress signalling in epidermolysis bullosa simplex", Exp Dermatol., 22(4):292-4 (2013).

Waseem et al., "Keratin 15 Expression in Stratified Epithelia: Downregulation in Activated Keratinocytes", J Invest Dermatol., 112, 362-369 (1999).

Werner S and Munz B, "Suppression of keratin 15 expression by transforming growth factor beta in vitro and by cutaneous injury in vivo", Exp Cell Res., 254(1):80-90 (2000).

Wong and Coulombe, "Loss of keratin 6 (K6) proteins reveals a function for intermediate filaments during wound repair", J Cell Biol., 163(2): 327-337 (2003).

Wong et al., "Delta-9-tetrahydrocannabinol decreases masticatory muscle sensitization in female rats through peripheral cannabinoid receptor activation", European J. of Pain, vol. 21, pp. 1732-1742 (2017).

Yang et al., "Effect of chronic CB1 cannabinoid receptor antagonism on livers of rats with biliary cirrhosis", Clin Sci (Lond)., 112(10):533-42 (2007).

Yoshimura et al., "Non-Myeloid Cells are Major Contributors to Innate Immune Responses via Production of Monocyte Chemoattractant Protein-1/CCL2", Front Immunol., 4(482):1-6 (2014).

Zhang et al., "FSP1+ fibroblasts promote skin carcinogenesis by maintaining MCP-1-mediated macrophage infiltration and chronic inflammation", Am J. Pathol., 178(1):382-90 (2011).

\* cited by examiner

TOPICAL FORMULATIONS OF CANNABINOIDS AND USE THEREOF IN THE TREATMENT OF PAIN

BACKGROUND OF THE INVENTION

Pain is one of the most complex and difficult to treat conditions for patients and clinicians. Current treatments are complicated by limited efficacy and considerable side effects. Both peripheral and central mechanisms contribute to the development of chronic pain. Peripheral sensitization is the elevated excitability of the pain receptors at the site of injury and is the initiating drive to central sensitization, which is the abnormal amplification of the peripheral input.

New discoveries in cannabinoid pharmacology have renewed hope in cannabinoid-based treatments for chronic pain. For example, conditional knockout of peripheral CB1 receptors in mice demonstrated that cannabinoid-induced analgesia is mediated primarily through peripheral CB1 receptors. However, whether the endocannabinoid system can be recruited to treat specific pain conditions remains unclear. SATIVEX® (GW Pharma Ltd. Wiltshire, UK), is a cannabis-based buccal spray for the relief of muscle spasticity in multiple sclerosis and neuropathic pain. Although it has been shown to be efficacious, it was discontinued by a significant portion of patients in part due to central adverse effects, including psychoactive effects (Moreno Torres et al 2014; Etges et al 2016). Recent studies suggested peripheral application of cannabinoids could be an effective strategy for analgesia without central side effects. However, there remains a need for cannabinoid pharmaceuticals that have increased efficacy in the treatment of pain and reduced or eliminated psychoactive effects.

SUMMARY OF THE INVENTION

The present invention provides a method for treating pain in a subject in need thereof. In one aspect, the method comprises peripheral (e.g., topical) administration of a therapeutically effective quantity of a cannabinoid or a mixture of cannabinoids to a mammalian subject in need thereof, wherein the therapeutically effective quantity is an amount sufficient to reduce or reverse sensitization (e.g., central sensitization or peripheral sensitization). In some embodiments, the pain is muscle pain. In some embodiments, the pain is nerve pain (e.g., peripheral nerve pain). In some embodiments, the pain is neuropathic pain. In some embodiments, the pain is joint pain. In some embodiments, the pain is arthritis-induced joint pain. In any of the foregoing aspects or embodiment, the pain can be chronic pain.

In some embodiments, the therapeutically effective quantity is an amount sufficient to increase a mechanical threshold in peripheral nerve fibers of the area treated by peripheral (e.g., topical) administration, reduce or eliminate hyperalgesia in the area treated by peripheral (e.g., topical) administration, or reduce or eliminate allodynia in the area treated by peripheral (e.g., topical) administration. In some embodiments, the method comprises peripheral (e.g., topical) administration of a therapeutically effective quantity of one or more cannabidiols. In some cases, the method comprises peripheral (e.g., topical) administration of a therapeutically effective quantity of one or more cannabidiols selected from the group consisting of: (i) $\Delta^5$-cannabidiol (2-(6-isopropenyl-3-methyl-5-cyclohexen-1-yl)-5-pentyl-1,3-benzenediol); (ii) $\Delta^4$-cannabidiol (2-(6-isopropenyl-3-methyl-4-cyclohexen-1-yl)-5-pentyl-1,3-benzenediol); (iii) $\Delta^3$-cannabidiol (2-(6-isopropenyl-3-methyl-3-cyclohexen-1-yl)-5-pentyl-1,3-benzenediol); (iv) $\Delta^{3,7}$-cannabidiol (2-(6-isopropenyl-3-methylenecyclohex-1-yl)-5-pentyl-1,3-benzenediol); (v) $\Delta^2$-cannabidiol (2-(6-isopropenyl-3-methyl-2-cyclohexen-1-yl)-5-pentyl-1,3-benzenediol); (vi) $\Delta^1$-cannabidiol (2-(6-isopropenyl-3-methyl-1-cyclohexen-1-yl)-5-pentyl-1,3-benzenediol); and (vii) $\Delta^6$-cannabidiol (2-(6-isopropenyl-3-methyl-6-cyclohexen-1-yl)-5-pentyl-1,3-benzenediol).

In some cases, the method comprises peripherally (e.g., topically) administering a therapeutically effective quantity of $\Delta^2$-cannabidiol. In some cases, the method comprises peripherally (e.g., topically) administering a therapeutically effective quantity of cannabinol. In some cases, the method comprises peripherally (e.g., topically) administering a therapeutically effective quantity of a mixture of cannabinoids, wherein the mixture cannabinoids comprises a mixture of one or more cannabidiols (e.g., $\Delta^2$-cannabidiol) and cannabinol. In some cases, the mixture of cannabinol and one or more cannabidiols has a cannabidiols to cannabinol ratio of from (1:0.1 µM) to (0.1:1 µM). In some cases, the mixture of cannabinol and one or more cannabidiols is cannabidiols:cannabinol (5:1 µM). In some cases, the mixture of cannabinol and one or more cannabidiols is cannabidiols:cannabinol (1:1 µM).

In some embodiments, the method comprises peripherally (e.g., topically) administering a therapeutically effective quantity of a cannabinoid selected from the group consisting of $\Delta^9$-tetrahydrocannabinol ($\Delta^9$-THC), the synthetic cannabinoid HU-210 (6aR,10aR)-9-(hydroxymethyl)-6,6-dimethyl-3-(2-methyloctan-2-yl)-6H,6aH,7H,10H,10aH-benzo[c]isochromen-1-ol), cannabidivarin (CBDV), cannabichromevarin (CBCV), cannabigerol (CBG), cannabigerovarin (CBGV), cannabielsoin (CBE), cannabicyclol (CBL), cannabivarin (CBV), and cannabitriol (CBT). In some embodiments, the method comprises peripherally (e.g., topically) administering a therapeutically effective quantity of a cannabinoid selected from the group consisting of tetrahydrocannibivarin (THCV) and cannabigerol monomethyl ether (CBGM).

In some embodiments, the method comprises peripherally (e.g., topically) administering a therapeutically effective quantity of a cannabinoid selected from the group consisting of cannabichromenic acid (CBCA), $\Delta^1$-tetrahydrocannabinolic acid (THCA); and cannabidiolic acid (CBDA). In some embodiments, the method comprises peripherally (e.g., topically) administering a therapeutically effective quantity of a cannabinoid selected from the group consisting of rimonabant, JWH-018 (naphthalen-1-yl-(1-pentylindol-3-yl)methanone), JWH-073 naphthalen-1-yl-(1-butylindol-3-yl)methanone, CP-55940 (2-[(1R,2R,5R)-5-hydroxy-2-(3-hydroxypropyl) cyclohexyl]-5-(2-methyloctan-2-yl) phenol), dimethylheptylpyran, HU-331 (3-hydroxy-2-[(1R)-6-isopropenyl-3-methyl-cyclohex-2-en-1-yl]-5-pentyl-1,4-benzoquinone), SR144528 (5-(4-chloro-3-methylphenyl)-1-[(4-methylphenyl)methyl]-N-[(1S,2S,4R)-1,3,3-trimethylbicyclo[2.2.1]heptan-2-yl]-1H-pyrazole-3-carboxamide), WIN 55,212-2 ((11R)-2-methyl-11-[(morpholin-4-yl)methyl]-3-(naphthalene-1-carbonyl)-9-oxa-1-azatricyclo[6.3.1.0$^{4,12}$]dodeca-2,4(12),5,7-tetraene), JWH-133 ((6aR,10aR)-3-(1,1-dimethylbutyl)-6a,7,10,10a-tetrahydro-6,6,9-trimethyl-6H-dibenzo[b,d]pyran), levonatradol, and AM-2201 (1-[(5-fluoropentyl)-1H-indol-3-yl]-(naphthalen-1-yl)methanone).

In some embodiments, the method comprises peripherally (e.g., topically) administering a therapeutically effective quantity of a cannabinoid selected from the group consisting of $\Delta^8$-tetrahydrocannabinol ($\Delta^8$-THC), 11-hydroxy-$\Delta^9$-tetrahydrocannabinol, $\Delta^{11}$-tetrahydrocannabinol, and 11-hydroxy-tetracannabinol. In some embodiments, the method comprises peripherally (e.g., topically) administering a therapeutically effective quantity of a cannabinoid of Formula C-I, C-II, C-III, C-IV, C-V, C-VI, C-VII, and/or C-VIII as described herein. In some embodiments, the method comprises peripherally (e.g., topically) administering a therapeutically effective quantity of a cannabinoid carboxylic acid or a salt of a cannabinoid carboxylic acid. In some embodiments, the method comprises peripherally (e.g., topically) administering a therapeutically effective quantity of benzimidazole cannabinoid agonist bearing a substituted heterocyclic group.

In some embodiments, the method comprises peripherally (e.g., topically) administering a therapeutically effective quantity of a pyrazine cannabinoid derivative, such as a pyrazine cannabinoid derivative selected from the group consisting of (1aS,5aS)-2-pyrazin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide and (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide.

In some embodiments, the method comprises peripherally (e.g., topically) administering a therapeutically effective quantity of an indolyl-3-yl cannabinoid analog selected from the group consisting of 7-chloro-3-(5-{[N-ethyl-N-(2-methoxyethyl)amino]methyl}-[1,2,4]-thiadiazol-3-yl)-1-(tetrahydropyran-4-yl)methyl-1H-indole; 7-chloro-3-{5-[(pyrrolidin-1-yl)methyl]-[1,2,4]-thiadiazol-3-yl}-1-(tetrahydropyran-4-yl)methyl-1H-indole; 7-chloro-3-(5-{[N-ethyl-N-(2-hydroxyethyl)amino]methyl}-[1,2,4]-thiadiazol-3-yl)-1-(tetrahydropyran-4-yl)methyl-1H-indole; 7-chloro-3-(4-{[N-(2-hydroxyethyl)-N-isopropylamino]methyl}-[1,3]-thiazol-2-yl)-1-(tetrahydropyran-4-yl)methyl-1H-indole; 7-chloro-3-(4-{[N-ethyl-N-(2-hydroxyethyl)amino]methyl}-[1,3]-thiazol-2-yl)-1-(tetrahydropyran-4-yl)methyl-1H-indole; 7-chloro-3-(4-{[N-(2-methoxyethyl)-N-methylamino]methyl}-[1,3]-thiazol-2-yl)-1-(tetrahydropyran-4-yl)methyl-1H-indole; and 7-chloro-3-{5-[(2,2-dimethyl-pyrrolidin-1-yl)methyl]-[1,2,4]oxadiazol-3-yl}-1-(tetrahydropyran-4-yl)methyl-1H-indole.

In some embodiments, the method comprises peripherally (e.g., topically) administering a therapeutically effective quantity of one or more cannabinoids, wherein each of the one or more cannabinoids is independently selected from the group consisting of classical cannabinoids, endocannabinoids, non-classical cannabinoids, aminoalkylindoles and eicosanoids.

In some embodiments, the method comprises peripherally (e.g., topically) administering a therapeutically effective quantity of one or more cannabinoids, wherein each of the one or more cannabinoids is selective for the CB1 receptor. In some cases, the cannabinoid that is selective for the CB1 receptor is an antagonist of the CB1 receptor. In some cases, the cannabinoid that is selective for the CB1 receptor is a partial agonist of the CB1 receptor. In some cases, the method comprises administering a therapeutically effective quantity of an endocannabinoid selected from the group consisting of anandamide, 2-arachidonoylglycerol, 2-arachidonyl glyceryl ether, N-arachidonoyl dopamine, and virodhamine.

In some embodiments, the method comprises administering a therapeutically effective quantity of an endocannabinoid derivative selected from the group consisting of 7,10,13,16-docosatetraenoylethanolamide, oleamide, stearoylethanolamide, and homo-γ-linolenoylethanolamine. In some embodiments, the therapeutically effective quantity is administered in a pharmaceutical composition, wherein the pharmaceutical composition comprises: (1) a therapeutically effective quantity of the cannabinoid or the mixture of cannabinoids; and (2) at least one pharmaceutically acceptable carrier for peripheral (e.g., topical) administration of the composition.

In some embodiments, the pharmaceutically acceptable carrier is at least one pharmaceutically acceptable carrier selected from the group consisting of Labrasol (caprylocaproyl polyoxyl-8 glycerides), poloxamer 407, lecithin, and isopropyl palmitate. In some embodiments, the pharmaceutically acceptable carrier comprises Labrasol, poloxamer 407, lecithin, and isopropyl palmitate. In some embodiments, the pharmaceutically acceptable carrier comprises 2-(2-ethoxyethoxy)ethanol, poloxamer 407, lecithin, and isopropyl palmitate. In some embodiments, the pharmaceutical composition includes at least one pharmaceutically acceptable excipient.

In some embodiments, the method further comprises the step of administering (e.g., peripherally, centrally or topically) an additional therapeutically active agent selected from the group consisting of a topical anti-inflammatory agent, and a topical steroid to treat the pain. In some cases, central administration is oral or intravenous administration.

In some cases, the method further comprises the step of peripherally (e.g., topically) administering a therapeutically effective quantity of a terpenoid. In some cases, the terpenoid is selected from the group consisting of borneol, carvophyllene, 1,8-cineol, p-cymene, fenchone, α-humulene, kaempferol, limonene, linoleic acid, α-linolenic acid, luteolin, β-myrcene, oleic acid, orientin, α-pinene, phytol, quercetin, selinene, sitosterol, terpinenol-4, N-trans-caffeoyltyramine, N-trans-coumaroyltyramine, N-trans-feruloyltyramine, and vitexin.

In some cases, the cannabinoid or mixture of cannabinoids and the terpenoid are administered in a single pharmaceutical composition. In some cases, the cannabinoid or mixture of cannabinoids and the terpenoid are administered separately.

In some cases, the step of topically administering a therapeutically effective quantity of a terpenoid comprises topically administering a therapeutically effective quantity of borneol or β-myrcene. In some cases, the step of topically administering a therapeutically effective quantity of a terpenoid comprises topically administering a therapeutically effective quantity of borneol and β-myrcene. In some cases, the borneol and β-myrcene are administered simultaneously. In some cases, the borneol and β-myrcene are administered sequentially. In some embodiments, the method provides substantially no psychoactive effect or no psychoactive effect.

In another aspect, the present invention provides a pharmaceutical composition for treating pain, the pharmaceutical composition comprising: (a) a therapeutically effective quantity of a cannabinoid or mixture of cannabinoids, wherein the therapeutically effective quantity of the cannabinoid or mixture of cannabinoids is an amount sufficient to reduce or reverse central or peripheral sensitization, or reduce pain (e.g., peripheral pain), or the combination thereof; and (b) at least one pharmaceutically acceptable carrier for peripheral (e.g., topical) administration of the pharmaceutical composition, wherein the pharmaceutical composition is a peripheral (e.g., topical) formulation for treatment of pain.

In some embodiments, the pain is muscle pain. In some embodiments, the pain is nerve pain (e.g., peripheral nerve pain). In some embodiments, the pain is neuropathic pain. In some embodiments, the pain is joint pain. In some embodiments, the joint pain is arthritis-induced joint pain. In some embodiments, the pain is chronic pain (e.g., chronic muscle pain, neuropathic pain, nerve pain, joint pain, etc.).

In some embodiments, the topical formulation delivers the therapeutically effective quantity in an amount sufficient to reduce pain (e.g., peripheral pain) or reduce or reverse central sensitization in a subject in need thereof over a period of 40 hours (or 4 hours, or 8 hours, or 10 hours, or 12 hours, or 24 hours, or 48 hours, or 72 hours, or 96 hours) in a single application. In some embodiments, the topical formulation maintains a therapeutically effective quantity in the dermis or in the subcutis or in a tissue underlying the subcutis (e.g., muscle or joint tissue proximal to an area of topical application) in an amount sufficient to reduce pain (e.g., peripheral pain) or reduce or reverse central sensitization in a subject in need thereof over a period of 40 hours (or 4 hours, or 8 hours, or 10 hours, or 12 hours, or 24 hours, or 48 hours, or 72 hours, or 96 hours) in a single topical application.

In some cases, the topical formulation delivers the therapeutically effective quantity of the cannabinoid or mixture of cannabinoids through the stratum corneum, epidermis, and/or dermis within 24, 20, 18, 12, 8, 6, 5, 4, 2 hours of topical application, or within 1 hour of topical application. In some cases, the topical formulation delivers the therapeutically effective quantity of the cannabinoid or mixture of cannabinoids into the dermis or the subcutis or a tissue underlying the subcutis (e.g., muscle or joint tissue proximal to an area of topical application) in an amount sufficient to reduce pain (e.g., peripheral pain) or reduce or reverse central sensitization in a subject in need thereof within 24, 20, 18, 12, 8, 6, 5, 4, 2 hours of topical application, or within 1 hour of topical application.

In some embodiments, the therapeutically effective quantity is an amount sufficient to increase a mechanical threshold in peripheral nerve fibers of the area treated by peripheral (e.g., topical) administration, reduce or eliminate hyperalgesia in the area treated by peripheral (e.g., topical) administration, or reduce or eliminate allodynia in the area treated by peripheral (e.g., topical) administration. In some embodiments, the pharmaceutical composition comprises a therapeutically effective quantity of one or more cannabidiols (e.g., $\Delta^2$-cannabidiol).

In some embodiments, the cannabidiols are selected from the group consisting of: (i) $\Delta^5$-cannabidiol (2-(6-isopropenyl-3-methyl-5-cyclohexen-1-yl)-5-pentyl-1,3-benzenediol); (ii) $\Delta^4$-cannabidiol (2-(6-isopropenyl-3-methyl-4-cyclohexen-1-yl)-5-pentyl-1,3-benzenediol); (iii) $\Delta^3$-cannabidiol (2-(6-isopropenyl-3-methyl-3-cyclohexen-1-yl)-5-pentyl-1,3-benzenediol); (iv) $\Delta^{3,7}$-cannabidiol (2-(6-isopropenyl-3-methylenecyclohex-1-yl)-5-pentyl-1,3-benzenediol); (v) $\Delta^2$-cannabidiol (2-(6-isopropenyl-3-methyl-2-cyclohexen-1-yl)-5-pentyl-1,3-benzenediol); (vi) $\Delta^1$-cannabidiol (2-(6-isopropenyl-3-methyl-1-cyclohexen-1-yl)-5-pentyl-1,3-benzenediol); and (vii) $\Delta^6$-cannabidiol (2-(6-isopropenyl-3-methyl-6-cyclohexen-1-yl)-5-pentyl-1,3-benzenediol).

In some embodiments, the composition comprises a therapeutically effective quantity of cannabinol. In some embodiments, the composition comprises a therapeutically effective quantity of a mixture of cannabinoids, wherein the mixture cannabinoids comprises a mixture of one or more cannabidiols and cannabinol. The mixture of cannabinol and one or more cannabidiols has a cannabidiols to cannabinol ratio of from (1:0.1 µM) to (0.1:1 µM). In some embodiments, the mixture of cannabinol and one or more cannabidiols is cannabidiols:cannabinol (5:1 µM). In some embodiments, the mixture of cannabinol and one or more cannabidiols is cannabidiols:cannabinol (1:1 µM).

In some embodiments, the composition comprises a therapeutically effective quantity of a cannabinoid of Formula C-I, C-II, C-IV, C-V, C-VI, C-VII, and/or C-VIII as described herein. In some embodiments, the composition is a peripheral (e.g., topical) formulation containing a therapeutically effective quantity of an indolyl-3-yl cannabinoid analog described herein. In some embodiments, the composition is a peripheral (e.g., topical) formulation containing a therapeutically effective quantity of a pyrazine cannabinoid derivative described herein. In some embodiments, the composition is a peripheral (e.g., topical) formulation containing a therapeutically effective quantity of a benzimidazole cannabinoid agonist bearing a substituted heterocyclic group as described herein.

In some embodiments, the composition is a peripheral (e.g., topical) formulation containing a therapeutically effective quantity of one or more cannabinoids, wherein each of the one or more cannabinoids is independently selected from the group consisting of classical cannabinoids, endocannabinoids, non-classical cannabinoids, aminoalkylindoles and eicosanoids.

In some embodiments, the composition is a peripheral (e.g., topical) formulation containing a therapeutically effective quantity of a CB1 receptor selective cannabinoid. In some embodiments, the cannabinoid that is selective for the CB1 receptor is an antagonist of the CB1 receptor. In some embodiments, the cannabinoid that is selective for the CB1 receptor is a partial agonist of the CB1 receptor. In some embodiments, the composition is a peripheral (e.g., topical) formulation containing a therapeutically effective quantity of an endocannabinoid selected from the group consisting of anandamide, 2-arachidonoylglycerol, 2-arachidonyl glyceryl ether, N-arachidonoyl dopamine, and virodhamine.

In some embodiments, the composition is a peripheral (e.g., topical) formulation containing a therapeutically effective quantity of an endocannabinoid derivative selected from the group consisting of 7,10,13,16-docosatetraenoylethanolamide, oleamide, stearoylethanolamide, and homo-γ-linolenoylethanolamine. In some embodiments, the composition comprises a pharmaceutical carrier elected from the group consisting of Labrasol (caprylocaproyl polyoxyl-8 glycerides), poloxamer 407, lecithin, and isopropyl palmitate. In some embodiments, the composition comprises a pharmaceutical carrier comprising Labrasol, poloxamer 407, lecithin, and isopropyl palmitate. In some embodiments, the composition comprises a pharmaceutical carrier comprising 2-(2-ethoxyethoxy)ethanol, poloxamer 407, lecithin, and isopropyl palmitate.

In some embodiments, the composition comprises an additional therapeutically active agent selected from the group consisting of a topical anti-inflammatory agent, and a topical steroid. In some embodiments, the composition comprises a therapeutically effective quantity of a terpenoid. In some embodiments, the terpenoid is selected from the group consisting of borneol, caryophyllene, 1,8-cineol, p-cymene, fenchone, α-humulene, kaempferol, limonene, linoleic acid, α-linolenic acid, luteolin, β-myrcene, oleic acid, orientin, α-pinene, phytol, quercetin, selinene, sitosterol, terpinenol-4, N-trans-caffeoyltyramine, N-trans-coumaroyltyramine, N-trans-ferruloyltyramine, and vitexin.

In some embodiments, the terpenoid is borneol and/or β-myrcene. In some embodiments, the composition comprises borneol and β-myrcene.

In some embodiments, the pharmaceutical composition comprises a lipophilic phase and a hydrophilic phase. In some embodiments, the pharmaceutical composition comprises a lipophilic phase comprising the lecithin or lysolecithin and isopropyl palmitate or isopropyl myrsistate and a hydrophilic phase comprising the poloxamer. In some embodiments, the pharmaceutical composition comprises a pharmaceutical carrier selected from the group consisting of Labrasol (caprylocaproyl polyoxyl-8 glycerides) or Transcutol (2-(2-ethoxyethoxy)ethanol), a poloxamer, e.g., poloxamer 407, lecithin or lysolecithin, and isopropyl palmitate or isopropyl myristate.

In some embodiments, the hydrophilic phase comprises less than 35% or 30% poloxamer, e.g., less than 35 or 30% poloxamer 407, and/or at least 20% poloxamer, e.g., at least 20% poloxamer 407, preferably 20% poloxamer (e.g., 20% poloxamer 407). In some embodiments, the lipophilic phase comprises a lecithin or lysolecithin to isopropyl palmitate or isopropyl myristate ratio of from 1:1 to 1:6. In some embodiments, the pharmaceutical composition comprises less than about 80% to at least about 50% hydrophilic phase, preferably about 70% or about 65% or 60% hydrophilic phase. In some embodiments, the pharmaceutical composition comprises less than about 40% to greater than about 20% lipophilic phase. In some embodiments, the lipophilic phase comprises isopropyl palmitate or isopropyl mryistate at from about 18% to about 30%, preferably from 18.75% to 26%. In some embodiments, the pharmaceutical composition comprises from about 1 to about 20% Labrosol (caprylocaproyl polyoxyl-8 glycerides), from about 1 to about 10% Labrosol (caprylocaproyl polyoxyl-8 glycerides), from about 2 to about 8% Labrosol (caprylocaproyl polyoxyl-8 glycerides), from about 5 to about 15% Labrosol (caprylocaproyl polyoxyl-8 glycerides), from about 5 to about 10% Labrosol (caprylocaproyl polyoxyl-8 glycerides), or about 10% Labrosol (caprylocaproyl polyoxyl-8 glycerides). In some embodiments, the pharmaceutical composition comprises from about 1 to about 20% Transcutol 2-(2-ethoxyethoxy)ethanol, from about 1 to about 10% Transcutol 2-(2-ethoxyethoxy)ethanol, from about 2 to about 8% Transcutol 2-(2-ethoxyethoxy)ethanol, from about 5 to about 15% Transcutol 2-(2-ethoxyethoxy)ethanol, from about 5 to about 10% Transcutol 2-(2-ethoxyethoxy)ethanol, or about 10% Transcutol 2-(2-ethoxyethoxy)ethanol.

In some embodiments, the pharmaceutical composition comprises amounts of cannabinoid or mixture of cannabinoids that induce no or substantially no psychoactive effect when administered by peripheral (e.g., topical) administration.

In one aspect, the present invention provides a method of making a pharmaceutical composition described herein, a mixture of cannabinoids as described herein, and/or a topical formulation as described herein. In some embodiments, the method comprises admixing a cannabinoid or mixture of cannabinoids with one or more pharmaceutical carriers, excipients, liquid carriers, thickening agents, isotonic agents, wetting solubilizing or emulsifying agents, surfactants, emollients, preservatives, antioxidants, acidifying agents, alkalinizing agents, carrying agents, chelating agents, complexing agents, solvents, suspending and/or viscosity-increasing agents, oils, penetration enhancers, polymers, stiffening agents, proteins, carbohydrates, bulking agents, topical soothing agents, anti-inflammatory agents, anti-bacterial agents, anti-fungal agents, topical steroids, and/or topical antioxidants, terpenoids, and combinations thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Figure 1:
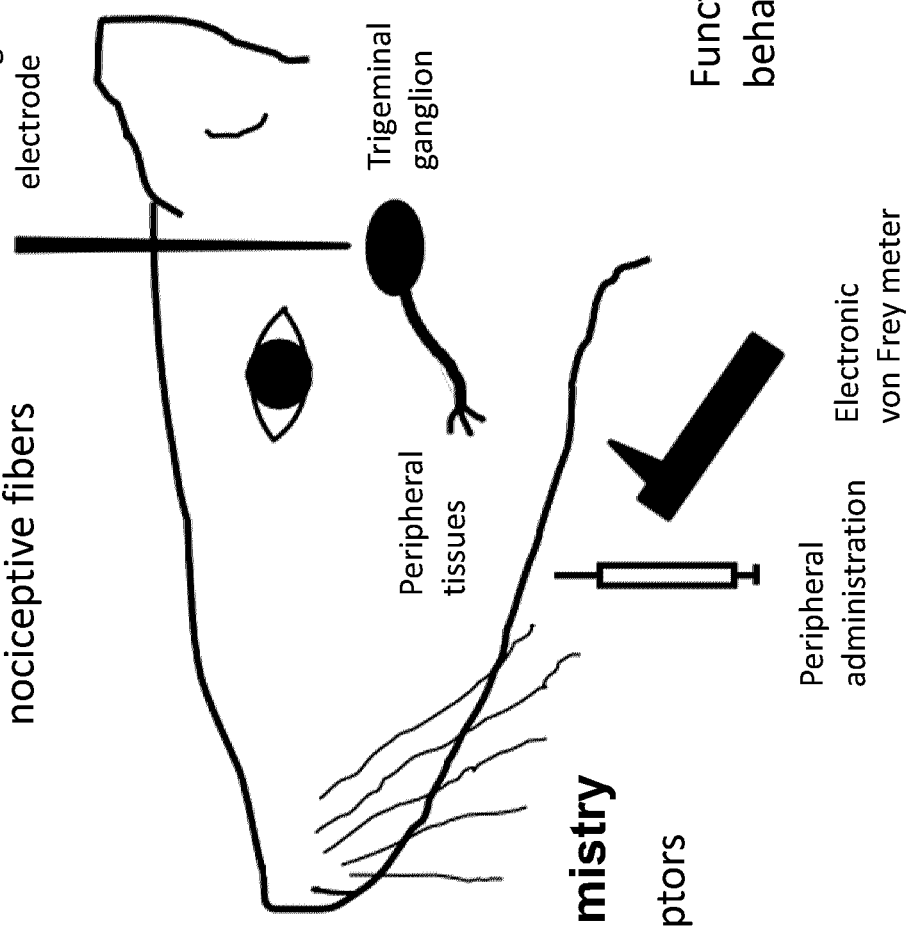
FIG. 1 illustrates an experimental setup for immunohistochemistry to determine cannabinoid (CB) receptor expression in peripheral tissues, electrophysiology to observe the effect of cannabinoids on nociceptive fibers, and measurement of behavioral indications of the effect of cannabinoids on nociceptive fibers.

The present invention provides compositions and methods for the treatment of pain and pain-related conditions, particularly chronic pain. For example, the present invention provides topical pharmaceutical formulations containing a therapeutically effective quantity of a cannabinoid or a mixture of cannabinoids and methods of their use for treatment of pain, chronic pain, peripheral or central sensitization, muscle pain, neuropathic pain, joint pain (e.g., arthritis-induced joint pain), and combinations thereof.

Definitions

As used herein, the terms "therapeutically effective quantity" "therapeutically effective dose" or "therapeutically effective amount" refer to a dose of one or more compositions described herein that produces therapeutic effects for which it is administered, particularly a reduction in pain, or a reduction or complete or partial reversal in peripheral or central sensitization. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

As used herein, the term "allodynia" refers to sensation of pain in response to a stimulus that is normally non-painful.

As used herein, the term "hyperalgesia" refers to an an extreme, exaggerated reaction to a stimulus which is normally painful. "Primary hyperalgesia" refers to pain sensitivity that occurs directly in a site of injury. "Secondary hyperalgesia" refers to pain sensitivity that occurs outside the site of injury, typically in surrounding tissues.

As used herein, the term "peripheral sensitization" refers to a reduction in threshold and an amplification in the responsiveness of nociceptors that occurs when the peripheral terminals of primary sensory neurons are exposed to inflammatory mediators or damaged tissue. Thus, peripheral sensitization is restricted to the site of tissue injury. Primary hyperalgesia is indicative of peripheral sensitization. Accordingly, a reduction or reversal of peripheral sensitization can be detected as a reduction or reversal of primary hyperalgesia.

As used herein, the term "central sensitization" refers to pain hypersensitivity in noninflamed tissue caused by increased pain sensitivity after an initiating cause has disappeared and when no peripheral pathology may be present. Secondary hyperalgesia is indicative of central sensitization. Allodynia can also be indicative of central sensitization. Accordingly, a reduction or reversal of central sensitization can be detected as a reduction or reversal of allodynia or secondary hyperalgesia by either behavioral or electrophysiological methods.

As used herein, the terms "treating," "treatment," and similar terminology refer to any detectable improvement, whether subjective or objective, in the pathology caused by or associated with the indicated disease or condition, e.g., pain. For example, the terms "treating," "treatment," and similar terminology can refer to a decrease in pain, a decrease in central sensitization, or a decrease in peripheral sensitization. For purposes of this invention, beneficial or desired clinical results include, but are not limited to, alleviation of symptoms of pain or sensitization, diminishment of extent of pain or sensitization, stabilized (i.e., not worsening) degree of pain or sensitization, delay or slowing of progression of pain or sensitization, amelioration or palliation of pain or sensitization, and remission (whether partial or total), whether detectable or undetectable. The results of treatment can be determined by methods known in the art. The terms "treating," "treatment," and similar terminology do not imply a cure for the disease or condition to be treated. For the purposes of the present application, treatment can be monitored by observing one or more of the improving symptoms associated with the disease, disorder, or condition being treated, or by observing one or more of the improving clinical parameters associated with the disease, disorder, or condition being treated, as described above.

As used herein, the term "mammalian subject" in the context of a subject in need of pain treatment refers to any animal susceptible to pain, including avians and mammals Mammalian subjects include humans, non-human primates, agricultural mammals (e.g., bovines, equines, ovines, avians, porcines, etc.), domestic or companion mammals (e.g., canines, felines, etc.) and laboratory animals (e.g., rabbits, rats, mice, hamsters, etc.). Treatable avian subjects include chickens, ducks, geese, turkeys, etc. In some cases, the subject is female. In other cases, the subject is male. In yet other cases, the methods and compositions are useful for treating female and male subjects in need thereof.

As used herein, the term "peripheral administration" refers to administration that contacts an active ingredient (e.g., cannabinoid or mixture of cannabinoids such as a mixture of CBD and CBN) with a peripheral never fiber and does not contact the active ingredient with the central nervous system (e.g., a central neuron), or does not contact the active ingredient with the central nervous system to a degree sufficient to cause a psychoactive effect. In an exemplary embodiment, peripheral administration refers to topical administration to skin (e.g., topical administration to deliver one or more active ingredients to a peripheral nerve ending in the skin). In some cases, the peripheral administration refers to subcutaneous, intradermal, or intramuscular administration (e.g., injection). Typically, the peripheral administration is formulated with a pharmaceutically acceptable excipient. In some cases, the peripheral administration is performed with the active ingredient formulated with one or more penetration-enhancing agents. Peripheral administration is generally performed at or proximal to the site of pain and/or sensitization. In some cases peripheral administration is performed using a route of administration and/or a formulation that does not promote or allow delivery across the blood brain barrier.

A topical formulation refers to a pharmaceutical formulation suitable for topical administration. Exemplary embodiments include a cream or an aqueous or non-aqueous liquid formulation. Similarly, a peripheral formulation refers to a pharmaceutical formulation suitable for peripheral (e.g., topical) administration.

Unless otherwise indicated, all cannabinoids, and mixtures thereof are free of, or substantially (>99.9%) free of psychoactive cannabinoids. In another embodiment, all cannabinoids, and mixtures thereof contain an amount of psychoactive cannabinoids that is below an amount that provides a discernible psychoactive effect when administered to a subject, or when administered to a subject at a therapeutic dose, or when peripherally (e.g., topically) administered to a subject (e.g., at a therapeutically effective dose). The psychoactivity of a cannabinoid containing composition or a composition containing a mixture of cannabinoids can be readily ascertained in a rodent model. For example, an inverted screen test can be used to identify cannabinoids and mixtures thereof that are not psychoactive. Alternatively, psychoactivity can be assayed in a dose-escalation experiment in humans.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

As used herein, the term "lower alkyl" or equivalent terminology, without further limitation, refers to $C_1$-$C_6$ groups and, e.g., includes methyl. The term "lower alkyl" can be further limited, such as "$C_2$-$C_6$ lower alkyl," which excludes methyl. The term "lower alkyl", unless further limited, refers to both straight-chain and branched alkyl groups. These lower alkyl groups can be unsubstituted or substituted, as described below.

"Alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of —$(CH_2)_n$—, where n is 1, 2, 3, 4, 5 or 6. Representative alkylene groups include, but are not limited to, methylene, ethylene, propylene, isopropylene, butylene, isobutylene, sec-butylene, pentylene and hexylene. Alkylene groups can be substituted or unsubstituted.

"Alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted.

"Alkenylene" refers to an alkenyl group, as defined above, linking at least two other groups, i.e., a divalent hydrocarbon radical. The two moieties linked to the alkenylene can be linked to the same atom or different atoms of the alkenylene. Alkenylene groups include, but are not limited to, ethenylene, propenylene, isopropenylene, butenylene, isobutenylene, sec-butenylene, pentenylene and hexenylene. Alkenylen groups can be substituted or unsubstituted.

"Alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be substituted or unsubstituted.

"Alkynylene" refers to an alkynyl group, as defined above, linking at least two other groups, i.e., a divalent hydrocarbon radical. The two moieties linked to the alkynylene can be linked to the same atom or different atoms of the alkynylene. Alkynylene groups include, but are not limited to, ethynylene, propynylene, isopropynylene, butynylene, sec-butynylene, pentynylene and hexynylene. Alkynylene groups can be substituted or unsubstituted.

"Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted. The term "lower alkoxy" refers to an alkoxy group in which the alkyl portion of the alkoxy group is $C_1$-$C_6$.

"Alkylhydroxy" refers to an alkyl group, as defined above, where at least one of the hydrogen atoms is replaced with a hydroxy group. As for the alkyl group, alkylhydroxy groups can have any suitable number of carbon atoms, such as $C_{1-6}$. Exemplary alkylhydroxy groups include, but are not limited to, hydroxy-methyl, hydroxyethyl (where the hydroxy is in the 1- or 2-position), hydroxypropyl (where the hydroxy is in the 1-, 2- or 3-position), hydroxybutyl (where the hydroxy is in the 1-, 2-, 3- or 4-position), hydroxypentyl (where the hydroxy is in the 1-, 2-, 3-, 4- or 5-position), hydroxyhexyl (where the hydroxy is in the 1-, 2-, 3-, 4-, 5- or 6-position), 1,2-dihydroxyethyl, and the like.

"Heteroalkyl" refers to an alkyl group of any suitable length and having from 1 to 3 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heteroalkyl can include ethers, thioethers and alkyl-amines. The heteroatom portion of the heteroalkyl can replace a hydrogen of the alkyl group to form a hydroxy, thio or amino group. Alternatively, the heteroatom portion can be the connecting atom, or be inserted between two carbon atoms.

"Heteroalkylene" refers to a heteroalkyl group, as defined above, linking at least two other groups. The two moieties linked to the heteroalkylene can be linked to the same atom or different atoms of the heteroalkylene.

"Halogen," "halo group," and the like refers to fluorine, chlorine, bromine and iodine.

"Haloalkyl" refers to alkyl, as defined above, where some or all of the hydrogen atoms are replaced with halogen atoms. As for alkyl group, haloalkyl groups can have any suitable number of carbon atoms, such as $C_{1-6}$. For example, haloalkyl includes trifluoromethyl, flouromethyl, etc. In some instances, the term "perfluoro" can be used to define a compound or radical where all the hydrogens are replaced with fluorine. For example, perfluoromethyl refers to 1,1,1-trifluoromethyl.

"Haloalkoxy" refers to an alkoxy group where some or all of the hydrogen atoms are substituted with halogen atoms. As for an alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_6$-8, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantine. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted.

"Cycloalkylene" refers to a cycloalkyl group having the number of carbon atoms indicated, and linking at least two other groups, i.e., a divalent radical. The two moieties linked to the cycloalkylene can be linked to the same atom or different atoms of the cycloalkylene group. Examples of cycloalkylene rings include cyclopropylene, cyclobutylene, cyclopentylene and cyclohexylene, among others. Cycloalkylene groups can be linked 1,1, 1,2, 1,3, or 1,4. The cyclohexylene ring, for example, can adopt a number of conformations, including the boat and chair conformations. The chair conformation of cyclohexylene can have substituents in an axial or equatorial orientation. The divalent nature of the cycloalkylenes results in cis and trans formations where cis refers to both substituents being on the same side (top or bottom) of the cycloalkylene ring, and where trans refers to the substituents being on on opposite sides of the cycloalkylene ring. For example, cis-1,2- and cis-1,4-cyclohexylene can have one substituent in the axial orientation and the other substituent in the equatorial orientation, while trans-1,2- and trans-1,4-cyclohexylene have both substituents in the axial or equatorial orientation. cis-1,3-cyclohexylene have both substituents in the axial or equatorial orientation, and trans-1,3-cyclohexylene can have one substituent in the axial orientation and the other substituent in the equatorial orientation. Cycloalkylene groups can be substituted or unsubstituted.

"Heterocycloalkyl" refers to a saturated ring system having from 3 to 12 ring members and from 1 to 4 heteroatoms of N, O and S. Additional heteroatoms can also be useful, including, but not limited to, B, Al, Si and P. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be unsubstituted or substituted. For example, heterocycloalkyl groups can be substituted with $C_{1-6}$ alkyl or oxo (=O), among many others.

The heterocycloalkyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxzoalidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Heterocyclalkylene" refers to a heterocyclalkyl group, as defined above, linking at least two other groups. The two moieties linked to the heterocyclalkylene can be linked to the same atom or different atoms of the heterocyclalkylene. Heterocycloalkylene groups can be substituted or unsubstituted.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

"Heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can also be oxidized, such as, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10,3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

"Heteroarylene" refers to a heteroaryl group, as defined above, linking at least two other groups. The two moieties linked to the heteroaryl are linked to different atoms of the heteroaryl. Heteroarylene groups can be substituted or unsubstituted.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S.

"Amine" or "amino" refers to an —N(R)$_2$ group where the R groups can be hydrogen, alkyl, alkenyl, alkynyl, cycloalkyl, heterocycloalkyl, aryl, or heteroaryl, among others. The R groups can be the same or different. The amino groups can be primary (each R is hydrogen), secondary (one R is hydrogen) or tertiary (each R is other than hydrogen).

"Alkyl amine" refers to an alkyl group as defined within, having one or more amino groups. The amino groups can be primary, secondary or tertiary. The alkyl amine can be further substituted with a hydroxy group to form an aminohydroxy group. Alkyl amines useful in the present invention include, but are not limited to, ethyl amine, propyl amine, isopropyl amine, ethylene diamine and ethanolamine. The amino group can link the alkyl amine to the point of attachment with the rest of the compound, be at the omega position of the alkyl group, or link together at least two carbon atoms of the alkyl group. One of skill in the art will appreciate that other alkyl amines are useful in the present invention.

"Carboxy" refers to a carboxylic acid group of the formula —C(O)OH or —CO$_2$H. "Carboxyalkyl" refers to a carboxy group linked to an alkyl, as described above, and generally having the formula —C$_{1-8}$ alkyl-C(O)OH. Any suitable alkyl chain is useful.

As used herein, the term "sulfo" refers to a sulfonic acid (—SO$_3$H) substituent. As used herein, the term "sulfamoyl" refers to a substituent with the structure —S(O$_2$)NH$_2$, wherein the nitrogen of the NH$_2$ portion of the group can be optionally substituted as described herein. As used herein, the term "carbamyl" refers to a group of the structure —C(O$_2$)NH$_2$, wherein the nitrogen of the NH$_2$ portion of the group can be optionally substituted as described herein. As used herein, the terms "monoalkylaminoalkyl" and "dialkylaminoalkyl" refer to groups of the structure -Alk$_1$-NH-Alk$_2$ and -Alk$_1$-N(Alk$_2$)(Alk$_3$), wherein Alk$_1$, Alk$_2$, and Alk$_3$ refer to alkyl groups as described herein.

As used herein, the term "alkylsulfonyl" refers to a group of the structure —S(O)$_2$-Alk wherein Alk refers to an alkyl group as described herein. The terms "alkenylsulfonyl" and "alkynylsulfonyl" refer analogously to sulfonyl groups covalently bound to alkenyl and alkynyl groups, respectively. The term "arylsulfonyl" refers to a group of the structure —S(O)$_2$—Ar wherein Ar refers to an aryl group as described herein. The term "aryloxyalkylsulfonyl" refers to a group of the structure —S(O)$_2$-Alk-O-Ar, where Alk is an alkyl group as described herein and Ar is an aryl group as described herein. The term "arylalkylsulfonyl" refers to a group of the structure —S(O)$_2$-AlkAr, where Alk is an alkyl group as described herein and Ar is an aryl group as described herein.

As used herein, the term "alkyloxycarbonyl" refers to an ester substituent including an alkyl group wherein the carbonyl carbon is the point of attachment to the molecule. An example is ethoxycarbonyl, which is CH$_3$CH$_2$OC(O)—. Similarly, the terms "alkenyloxycarbonyl," "alkynyloxycarbonyl," and "cycloalkylcarbonyl" refer to similar ester substituents including an alkenyl group, alkenyl group, or cycloalkyl group respectively. Similarly, the term "aryloxycarbonyl" refers to an ester substituent including an aryl group wherein the carbonyl carbon is the point of attachment to the molecule. Similarly, the term "aryloxyalkylcarbonyl" refers to an ester substituent including an alkyl group wherein the alkyl group is itself substituted by an aryloxy group.

Other combinations of substituents are known in the art and, are described, for example, in U.S. Pat. No. 8,344,162 to Jung et al. For example, the term "thiocarbonyl" and combinations of substituents including "thiocarbonyl" include a carbonyl group in which a double-bonded sulfur replaces the normal double-bonded oxygen in the group. The term "alkylidene" and similar terminology refer to an alkyl group, alkenyl group, alkynyl group, or cycloalkyl group, as specified, that has two hydrogen atoms removed from a single carbon atom so that the group is double-bonded to the remainder of the structure.

As used herein, the term "heteroatom" refers to any atom that is not carbon or hydrogen, such as nitrogen, oxygen or sulfur. When it is part of the backbone or skeleton of a chain or ring, a heteroatom must be at least divalent, and will typically be selected from N, O, P, and S.

The groups defined above, such as those present in the cannabinoid and/or terpenoid compounds described below, can optionally be substituted by any suitable number and type of substituents. Representative substituents include, but are not limited to, halogen, haloalkyl, haloalkoxy, —OR', =O, —OC(O)R', —(O)R', —O$_2$R', —ONR'R",—OC(O)NR'R", =NR', =N—OR', —NR'R", —NR"C(O)R', —NR'—(O)NR"R'", —NR"C(O)OR', —NH—(NH$_2$)=NH, —NR'C(NH$_2$)=NH, —NH—(NH$_2$)=NR', —SR', —S(O)R', —S(O)$_2$R', —S(O)$_2$NR'R", —NR'S(O)$_2$R", —N$_3$ and —NO$_2$. R', R" and R'" each independently refer to hydrogen, unsubstituted alkyl, such as unsubstituted C$_{1-6}$ alkyl. Alternatively, R' and R", or R" and R'", when attached to the same nitrogen, are combined with the nitrogen to which they are attached to form a heterocycloalkyl or heteroaryl ring, as defined above. This cannot be taken to limit the possibility of further optional substituents. Further descriptions of potential additional optional substituents are provided below. Optional substituents typically do not substantially decrease the activity of the compound or the stability of the compound in which they are present, particularly the activity or stability of the compound when present in a pharmaceutical composition as described herein. In some cases, optional substituents increase activity, stability, solubility, and/or bioavailability of the compound when present in a pharmaceutical composition as described herein The compounds described herein may contain one or more chiral centers and/or double bonds and therefore, may exist as stereoisomers, such as double-bond isomers (i.e., geometric isomers such as E and Z), enantiomers or diastereomers. The invention includes each of the isolated stereoisomeric forms (such as the enantiomerically pure isomers, the E and Z isomers, and other alternatives for stereoisomers) as well as mixtures of stereoisomers in varying degrees of chiral purity or percentage of E and Z, including racemic mixtures, mixtures of diastereomers, and mixtures of E and Z isomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The invention includes each of the isolated stereoisomeric forms as well as mixtures of stereoisomers in varying degrees of chiral purity, including racemic mixtures. It also encompasses the various diastereomers. Other structures may appear to depict a specific isomer, but that is merely for convenience, and is not intended to limit the invention to the depicted isomer. When the chemical name does not specify the isomeric form of the compound, it denotes any one of the possible isomeric forms or mixtures of those isomeric forms of the compound. The compounds may also exist in several tautomeric forms, and the depiction herein of one tautomer is for convenience only, and is also understood to encompass other tautomers of the form shown. Accordingly, the chemical structures depicted herein encompass all possible tautomeric forms of the illustrated compounds. The term "tautomer" as used herein refers to isomers that change into one another with great ease so that they can exist together in equilibrium; the equilibrium may strongly favor one of the tautomers, depending on stability considerations. For example, ketone and enol are two tautomeric forms of one compound.

"Salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, PA, 1985, which is incorporated herein by reference.

As used herein, the term "solvate" means a compound formed by solvation (the combination of solvent molecules with molecules or ions of the solute), or an aggregate that consists of a solute ion or molecule, i.e., a compound of the invention, with one or more solvent molecules. When water is the solvent, the corresponding solvate is "hydrate." Examples of hydrate include, but are not limited to, hemihydrate, monohydrate, dihydrate, trihydrate, hexahydrate, and other water-containing species. It should be understood by one of ordinary skill in the art that the pharmaceutically acceptable salt, and/or prodrug of the present compound may also exist in a solvate form. The solvate is typically formed via hydration which is either part of the preparation of the present compound or through natural absorption of moisture by the anhydrous compound of the present invention. In general, all physical forms are intended to be within the scope of the present invention.

Thus, when a therapeutically active agent used in a method according to the present invention or included in a composition according to the present invention, such as, but not limited to, a cannabinoid or a terpenoid, possesses a sufficiently acidic, a sufficiently basic, or both a sufficiently acidic and a sufficiently basic functional group, these group or groups can accordingly react with any of a number of inorganic or organic bases, and inorganic and organic acids, to form a pharmaceutically acceptable salt. Exemplary pharmaceutically acceptable salts include those salts prepared by reaction of the pharmacologically active compound with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, β-hydroxybutyrates, glycolates, tartrates, methane-sulfonates, propanesulfonates, naphthalene-1-sulfonates, naphthalene-2-sulfonates, and mandelates. If the pharmacologically active compound has one or more basic functional groups, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the pharmacologically active compound has one or more acidic functional groups, the desired pharmaceutically acceptable salt may be prepared by any suitable method available in the art, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

"Composition" as used herein is intended to encompass a product comprising the specified ingredients in the specified amounts, as well as any product that results from combination of the specified ingredients in the specified amounts. By "pharmaceutically acceptable" it is meant the carrier, diluent or excipient must be compatible with the other ingredients of the formulation and deleterious to the recipient thereof.

"Pharmaceutically acceptable excipient" refers to a substance that aids the administration of an active agent to and absorption by a subject. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention.

In some cases, protecting groups can be included in compounds used in methods according to the present invention or in compositions according to the present invention. The use of such a protecting group is to prevent subsequent hydrolysis or other reactions that can occur in vivo and can degrade the compound. Groups that can be protected include alcohols, amines, carbonyls, carboxylic acids, phosphates, and terminal alkynes. Protecting groups useful for protecting alcohols include, but are not limited to, acetyl, benzoyl, benzyl, β-methoxyethoxyethyl ether, dimethoxytrityl, methoxymethyl ether, methoxytrityl, p-methoxybenzyl ether, methylthiomethyl ether, pivaloyl, tetrahydropyranyl, tetrahydrofuran, trityl, silyl ether, methyl ether, and ethoxyethyl ether. Protecting groups useful for protecting amines include carbobenzyloxy, p-methoxybenzylcarbonyl, t-butyloxycarbonyl, 9-fluorenylmethyloxycarbonyl, acetyl, benzoyl, benzyl, carbamate, p-methoxybenzyl, 3,4-dimethoxybenzyl, p-methoxyphenyl, tosyl, trichloroethyl chloroformate, and sulfonamide Protecting groups useful for protecting carbonyls include acetals, ketals, acylals, and dithianes. Protecting groups useful for protecting carboxylic acids include methyl esters, benzyl esters, t-butyl esters, esters of 2,6-disubstituted phenols, silyl esters, orthoesters, and oxazoline. Protecting groups useful for protecting phosphate groups include 2-cyanoethyl and methyl. Protecting groups useful for protecting terminal alkynes include propargyl alcohols and silyl groups. Other protecting groups are known in the art.

As used herein, the term "prodrug" refers to a precursor compound that, following administration, releases the biologically active compound in vivo via some chemical or physiological process (e.g., a prodrug on reaching physiological pH or through enzyme action is converted to the biologically active compound). A prodrug itself may either lack or possess the desired biological activity. Thus, the term "prodrug" refers to a precursor of a biologically active compound that is pharmaceutically acceptable. n certain cases, a prodrug has improved physical and/or delivery properties over a parent compound from which the prodrug has been derived. The prodrug often offers advantages of solubility, tissue compatibility, or delayed release in a mammalian organism (H. Bundgard, *Design of Prodrugs* (Elsevier, Amsterdam, 1988), pp. 7-9, 21-24). A discussion of prodrugs is provided in T. Higuchi et al., "Pro-Drugs as Novel Delivery Systems," *ACS Symposium Series*, Vol. 14 and in E. B. Roche, ed., *Bioreversible Carriers in Drug Design* (American Pharmaceutical Association & Pergamon Press, 1987). Exemplary advantages of a prodrug can include, but are not limited to, its physical properties, such as enhanced drug stability for long-term storage.

The term "prodrug" is also meant to include any covalently bonded carriers which release the active compound in vivo when the prodrug is administered to a subject. Prodrugs of a therapeutically active compound, as described herein, can be prepared by modifying one or more functional groups present in the therapeutically active compound, including cannabinoids, terpenoids, and other therapeutically active compounds used in methods according to the present invention or included in compositions according to the present invention, in such a way that the modifications are cleaved, either in routine manipulation or in vivo, to yield the parent therapeutically active compound. Prodrugs include compounds wherein a hydroxy, amino, or mercapto group is covalently bonded to any group that, when the prodrug of the active compound is administered to a subject, cleaves to form a free hydroxy, free amino, or free mercapto group, respectively. Examples of prodrugs include, but are not limited to, formate or benzoate derivatives of an alcohol or acetamide, formamide or benzamide derivatives of a therapeutically active agent possessing an amine functional group available for reaction, and the like.

For example, if a therapeutically active agent or a pharmaceutically acceptable form of a therapeutically active agent contains a carboxylic acid functional group, a prodrug can comprise an ester formed by the replacement of the hydrogen atom of the carboxylic acid group with a group such as $C_{1-8}$ alkyl, $C_{2-12}$ alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N($C_1$-$C_2$)alkylamino($C_2$-$C_3$)alkyl (such as (3-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino-, or morpholino($C_2$-$C_3$)alkyl.

Similarly, if a disclosed compound or a pharmaceutically acceptable form of the compound contains an alcohol functional group, a prodrug can be formed by the replacement of the hydrogen atom of the alcohol group with a group such as ($C_1$-$C_6$)alkanoyloxymethyl, 1-(($C_1$-$C_6$))alkanoyloxy) ethyl, 1-methyl-1-(($C_1$-$C_6$)alkanoyloxy)ethyl ($C_1$-$C_6$) alkoxycarbonyloxymethyl, N($C_1$-$C_6$)alkoxycarbonylaminomethyl, succinoyl, ($C_1$-$C_6$)alkanoyl, α-amino($C_1$-$C_4$) alkanoyl, arylacyl and α-aminoacyl, or α-aminoacyl-α-aminoacyl, where each α-aminoacyl group is independently selected from the naturally occurring L-amino acids, P(O) (OH)$_2$, P(O)(O($C_1$-$C_6$)alkyl)$_2$ or glycosyl (the radical resulting from the removal of a hydroxyl group of the hemiacetal form of a carbohydrate).

If a disclosed compound or a pharmaceutically acceptable form of the compound incorporates an amine functional group, a prodrug can be formed by the replacement of a hydrogen atom in the amine group with a group such as R-carbonyl, RO-carbonyl, NRR'-carbonyl where R and R' are each independently ($C_1$-$C_{10}$)alkyl, ($C_3$-$C_7$)cycloalkyl, benzyl, or R-carbonyl is a natural α-aminoacyl or natural α-aminoacyl-natural α-aminoacyl, C(OH)C(O)OY$^1$ wherein Y$^1$ is H, ($C_1$-$C_6$)alkyl or benzyl, C(OY$^2$)Y$^3$ wherein Y$^2$ is ($C_1$-$C_4$) alkyl and Y$^3$ is ($C_1$-$C_6$)alkyl, carboxy($C_1$-$C_6$) alkyl, amino($C_1$-$C_4$)alkyl or mono-N or di-N,N($C_1$-$C_6$)alkylaminoalkyl, C(Y$^4$)Y$^5$ wherein Y$^4$ is H or methyl and Y$^5$ is mono-N or di-N,N($C_1$-$C_6$)alkylamino, morpholino, piperidin-1-yl or pyrrolidin-1-yl.

The use of prodrug systems is described in T. Järvinen et al., "Design and Pharmaceutical Applications of Prodrugs" in *Drug Discovery Handbook* (S. C. Gad, ed., Wiley-Interscience, Hoboken, NJ, 2005), ch. 17, pp. 733-796. Other alternatives for prodrug construction and use are known in the art. When a method or pharmaceutical composition according to the present invention, uses or includes a prodrug of a cannabinoid, terpenoid, or other therapeutically active agent, prodrugs and active metabolites of a compound may be identified using routine techniques known in the art. See, e.g., Bertolini et al., J. Med. Chem., 40, 2011-2016 (1997); Shan et al., J. Pharm. Sci., 86 (7), 765-767; Bagshawe, Drug Dev. Res., 34, 220-230 (1995); Bodor, Advances in Drug Res., 13, 224-331 (1984); Bundgaard, Design of Prodrugs (Elsevier Press 1985); Larsen, Design and Application of Prodrugs, Drug Design and Development (Krogsgaard-Larsen et al., eds., Harwood Academic Publishers, 1991); Dear et al., J. Chromatogr. B, 748, 281-293 (2000); Spraul et al., J. Pharmaceutical & Biomedical Analysis, 10, 601-605 (1992); and Prox et al., Xenobiol., 3, 103-112 (1992).

As used herein, the terms "cannabidiol," "CBD," or "cannabidiols" refer to one or more of the following compounds, and, unless a particular other stereoisomer or stereoisomers are specified, includes the compound "$\Delta^2$-cannabidiol." These compounds are: (1) $\Delta^5$-cannabidiol (2-(6-isopropenyl-3-methyl-5-cyclohexen-1-yl)-5-pentyl-1,3-benzenediol); (2) $\Delta^4$-cannabidiol (2-(6-isopropenyl-3-methyl-4-cyclohexen-1-yl)-5-pentyl-1,3-benzenediol); (3) $\Delta^3$-cannabidiol (2-(6-isopropenyl-3-methyl-3-cyclohexen-1-yl)-5-pentyl-1,3-benzenediol); (4) $\Delta^{3,7}$-cannabidiol (2-(6-isopropenyl-3-methylenecyclohex-1-yl)-5-pentyl-1,3-benzenediol); (5) $\Delta^2$-cannabidiol (2-(6-isopropenyl-3-methyl-2-cyclohexen-1-yl)-5-pentyl-1,3-benzenediol); (6) $\Delta^1$-cannabidiol (2-(6-isopropenyl-3-methyl-1-cyclohexen-1-yl)-5-pentyl-1,3-benzenediol); and (7) $\Delta^6$-cannabidiol (2-(6-isopropenyl-3-methyl-6-cyclohexen-1-yl)-5-pentyl-1,3-benzenediol).

These compounds have one or more chiral centers and two or more stereoisomers as stated below: (1) (1) $\Delta^5$-cannabidiol has 2 chiral centers and 4 stereoisomers; (2) $\Delta^5$-cannabidiol has 3 chiral centers and 8 stereoisomers; (3) $\Delta^3$-cannabidiol has 2 chiral centers and 4 stereoisomers; (4) $\Delta^{3,7}$-cannabidiol has 2 chiral centers and 4 isomers; (5) $\Delta^2$-cannabidiol has 2 chiral centers and 4 stereoisomers; (6) $\Delta^1$-cannabidiol has 2 chiral centers and 4 stereoisomers; and (7) $\Delta^6$-cannabidiol has 1 chiral center and 2 stereoisomers. In a preferred embodiment, canabidiol is specifically $\Delta^2$-cannabidiol. Unless specifically stated, a reference to "cannabidiol," "CBD," or "cannabidiols" or to any of specific cannabidiol compounds (1)-(7) as referred to above includes all possible stereoisomers of all compounds included by the reference. In one embodiment, "$\Delta^2$-cannabidiol" can be a mixture of the $\Delta^2$-cannabidiol stereoisomers that are present in a plant, or an extract thereof, such as *Cannabis sativa*, *Cannabis indica*, or another plant of the *Cannabis* genus. In another embodiment, "$\Delta^2$-cannabidiol" is a mixture of the $\Delta^2$-cannabidiol stereoisomers that are present in a plant, or an extract thereof, such as *Cannabis sativa*, *Cannabis indica*, or another plant of the *Cannabis* genus, wherein said mixture of stereoisomers is at, or at about, the naturally occurring ratio of isomers. In another embodiment, the "$\Delta^2$-cannabidiol" is a single stereoisomer.

As used herein, the term "cannabinol" or "CBN" refers to 6,6,9-trimethyl-3-pentylbenzo[c]chromen-1-ol. CBN has no double bond isomers nor stereoisomers.

Cannabinoids

Cannabinoids are a group of chemicals known to activate cannabinoid receptors in cells throughout the human body, including the skin. Phytocannabinoids are the cannabinoids derived from cannabis plants. They can be isolated from plants or produced synthetically. Endocannabinoids are endogenous cannabinoids found in the human body.

Cannabinoids exert their effects by interacting with receptors present on the surface of cells. To date, two types of cannabinoid receptor have been identified, the CB1 receptor and the CB2 receptor. These two receptors share about 48% amino acid sequence identity, and are distributed in different tissues and also have different signaling mechanisms. They also differ in their sensitivity to agonists and antagonists. As described herein, certain cannabinoids modulate the CB1 endocannabinoid receptors and may therefore modulate the pathways leading to nociception. In addition, the Transient Receptor Potential (TRP) channels have been demonstrated to be involved in chronic pain. And, there is growing evidence that cannabinoids can interact with TRP channel proteins, TRPV1-4, TRPA1 and TRPM8 to exert their influence on nociception.

Accordingly, in vitro and in vivo methods are described herein for screening for and identifying drug combinations that meet the following criteria: (1) cannabinoids or cannabinoid derivatives or analogs including classical cannabinoids, non-classical cannabinoids, aminoalkylindoles or eicosanoids that treat pain; (2) cannabinoids or cannabinoid derivatives or analogs including classical cannabinoids, non-classical cannabinoids, aminoalkylindoles or eicosanoids that treat, reduce, or reverse central or peripheral sensitization; (3) cannabinoids or cannabinoid derivatives or analogs including classical cannabinoids, non-classical cannabinoids, aminoalkylindoles or eicosanoids that relieve muscular pain, neuropathic pain, or joint pain (e.g., arthritis-induced joint pain); or (4) cannabinoids or cannabinoid derivatives or analogs including classical cannabinoids, non-classical cannabinoids, aminoalkylindoles or eicosanoids that treat chronic pain.

Typically, the therapeutically effective composition contains a cannabinoid or a mixture of cannabinoids. In a preferred embodiment, the composition contains cannabinol, optionally in combination with the cannabidiol $\Delta^2$-cannabidiol. In some embodiments, the mixture of cannabinoids is a mixture of cannabidiols selected from the group consisting of one or more of the cannabidiols described herein and cannabinol. In some cases, the ratio of the one or more cannabidiols (CBD) to cannabinol (CBN) is from 10:0.1 μg/mL to 0.1:10 μg/mL. In some cases, the CBD to CBN ratio is from 5:0.1 μg/mL to 0.1:5 μg/mL. In some cases, the CBD to CBN ratio is from 1:0.1 μg/mL to 0.1:1 μg/mL. In some cases, the CBD to CBN ratio is from 10:1 μg/mL to 1:10 μg/mL. In some cases, the CBD to CBN ratio is from 5:1 μg/mL to 1:5 μg/mL. In some cases, the CBD to CBN ratio is from 10:1 μg/mL to 1:1 μg/mL. In some cases, the CBD to CBN ratio is from 10:1 μg/mL to 2:1 μg/mL. In some cases, the CBD to CBN ratio is from 8:1 μg/mL to 4:1 μg/mL. In some cases, the CBD to CBN ratio is from 4:1 μg/mL to 2:1 μg/mL. In some cases, the CBD to CBN ratio is from 2:1 μg/mL to 1:1 μg/mL. In some cases, the CBD to CBN ratio is from 2:1 μg/mL to 1:2 μg/mL. In some cases, the CBD to CBN ratio is from 1.5:1 μg/mL to 1:1.5 μg/mL. In some cases, the CBD to CBN ratio is 10:1 μg/mL, 8:1 μg/mL, 5:1 μg/mL, 4:1 μg/mL, 2:1 μg/mL, 1:1 μg/mL, 0.75:1 μg/mL, 0.5:1 μg/mL, or 0.25:1 μg/mL. In some cases, the concentration of CBN is at least 0.1 μg/mL, 0.2 μg/mL, 0.5 μg/mL, or 1 μg/mL, and the concentration of CBD is at least 2, 3, 4, 5, 6, 7, 8, 9, or 10-fold higher than the concentration of CBN. A particularly preferred cannabidiol is $\Delta^2$-cannabidiol as described herein; this is the naturally-occurring form of cannabidiol, but other positional isomers differing in the positions of the double bond in the non-aromatic six-membered ring can alternatively be used.

In some embodiments, the therapeutically effective composition contains one or more cannabinoids, and does not contain CBC. In some embodiments, the therapeutically effective composition contains one or more cannabinoids, and does not contain CBCA. In some embodiments, the therapeutically effective composition contains one or more cannabinoids, and does not contain THC. In some embodiments, the therapeutically effective composition contains one or more cannabinoids, and does not contain THCA.

Additionally or alternatively, other cannabinoids can be used in methods according to the present invention. Such cannabinoids can be screened using the methods described herein to identify preferred cannabinoids and combinations thereof. These cannabinoids include, but are not limited to, $\Delta^9$-tetrahydrocannabinol ($\Delta^9$-THC), the synthetic cannabinoid HU-210 (6aR,10aR)-9-(hydroxymethyl)-6,6-dimethyl-3-(2-methyloctan-2-yl)-6H,6aH,7H,10H,10aH-benzo [c] isochromen-1-ol), cannabidivarin (CBDV), cannabichromene (CBC), cannabichromevarin (CBCV), cannabigerol (CBG), cannabigerovarin (CBGV), cannabielsoin (CBE),cannabicyclol (CBL),cannabivarin (CBV), and cannabitriol (CBT). Still other cannabinoids can be used, including tetrahydrocannibivarin (THCV) and cannabigerol monomethyl ether (CBGM). Additional cannabinoids occur and can be used, including cannabichromenic acid (CBCA), $\Delta^1$-tetrahydrocannabinolic acid (THCA); and cannabidiolic acid (CBDA); these additional cannabinoids are characterized by the presence of a carboxylic acid group in their structure. Still other cannabinoids include nabilone, rimonabant, JWH-018 (naphthalen-1-yl-(1-pentylindol-3-yl) methanone), JWH-073 naphthalen-1-yl-(1-butylindol-3-yl) methanone, CP-55940 (2-[(1R,2R,5R)-5-hydroxy-2-(3-hydroxypropyl) cyclohexyl]-5-(2-methyloctan-2-yl) phenol), dimethylheptylpyran, HU-331 (3-hydroxy-2-[(1R)-6-isopropenyl-3-methyl-cyclohex-2-en-1-yl]-5-pentyl-1,4-benzoquinone), SR144528 (5-(4-chloro-3-methylphenyl)-1-[(4-methylphenyl)methyl]-N-[(1S,2S,4R)-1,3,3-trimethylbicyclo[2.2.1]heptan-2-yl]-1H-pyrazole-3-carboxamide), WIN 55,212-2 ((11R)-2-methyl-11-[(morpholin-4-yl)methyl]-3-(naphthalene-1-carbonyl)-9-oxa-1-azatricyclo[6.3.1.0$^{4,12}$]dodeca-2,4(12),5,7-tetraene), JWH-133 ((6aR,10aR)-3-(1,1-dimethylbutyl)-6a,7,10,10a-tetrahydro-6,6,9-trimethyl-6H-dibenzo[b,d]pyran), levonatradol, and AM-2201 (1-[(5-fluoropentyl)-1H-indol-3-yl]-(naphthalen-1-yl)methanone). Other cannabinoids include $\Delta^8$-tetrahydrocannabinol ($\Delta^8$-THC), 11-hydroxy-$\Delta^9$-tetrahydrocannabinol, $\Delta^{11}$-tetrahydrocannabinol, and 11-hydroxy-tetracannabinol. In another alternative, analogs or derivatives of these cannabinoids can be used as described further below.

Synthetic cannabinoids are also disclosed in U.S. Pat. No. 9,394,267 to Attala et al.; U.S. Pat. No. 9,376,367 to Herkenroth et al.; U.S. Pat. No. 9,284,303 to Gijsen et al.; U.S. Pat. No. 9,173,867 to Travis; U.S. Pat. No. 9,133,128 to Fulp et al.; U.S. Pat. No. 8,778,950 to Jones et al.; U.S. Pat. No. 7,700,634 to Adam-Worrall et al.; U.S. Pat. No. 7,504,522 to Davidson et al.; U.S. Pat. No. 7,294,645 to Barth et al.; U.S. Pat. No. 7,109,216 to Kruse et al.; U.S. Pat. No. 6,825,209 to Thomas et al.; and U.S. Pat. No. 6,284,788 to Mittendorf et al.

U.S. Pat. No. 9,394,267 to Attala et al. discloses synthetic cannabinoids of Formula (C-I):

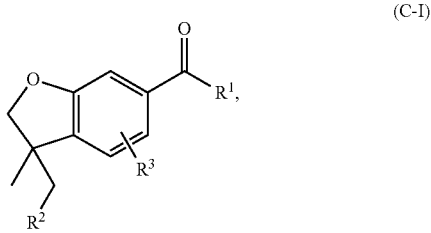

(C-I)

wherein:
(1) $R^1$ is selected from the group consisting of $NH_2$, $NHR^4$, and $NR^4R^5$, any carbon atom of which may be optionally substituted;

(2) $R^2$ is selected from the group consisting of hydrogen, aryl, alkyl, cycloalkyl, aralkyl, alkenyl, and alkynyl, any carbon atom of which may be optionally substituted;

(3) $R^3$ is selected from the group consisting of hydrogen, halogen, alkyl, cycloalkyl, heterocycloalkyl, aryl, and heteroaryl, any carbon atom of which may be optionally substituted; and (4) $R^4$ and $R^5$ vary independently and are selected from the group consisting of aryl, alkyl, cycloalkyl, aralkyl, alkenyl, and alkynyl, any carbon atom of which may be optionally substituted.

U.S. Pat. No. 9,394,267 to Attala et al. also discloses synthetic cannabinoids of Formula (C-II):

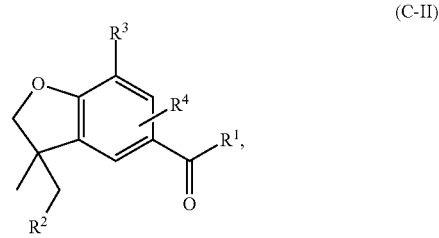

(C-II)

wherein:
(1) $R^1$ is selected from the group consisting of $NH_2$, $NHR^5$, and $NR^5R^6$, any carbon atom of which may be optionally substituted;

(2) $R^2$ is selected from the group consisting of hydrogen, aryl, alkyl, cycloalkyl, aralkyl, alkenyl, and alkynyl, any carbon atom of which may be optionally substituted;

(3) $R^3$ and $R^4$ are independently selected from the group consisting of hydrogen, halogen, alkyl, cycloalkyl, heterocycloalkyl, aryl, and heteroaryl;

(4) $R^5$ and $R^6$ are independently selected from the group consisting of aryl, alkyl, cycloalkyl, aralkyl, alkenyl, and alkynyl; and (5) when $R^2$ is hydrogen, $R^3$ is not t-butyl, bromo, methoxy, or a moiety of Subformula (C-II(a)):

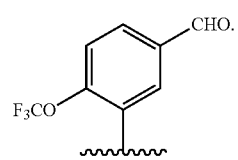

(C-II(a))

U.S. Pat. No. 9,376,367 to Herkenroth et al. discloses cannabinoid carboxylic acids and salts of cannabinoid carboxylic acids.

U.S. Pat. No. 9,284,303 to Gijsen et al. discloses benzimidazole cannabinoid agonists bearing a substituted heterocyclic group.

U.S. Pat. No. 9,173,867 to Travis discloses cannabinoid derivatives of Formula (C-III):

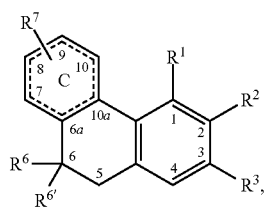

(C-III)

wherein:
(1) $R^1$ and $R^2$ are each hydrogen;
(2) $R^3$ is $(W)_m$—Y—$(Z)_n$, wherein: (a) W is a $C_5$-$C_{12}$ straight or branched-chain alkyl; (b) Y is a valence bond; (c) Z is a $C_5$-$C_{12}$ alkyl; and (d) m and n are different, and each is either 0 or 1;
(3) $R^6$ and $R^{6'}$ are each methyl;
(4) $R^7$ is methyl;
(5) Q is O; and
(6) the dashed line of Ring C represents a double bond at Δ8-9.

U.S. Pat. No. 9,133,128 to Fulp et al. discloses N-piperidine-containing cannabinoid analogs of Formula (C-IV):

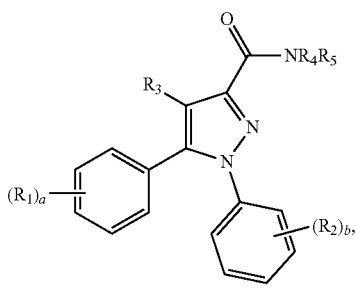

(C-IV)

wherein:
(1) $R_1$ and $R_2$ is a substituent independently selected from the group consisting of Cl, F, Br, OH, optionally substituted $C_1$-$C_{10}$ alkyl, optionally substituted $C_1$-$C_{10}$ alkoxy, optionally substituted $C_2$-$C_4$ alkenyl, optionally substituted $C_2$-$C_4$ alkynyl, $NR^{10}R^{11}$, $NHCOR^{10}$, $NHCO_2R^{10}$, $CH_2OR^{10}$, $CONR^{10}R^{11}$, $CO_2R^{10}$, CN, $CF_3$, $NO_2$, $N_3$, $C_1$-$C_3$ alkylthio, $R^{10}SO$, $R^{10}SO_2$, $CF_3S$, and $CF_3SO_2$;
(2) $R_3$ is H or $C_1$-$C_3$ alkyl;
(3) $R_4$ and $R_5$ taken together form a piperidine ring with the N to which they are attached, which is substituted at the 4 position with at least one substituent selected from the group consisting of $NR^{10}R^{11}$, $NR^{10}COR^{11}$, $NR^{10}SO_2R^{11}$, $NHCONR^{10}R^{11}$, $NR^{10}COOR^{11}$; and $CONR^{10}R^{11}$;
(4) $R^{10}$ and $R^{11}$ are independently selected from H and $C_1$-$C_{10}$ alkyl; and
(5) a and b are each independently integers from 0 to 5.

U.S. Pat. No. 8,778,950 to Jones et al. discloses pyrazine derivatives including (1aS,5aS)-2-pyrazin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide and (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide.

U.S. Pat. No. 7,700,634 to Adam-Worrall et al. discloses indolyl-3-yl cannabinoid analogs including 7-chloro-3-(5-{[N-ethyl-N-(2-methoxyethyl)amino]methyl}-[1,2,4]-thiadiazol-3-yl)-1-(tetrahydropyran-4-yl)methyl-1H-indole; 7-chloro-3-{5-[(pyrrolidin-1-yl)methyl]-[1,2,4]-thiadiazol-3-yl}-1-(tetrahydropyran-4-yl)methyl-1H-indole; 7-chloro-3-(5-{[N-ethyl-N-(2-hydroxyethyl)amino]methyl}-[1,2,4]-thiadiazol-3-yl)-1-(tetrahydropyran-4-yl)methyl-1H-indole; 7-chloro-3-(4-{[N-(2-hydroxyethyl)-N-isopropylamino]methyl}-[1,3]-thiazol-2-yl)-1-(tetrahydropyran-4-yl)methyl-1H-indole; 7-chloro-3-(4-{[N-ethyl-N-(2-hydroxyethyl)amino]methyl}-[1,3]-thiazol-2-yl)-1-(tetrahydropyran-4-yl)methyl-1H-indole; 7-chloro-3-(4-{[N-(2-methoxyethyl)-N-methylamino]methyl}-[1,3]-thiazol-2-yl)-1-(tetrahydropyran-4-yl)methyl-1H-indole; and 7-chloro-3-{5-[(2,2-dimethyl-pyrrolidin-1-yl)methyl]-[1,2,4]oxadiazol-3-yl}-1-(tetrahydropyran-4-yl)methyl-1H-indole.

U.S. Pat. No. 7,504,522 to Davidson et al. discloses azetidinecarboxamine cannabinoid derivatives of Formula (C-V):

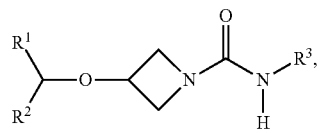

(C-V)

wherein:
(1) $R^1$ and $R^2$ are each independently selected from aryl; and
(2) $R^3$ is hydrogen or alkyl;
wherein at least one of $R^1$ and $R^2$ has a non-hydrogen substituent in the ortho position or positions relative to the point of attachment to the [—CH—O—] group.

U.S. Pat. No. 7,294,645 to Barth et al. discloses derivatives of N'-(1,5-diphenyl-1H-pyrazol-yl)sulfonamide as cannabinoid analogs of Formula (C-VI):

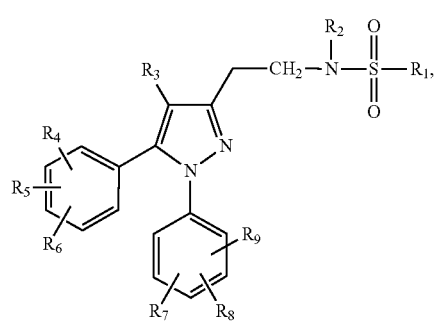

(C-VI)

wherein:
(1) $R_1$ represents a $(C_1$-$C_6)$alkyl; a $(C_3$-$C_7)$cycloalkyl which is unsubstituted or substituted once or several times with a $(C_1$-$C_6)$alkyl group; a $(C_3$-$C_7)$cycloalkylmethyl which is unsubstituted or substituted once or several times on the carbocycle with a $(C_1$-$C_3)$alkyl; a phenyl which is unsubstituted or mono-, di- or trisubstituted with a substituent independently chosen from a halogen atom, a $(C_1$-$C_4)$alkyl, a $(C_1$-$C_6)$alkoxy, a cyano, a trifluoromethyl radical, a trifluoromethoxy radical, an $S(O)_n$Alk group, a $(C_1$-$C_3)$alkylcarbonyl group, a phenyl; a benzyl which is unsubstituted or mono- or disubstituted with a substituent independently chosen from a halogen atom, a $(C_1$-$C_3)$alkyl, a $(C_1$-$C_3)$ alkoxy; a trifluoromethyl radical; a thienyl which is unsubstituted or substituted with a halogen atom or with an isoxazolyl;

(2) $R_2$ represents a hydrogen atom or a $(C_1-C_3)$alkyl;
(3) $R_3$ represents a hydrogen atom or a $(C_1-C_5)$alkyl;
(4) $R_4$, $R_5$, $R_6$, $R_7$, $R_8$ and $R_9$ each independently represent a hydrogen atom, a halogen atom, a $(C_1-C_7)$alkyl, a $(C_1-C_5)$alkoxy, a trifluoromethyl radical or an $S(O)_n$Alk group;
(5) n represents 0, 1 or 2; and
(6) Alk represents a $(C_1-C_4)$alkyl.

U.S. Pat. No. 7,109,216 to Kruse et al. discloses cannabinoid analogs that are 1H-imidazole derivatives of Formula (C-VII):

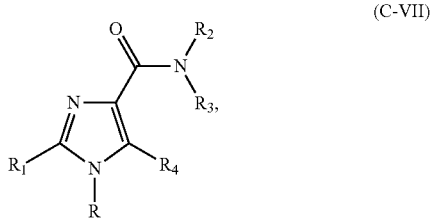

(C-VII)

wherein:
(1) R represents phenyl, thienyl, 2-pyridinyl, 3-pyridinyl, 4-pyridinyl, pyrimidinyl, pyrazinyl, pyridazinyl or triazinyl, which groups may be substituted with 1, 2, 3 or 4 substituents Y, which can be the same or different, from the group $C_1-C_3$ alkyl or alkoxy, hydroxy, halogen, trifluoromethyl, trifluoromethylthio, trifluoromethoxy, nitro, amino, mono- or dialkyl $(C_1-C_2)$-amino, mono- or dialkyl $(C_1-C_2)$-amido, $(C_1-C_3)$-alkoxycarbonyl, carboxyl, cyano, carbamoyl and acetyl, or R represents naphthyl, with the proviso that when R is 4-pyridinyl, $R_4$ represents a halogen atom or a cyano, carbamoyl, formyl, acetyl, trifluoroacetyl, fluoroacetyl, propionyl, sulfamoyl, methanesulfonyl, methylsulfanyl or branched or unbranched $C_1-C_4$ alkyl group, which $C_1-C_4$ alkyl group may be substituted with 1 to 3 fluoro atoms or with a bromo, chloro, iodo, cyano or hydroxy group;
(2) $R_1$ represents phenyl or pyridinyl, which groups may be substituted with 1 to 4 substituents Y, which can be the same or different, wherein Y has the above mentioned meaning, or $R_1$ represents pyrimidinyl, pyrazinyl, pyridazinyl or triazinyl, which groups may be substituted with 1 or 2 substituents Y, which can be the same or different or $R_1$ represents a five-membered aromatic heterocyclic ring having one or two heteroatoms from the group (N, O, S), which heteroatoms can be the same or different, which five-membered aromatic heterocyclic ring may be substituted with 1 2 substituents Y, which can be the same or different or $R_1$ represents naphthyl;
(3) $R_2$ represents H, branched or unbranched $C_1-C_8$ alkyl, $C_3-C_8$ cycloalkyl, $C_3-C_8$ alkenyl, $C_5-C_8$ cycloalkenyl which groups may contain a sulfur, oxygen or nitrogen atom;
(4) $R_3$ represents branched or unbranched $C_2-C_8$ alkyl, $C_1-C_8$ alkoxy, $C_5-C_8$ cycloalkyloxy, $C_5-C_8$ cycloalkyl, $C_5-C_8$ bicycloalkyl, $C_6-C_{10}$ tricycloalkyl, $C_3-C_8$ alkenyl, $C_5-C_8$ cycloalkenyl, which groups may optionally contain one or more heteroatoms from the group (O, N, S) and which groups may be substituted with a hydroxy group or 1 or 2 $C_1-C_3$ alkyl groups or 1 to 3 fluoro atoms, or $R_3$ represents a benzyl or phenethyl group which aromatic rings may be substituted with 1 to 5 substituents Z, which can be the same or different, from the group $C_1-C_3$ alkyl or alkoxy, hydroxy, halogen, trifluoromethyl, trifluoromethylthio, trifluoromethoxy, nitro, amino, mono- or dialkyl $(C_1-C_2)$-amino, mono- or dialkyl $(C_1-C_2)$-amido, $(C_1-C_3)$-alkylsulfonyl, dimethyl-sulfamido, $C_1-C_3$-alkoxycarbonyl, carboxyl, trifluoromethylsulfonyl, cyano, carbamoyl, sulfamoyl and acetyl, or $R_3$ represents a phenyl or pyridinyl group, which groups are substituted with 1 to 4 substituents Z, wherein Z has the meaning as indicated above, or $R_3$ represents a pyridinyl group, or $R_3$ represents a phenyl group, with the proviso that $R_4$ represents a halogen atom or a cyano, carbamoyl, formyl, acetyl, trifluoroacetyl, fluoroacetyl, propionyl, sulfamoyl, methanesulfonyl, methylsulfanyl or $C_1-C_4$ alkyl group, which $C_1-C_4$ alkyl group may be substituted with 1 to 3 fluoro atoms or with a bromo, chloro, iodo, cyano or hydroxy group, or $R_3$ represents a group $NR_5R_6$, with the proviso that $R_2$ represents a hydrogen atom or a methyl group, wherein $R_5$ and $R_6$ are the same or different and represent branched or unbranched $C_1-C_4$ alkyl, or $R_5$ and $R_6$—together with the nitrogen atom to which they are bonded—form a saturated or unsaturated, monocyclic or bicyclic heterocyclic group having 4 to 10 ring atoms which heterocyclic group contains one or two heteroatoms from the group (N, O, S), which heteroatoms can be the same or different, which heterocyclic group may be substituted with a $C_1-C_3$ alkyl group or a hydroxy group, or $R_2$ and $R_3$—together with the nitrogen atom to which they are bonded—form a saturated or unsaturated heterocyclic group having 4 to 10 ring atoms which heterocyclic group contains one or two heteroatoms from the group (N, O, S), which heteroatoms can be the same or different, which heterocyclic group may be substituted with a $C_1-C_3$ alkyl group or a hydroxy group; and (5) $R_4$ represents a hydrogen or halogen atom or a cyano, carbamoyl, formyl, acetyl, trifluoroacetyl, fluoroacetyl, propionyl, sulfamoyl, methanesulfonyl, methylsulfanyl or branched or unbranched $C_1-C_4$ alkyl group, which $C_1-C_4$ alkyl group may be substituted with 1 to 3 fluoro atoms or with a bromo, chloro, iodo, cyano or a hydroxy group.

U.S. Pat. No. 6,825,209 to Thomas et al. discloses analogs of cannabinoids that are amide analogs and include compounds of Formula (C-VIII):

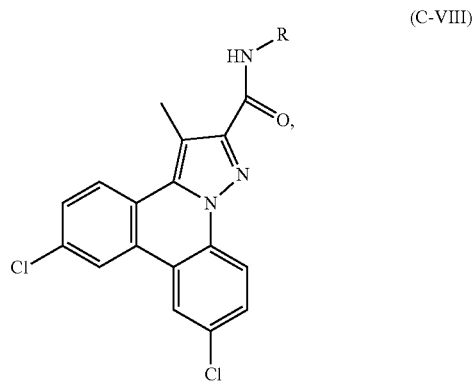

(C-VIII)

wherein R is a linear or branched hydrocarbon group of 7 to 12 carbons or N-piperidinyl.

U.S. Pat. No. 6,284,788 to Mittendorf et al. discloses a number of cannabinoid derivatives and analogs including classical cannabinoids, non-classical cannabinoids, aminoalkylindoles and eicosanoids.

In another alternative, the cannabinoid can be an endocannabinoid or a derivative or analog thereof. Endocannabinoids include but are not limited to anandamide, 2-arachidonoylglycerol, 2-arachidonyl glyceryl ether, N-arachidonoyl dopamine, and virodhamine. A number of analogs of endocannabinoids are known, including 7,10,13,16-docosatetraenoylethanolamide, oleamide, stearoylethanolamide, and homo-γ-linolenoylethanolamine, are also known.

In general, cannabinoids suitable for use in methods and compositions according to the present invention are either selective for the CB2 cannabinoid receptor or are non-selective for the two cannabinoid receptors, binding to either the CB1 cannabinoid receptor or the CB2 cannabinoid receptor. Preferably, cannabinoids suitable for use in methods and compositions according to the present invention are selective for the CB2 cannabinoid receptor. In some cases, the cannabinoids, or one of the cannabinoids in a mixture of cannabinoids is an antagonist (e.g., selective or non-selective antagonist) of CB2.

In some cases, the cannabinoids, or one of the cannabinoids in a mixture of cannabinoids is an antagonist (e.g., selective or non-selective antagonist) of CB2. In some cases, the cannabinoids, or one of the cannabinoids in a mixture of cannabinoids is an inverse agonist (e.g., selective or non-selective inverse agonist) of CB2. In some cases, the cannabinoids, or one of the cannabinoids in a mixture of cannabinoids is a neutral antagonist (e.g., selective or non-selective neutral antagonist) of CB2. In some cases, the cannabinoids, or one of the cannabinoids in a mixture of cannabinoids is a partial agonist (e.g., selective or non-selective neutral agonist) of CB2.

In some embodiments, cannabinoids suitable for use in methods and compositions according to the present invention are selective for the CB1 cannabinoid receptor. In some cases, the cannabinoids, or one of the cannabinoids in a mixture of cannabinoids is an antagonist (e.g., selective or non-selective antagonist) of CB1. In some cases, the cannabinoids, or one of the cannabinoids in a mixture of cannabinoids is an inverse agonist (e.g., selective or non-selective inverse agonist) of CB1. In some cases, the cannabinoids, or one of the cannabinoids in a mixture of cannabinoids is a neutral antagonist (e.g., selective or non-selective neutral antagonist) of CB1. In some cases, the cannabinoids, or one of the cannabinoids in a mixture of cannabinoids is a partial agonist (e.g., selective or non-selective neutral agonist) of CB1.

Typically, the cannabinoid or mixture of cannabinoids is administered in a pharmaceutical composition which optionally includes one or more terpenoids. The pharmaceutical composition includes: (1) a therapeutically effective quantity of the cannabinoid or the mixture of cannabinoids; and (2) at least one pharmaceutically acceptable carrier for topical administration of the composition. Suitable pharmaceutically acceptable carriers include Labrasol (caprylocaproyl polyoxyl-8 glycerides), 2-(2-ethoxyethoxy)ethanol, poloxamer such as poloxamer 407, lecithin or lysolecithin, or a combination thereof, and isopropyl palmitate or isopropyl myristate or a combination thereof. A preferred pharmaceutical composition includes Labrasol, poloxamer 407, lecithin, and isopropyl palmitate as pharmaceutically acceptable carriers. Another preferred pharmaceutical composition includes 2-(2-ethoxyethoxy)ethanol, poloxamer 407, lecithin, and isopropyl palmitate as pharmaceutically acceptable carriers. Further alternatives for pharmaceutically acceptable carriers or combinations of pharmaceutically acceptable carriers are described herein.

In some embodiments, the pharmaceutical composition comprises a lipophilic phase and a hydrophilic phase. The lipophilic phase can comprise lecithin and/or lysolecithin. The lipophilic phase can comprise or further comprise isopropyl myristate and/or isopropyl palmitate. The hydrophilic phase can comprise a poloxamer (e.g., poloxamer 407) or a mixture of poloxamers. In some embodiments, the lipophilic phase of the pharmaceutical composition is from about 20% to about 40% of the pharmaceutical composition, from about 25% to about 40% of the pharmaceutical composition, from about 30% to about 40% of the pharmaceutical composition, from about 25% to about 35% of the pharmaceutical composition, or about 30% or 35% of the pharmaceutical composition.

In some embodiments, the hydrophilic phase of the pharmaceutical composition is from about 60% to less than about 80% of the pharmaceutical composition, from about 60% to less than about 70% of the pharmaceutical composition, or about 60% or 65% of the pharmaceutical composition.

In some embodiments, the lipophilic phase comprises Labrosol and/or 2-(2-ethoxyethoxy)ethanol at a concentration of from about 1% to about 20%, from about 5% to about 15%, from about 5% to about 10%, from about 1% to about 10%, or about 5% or 10% of the lipophilic phase. In some embodiments, the lipophilic phase comprises isopropyl palmitate or isopropyl myristate or a combination thereof at a concentration of from about 15% to about 30%, from about 15% to about 25%, from about 5% to about 20%, from about 5% to about 15%, from about 15% to about 28%, from about 18% to about 28%, from about 18% to about 26%, or from 18.75% to 26%. In some embodiments, the ratio of lecithin or lysolecithin to isopropyl palmitate or isopropyl myristate in the lipophilic phase is from about 1:1 to about 1:10, from about 1:1 to about 1:6, from about 1:1 to about 1:3, from about 1:3 to about 1:10, from about 1:6 to about 1:10, or from about 1:3 to about 1:6.

In some embodiments, the poloxamer (e.g., poloxamer 407) comprises from about 10% to no more than about 30% of the hydrophilic phase. In some embodiments, the poloxamer comprises from about 10% to no more than about 25% of the hydrophilic phase, from about 15% to about 25% of the hydrophilic phase, or about 20% or 25% of the hydrophilic phase.

In some embodiments, the pharmaceutical composition comprises the cannabinoid or mixture of cannabinoids at a concentration of from about 0.001% to about 3%, from about 0.002% to about 3%, from about 0.002% to about 2%, from about 0.002% to about 1%, from about 0.002% to about 0.5%, from about 0.002% to about 0.2%, from about 0.002% to about 0.1%, from about 0.01% to about 1%, from about 0.01% to about 0.5%, from about 0.01% to about 0.2%, from about 0.01% to about 0.1%, from about 0.02% to about 1%, from about 0.02% to about 0.5%, from about 0.02% to about 0.2%, from about 0.02% to about 0.1%, from about 1% to about 3%, from about 0.5% to about 1%, or from about 0.05% to about 0.1%. In some embodiments, the pharmaceutical composition comprises a mixture of two cannabinoids at a total cannabinoid concentration as described in one of the foregoing concentrations or concentration ranges and at a ratio of from (1:0.1) to (0.1:1), from (1:5) to (5:1), or at a ratio of 1:1, 1:2, 1:5, 1:10, 1:15, 1:20, 1:25, 1:50, 1:75, or 1:100. In some embodiments, the foregoing ratios refer to a ratio of cannabidiols:cannabinol. In some embodiments, the foregoing ratios refer to a ratio of cannabinol:cannabidiols.

Terpenoids

Terpenoids interact with and potentiate the activity of cannabinoids, although by themselves, they do not have cannabinoid activity and do not bind to cannabinoid receptors. In some embodiments, the method can further comprise simultaneous or sequential topical administration of a therapeutically effective quantity of a terpenoid in the same or a different pharmaceutical composition.

When the cannabinoid to be administered is CBD (cannabidiols), CBG (cannabigerol), or CBN (cannabinol), suitable terpenoids include but are not limited to borneol, carvophyllene, 1,8-cineol, p-cymene, fenchone, α-humulene, kaempferol, limonene, linoleic acid, α-linolenic acid, luteolin, β-myrcene, oleic acid, orientin, α-pinene, phytol, quercetin, selinene, sitosterol, terpinenol-4, N-trans-caffeoyltyramine, N-trans-coumaroyltyramine, N-trans-feruloyltyramine, and vitexin. This combination of cannabinoids and terpenoids is particularly effective in promoting anti-inflammatory activity.

When the cannabinoid to be administered is CBC (cannabichromene), CBD, CBG, or CBN, suitable terpenoids include but are not limited to caryophyllene oxide, camphene, 1,8-cineole, p-cymene, kaempferol, limonene, linalool, nerolidol, α-pinene, β-pinene, phytol, β-sitosterol, and N-trans-caffeoyltyramine. This combination of cannabinoids and terpenoids is particularly effective in promoting anti-microbial activity.

When the cannabinoid to be administered is CBD or $\Delta^8$-THC ($\Delta^8$-tetrahydrocannabinol), suitable terpenoids include but are not limited to apigenin, caryophyllene, linoleic acid, luteolin, quercetin, and phytol. This combination of cannabinoids and terpenoids is particularly effective in promoting anti-itch activity.

When the cannabinoid is CBC, CBD, CBG, CBN, or $\Delta^9$-THC ($\Delta^9$-tetrahydrocannabinol), suitable terpenoids include but are not limited to borneol, caryophyllene, p-cymene, linalool, β-sitosterol, and vitexin. This combination of cannabinoids and terpenoids is particularly effective in promoting anti-pain activity.

When the cannabinoid is CBD, CBG, CBN, $\Delta^8$-THC, or $\Delta^9$-THC, suitable terpenoids include but are not limited to borneol, linalool, and kaempferol. This combination of cannabinoids and terpenoids is particularly effective in promoting wound healing activity.

Pharmaceutical Compositions

Pharmaceutical compositions according to the present invention can include one or more excipients. Such excipients that are suitable for use in topical compositions intended for application to the skin include, but are not limited to: preservatives; thickening agents; buffers; liquid carriers; isotonic agents; wetting, solubilizing, and emulsifying agents; acidifying agents; antioxidants; alkalinizing agents; carrying agents; chelating agents; complexing agents; solvents; suspending or viscosity-increasing agents; oils; penetration enhancers; polymers; stiffening agents; proteins; carbohydrates; and bulking agents.

As is generally known in the art of pharmaceutical formulation, a particular excipient can fulfill one or more of these functions in a particular pharmaceutical composition, depending on the concentration of the excipient, the other excipients in the composition, the physical form of the composition, the concentration of active agent in the composition, the intended route of administration of the composition, and other factors. The recitation of a particular excipient in a category below is not intended to exclude the possible use of the excipient in another category or categories.

The liquid carrier can be, but is not limited to, a liquid carrier selected from the group consisting of saline, phosphate buffered saline, glycerol, and ethanol.

A thickening agent can be, but is not limited to, a thickening agent selected from the group consisting of glycerol and propylene glycol.

An isotonic agent can be, but is not limited to: a polyalcohol selected from the group consisting of mannitol and sorbitol; sodium chloride; and potassium chloride.

The wetting, solubilizing, or emulsifying agent is generally a surfactant. Typically, the surfactant is selected from the group consisting of benzalkonium chloride, benzethonium chloride, cetylpyridinium chloride, docusate sodium, nonoxynol 9, nonoxynol 10, octoxynol 9, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaureate, sorbitan monooleate, sorbitan monopalmitate, sorbitan monostearate, tyloxapol, acacia, cholesterol, diethanolamine, glyceryl monostearate, lanolin alcohols, lecithin, mono- and di-glycerides, monoethanolamine (adjunct), oleic acid (adjunct), oleyl alcohol (stabilizer), poloxamer (e.g., poloxamer 407), polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, triethanolamine, emulsifying wax, cetomacrogol, and cetyl alcohol.

The pharmaceutical composition for topical application can include an emollient. As used herein, the term "emollient" refers to a hydrophobic agent that softens, smoothens and improves lipid content of the skin or other mucous membranes. Examples of suitable emollients for use include isostearic acid derivatives, isopropyl palmitate, isopropyl myristate, lanolin oil, diisopropyl dimerate, diisopropyl adipate, dimethyl isosorbide, maleated soybean oil, octyl palmitat, isopropyl isostearate, cetyl alcohol, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, hydrogenated cocoglycerides, isononyl isononanoate, isotridecyl isononanoate, myristyl myristate, triisocetyl citrate, octyl dodecanol, octyl hydroxystearate, grape seed oil, one or more ceramides, cyclomethicone, and mixtures thereof. Other examples of other suitable emollients can also be found in the Cosmetic Bench Reference, pp. 1.19-1.22 (1996). One of skill in the art will appreciate that other emollients are useful in the present invention.

The preservative can be selected from the group consisting of benzalkonium chloride, benzalkonium chloride solution, benzethonium chloride, benzoic acid, benzyl alcohol, butylparaben, cetylpyridinium chloride, chlorobutanol, chlorocresol, cresol, dehydroacetic acid, diazolidinyl urea, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, and thymol.

The composition can include a buffer selected from the group consisting of acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate, sodium bicarbonate, Tris (Tris(hydroxymethyl)aminomethane), MOPS (3-(N-morpholino)propanesulfonic acid), HEPES (N-(2-hydroxyethyl)piperazine-N'-(2-ethanesulfonic acid), ACES (2-[(2-amino-2-oxoethyl)amino]ethanesulfonic acid), ADA (N-(2-acetamido)2-iminodiacetic acid), AMPSO (3-[(1,1-dimethyl-2-hydroxyethylamino]-2-propanesulfonic acid), BES (N,N-bis(2-hydroxyethyl)-2-aminoethanesulfonic acid, Bicine (N,N-bis(2-hydroxyethylglycine), Bis-Tris (bis-(2-hydroxyethyl)imino-tris(hydroxymethyl)methane, CAPS (3-(cyclohexylamino)-1-propanesulfonic acid), CAPSO (3-(cyclohexylamino)-2-hydroxy-1-propanesulfonic acid), CHES (2-(N-cyclohexylamino)ethanesulfonic acid), DIPSO (3-[N,N-bis(2-hydroxyethylamino]-2-hydroxy-propane-sulfonic acid), HEPPS (N-(2-hydroxyethylpiperazine)-N'-(3-propanesulfonic acid), HEPPSO (N-(2-hydroxyethyl) piperazine-N'-(2-hydroxypropanesulfonic acid), MES (2-(N-morpholino)ethanesulfonic acid), triethanolamine, imidazole, glycine, ethanolamine, phosphate, MOPSO (3-(N-morpholino)-2-hydroxypropanesulfonic acid), PIPES (piperazine-N,N'-bis(2-ethanesulfonic acid), POPSO (piperazine-N,N'-bis(2-hydroxypropaneulfonic acid), TAPS (N-tris[hydroxymethyl)methyl-3-aminopropanesulfonic acid), TAPSO (3-[N-tris(hydroxymethyl)methylamino]-2-hydroxy-propanesulfonic acid), TES (N-tris(hydroxymethyl)methyl-2-aminoethanesulfonic acid), tricine (N-tris (hydroxymethyl)methylglycine), 2-amino-2-methyl-1,3-propanediol, and 2-amino-2-methyl-1-propanol.

Typically, the acidifying agent is selected from the group consisting of acetic acid, citric acid, fumaric acid, hydrochloric acid, diluted hydrochloric acid, malic acid, nitric acid, phosphoric acid, diluted phosphoric acid, sulfuric acid, and tartaric acid.

Typically, the antioxidant is selected from the group consisting of ascorbic acid, ascorbyl palmitate, butylated hydroxyanisole, butylated hydroxytoluene, hypophosphorous acid, monothioglycerol, propyl gallate, sodium ascorbate, sodium bisulfate, sodium formaldehyde sulfoxylate, sodium metabisulfite, sodium thiosulfate, sulfur dioxide, and tocopherol.

Typically, the alkalinizing agent is selected from the group consisting of strong ammonia solution, ammonium carbonate, diethanolamine, diisopropanolamine, potassium hydroxide, sodium bicarbonate, sodium borate, sodium carbonate, sodium hydroxide, and trolamine.

The carrying agent can be selected from the group consisting of corn oil, mineral oil, peanut oil, sesame oil, bacteriostatic sodium chloride and bacteriostatic water.

The chelating agent can be selected from the group consisting of edetate disodium, ethylenediaminetetraacetic acid, citric acid, and salicylates.

The complexing agent can be selected from the group consisting of ethylenediaminetetraacetic acid, salts of ethylenediaminetetraacetic acid, gentisic acid ethanolamide, and oxyquinoline sulfate.

The solvent can be selected from the group consisting of acetone, ethanol, diluted alcohol, amylene hydrate, benzyl benzoate, butyl alcohol, carbon tetrachloride, chloroform, corn oil, cottonseed oil, ethyl acetate, glycerol, hexylene glycol, isopropyl alcohol, methyl isobutyl ketone, mineral oil, oleic acid, peanut oil, polyethylene glycol, propylene carbonate, propylene glycol, sesame oil, water, sterile water, and purified water.

Typically, the suspending and/or viscosity-increasing agent is selected from the group consisting of acacia, agar, alginic acid, aluminum monostearate, bentonite, purified bentonite, magma bentonite, carbomers, carbomer 934p, carboxymethylcellulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, Veegum, and xanthan gum. In some embodiments, one or more other ingredients described herein also function as a suspending and/or viscosity-increasing agent. For example, poloxamers can serve as a wetting agent and a suspending and/or viscosity-increasing agent.

Typically, the oil is selected from the group consisting of arachis oil, mineral oil, olive oil, sesame oil, cottonseed oil, safflower oil, corn oil, and soybean oil.

Typically, the penetration enhancer is selected from the group consisting of monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones, and ureas.

Typically, the polymer is selected from the group consisting of cellulose acetate, alkyl celluloses, hydroxyalkylcelluloses, acrylic polymers and copolymers, polyesters, polycarbonates, and polyanhydrides.

Typically, the stiffening agent is selected from the group consisting of hydrogenated castor oil, cetostearyl alcohol, cetyl alcohol, cetyl esters wax, hard fat, paraffin, polyethylene excipient, stearyl alcohol, emulsifying wax, white wax, and yellow wax.

Typically, the protein is selected from the group consisting of bovine serum albumin, human serum albumin (HSA), recombinant human albumin (rHA), gelatin, and casein.

Typically, the carbohydrate is selected from the group consisting of fructose, maltose, galactose, glucose, D-mannose, sorbose, lactose, sucrose, trehalose, cellobiose, raffinose, melezitose, maltodextrins, dextrans, starches, mannitol, maltitol, lactitol, xylitol, sorbitol, and myoinositol.

Typically, the bulking agent is selected from the group consisting of polypeptides and amino acids.

The composition can further comprise a topical soothing agent for the skin, a topical anti-inflammatory agent, a topical anti-bacterial agent, a topical anti-fungal agent, a topical steroid, and a topical antioxidant.

Topical soothing agents for the skin typically include chamomile and aloe; other topical soothing agents are known in the art and can be used.

Topical anti-inflammatory agents typically include diclofenac, ketoprofen, ibuprofen, piroxicam, and indomethacin; other topical anti-inflammatory agents are known in the art and can be used.

Topical anti-bacterial agents typically include bacitracin, polymyxin B, erythromycin, sodium sulfacetamide, silver sulfadiazine, retapamulin, mupirocin, neomycin, and pramoxine; other topical anti-bacterial agents are known in the art and can be used.

Topical anti-fungal agents typically include benzoic acid, salicylic acid, undecylenic acid, ketoconazole, nystatin, naftifine, tolnaftate, miconazole, econazole, ciclopirox, oxiconazole, sertaconazole, efinaconazole, terbinafine, tavaborole, clotrimazole, sulconazole, and butenafine; other topical anti-fungal agents are known in the art and can be used.

Topical steroids typically include hydrocortisone, triamcinolone, fluocinolone, prednicarbate, desonide, betamethasone, halcinonide, diflorasone, fluocinolone, clobetasol, desoxymetasone, mometasone, clocortolone, fluticasone, fluocinonide, flurandrenolide, alclometasone, and halobetasol; other topical steroids are known in the art and can be used.

Topical antioxidants typically include vitamin C, vitamin E, and L-selenomethionine; other topical antioxidants are known in the art and can be used.

Other active agents can be included.

In an alternative, a number of these additional agents, such as a topical anti-inflammatory agent, a topical anti-bacterial agent, a topical anti-fungal agent, a topical steroid, and a topical anti-oxidant, can be administered separately, such as in one or more additional pharmaceutical compositions including one or more excipients as described above.

In some alternatives, including the use of prodrugs as described above, therapeutically active compounds used in methods and compositions according to the present invention, including but not limited to cannabinoids and terpenoids, are formed by covalently cross-linking one or more conjugation partners to the therapeutically active compound. Suitable reagents for cross-linking many combinations of functional groups are known in the art.

For example, electrophilic groups can react with many functional groups, including those present in proteins or polypeptides. Various combinations of reactive amino acids and electrophiles are known in the art and can be used. For example, N-terminal cysteines, containing thiol groups, can be reacted with halogens or maleimides. Thiol groups are known to have reactivity with a large number of coupling agents, such as alkyl halides, haloacetyl derivatives, maleimides, aziridines, acryloyl derivatives, arylating agents such as aryl halides, and others. These are described in G. T. Hermanson, "Bioconjugate Techniques" (Academic Press, San Diego, 1996), pp. 146-150.

The reactivity of the cysteine residues can be optimized by appropriate selection of the neighboring amino acid residues. For example, a histidine residue adjacent to the cysteine residue will increase the reactivity of the cysteine residue. Other combinations of reactive amino acids and electrophilic reagents are known in the art. For example, maleimides can react with amino groups, such as the ε-amino group of the side chain of lysine, particularly at higher pH ranges. Aryl halides can also react with such amino groups. Haloacetyl derivatives can react with the imidazolyl side chain nitrogens of histidine, the thioether group of the side chain of methionine, and the .epsilon.-amino group of the side chain of lysine. Many other electrophilic reagents are known that will react with the δ-amino group of the side chain of lysine, including, but not limited to, isothiocyanates, isocyanates, acyl azides, N-hydroxysuccinimide esters, sulfonyl chlorides, epoxides, oxiranes, carbonates, imidoesters, carbodiimides, and anhydrides. These are described in G. T. Hermanson, "Bioconjugate Techniques" (Academic Press, San Diego, 1996), pp. 137-146.

Additionally, electrophilic reagents are known that will react with carboxylate side chains such as those of aspartate and glutamate, such as diazoalkanes and diazoacetyl compounds, carbonydilmidazole, and carbodiimides. These are described in G. T. Hermanson, "Bioconjugate Techniques" (Academic Press, San Diego, 1996), pp. 152-154. Furthermore, electrophilic reagents are known that will react with hydroxyl groups such as those in the side chains of serine and threonine, including reactive haloalkane derivatives. These are described in G. T. Hermanson, "Bioconjugate Techniques" (Academic Press, San Diego, 1996), pp. 154-158. In another alternative embodiment, the relative positions of electrophile and nucleophile (i.e., a molecule reactive with an electrophile) are reversed so that the protein has an amino acid residue with an electrophilic group that is reactive with a nucleophile and the targeting molecule includes therein a nucleophilic group. This includes the reaction of aldehydes (the electrophile) with hydroxylamine (the nucleophile), described above, but is more general than that reaction; other groups can be used as electrophile and nucleophile. Suitable groups are well known in organic chemistry and need not be described further in detail.

Additional combinations of reactive groups for cross-linking are known in the art. For example, amino groups can be reacted with isothiocyanates, isocyanates, acyl azides, N-hydroxysuccinimide (NHS) esters, sulfonyl chlorides, aldehydes, glyoxals, epoxides, oxiranes, carbonates, alkylating agents, imidoesters, carbodiimides, and anhydrides. Thiol groups can be reacted with haloacetyl or alkyl halide derivatives, maleimides, aziridines, acryloyl derivatives, acylating agents, or other thiol groups by way of oxidation and the formation of mixed disulfides. Carboxy groups can be reacted with diazoalkanes, diazoacetyl compounds, carbonyldiimidazole, carbodiimides. Hydroxyl groups can be reacted with epoxides, oxiranes, carbonyldiimidazole, N,N'-disuccinimidyl carbonate, N-hydroxysuccinimidyl chloroformate, periodate (for oxidation), alkyl halogens, or isocyanates. Aldehyde and ketone groups can react with hydrazines, reagents forming Schiff bases, and other groups in reductive amination reactions or Mannich condensation reactions. Still other reactions suitable for cross-linking reactions are known in the art. Such cross-linking reagents and reactions are described in G. T. Hermanson, "Bioconjugate Techniques" (Academic Press, San Diego, 1996).

The amount of a given therapeutically active agent, such as, but not limited to, a cannabinoid or terpenoid as described above, that is included in a unit dose of a pharmaceutical composition according to the present invention will vary depending upon factors such as the particular compound, disease condition and its severity, the identity (e.g., weight) of the subject in need of treatment, but can nevertheless be routinely determined by one skilled in the art. The selected dosage level depends upon a variety of pharmacokinetic factors including the activity of the particular therapeutic agent, the route of administration, the time of administration, the rate of excretion of the particular compound being employed, the severity of the condition, other health considerations affecting the subject, and the status of liver and kidney function of the subject.

It also depends on the duration of the treatment, other drugs, compounds and/or materials used in combination with the particular therapeutic agent employed, as well as the age, weight, condition, general health and prior medical history of the subject being treated, and like factors. Methods for determining optimal dosages are described in the art, e.g., Remington: *The Science and Practice of Pharmacy*, Mack Publishing Co., 20$^{th}$ ed., 2000. Optimal dosages for a given set of conditions can be ascertained by those skilled in the art using conventional dosage-determination tests in view of the experimental data for an agent.

The compositions of the invention or compositions employed according to the present invention may be manufactured using techniques generally known for preparing pharmaceutical compositions, e.g., by conventional techniques such as mixing, dissolving, granulating, dragee-making, levitating, emulsifying, encapsulating, entrapping or lyophilizing Pharmaceutical compositions may be formulated in a conventional manner using one or more physiologically acceptable carriers, which may be selected from excipients and auxiliaries that facilitate processing of the active compounds into preparations.

Pharmaceutical compositions according to the present invention are usually administered to the subjects on multiple occasions. Intervals between single dosages can be weekly, monthly or yearly. Intervals can also be irregular as indicated by therapeutic response or other parameters well known in the art. Alternatively, the pharmaceutical composition can be administered as a sustained release formulation, in which case less frequent administration is required. Dosage and frequency vary depending on the half-life in the subject of the pharmacologically active agent included in a pharmaceutical composition. The dosage and frequency of administration can vary depending on whether the treatment is prophylactic or therapeutic.

In prophylactic applications, a relatively low dosage is administered at relatively infrequent intervals over a long period of time. Some subjects may continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the subject can be administered a prophylactic regime.

U.S. Pat. No. 6,573,292 to Nardella, U.S. Pat. No. 6,921,722 to Nardella, U.S. Pat. No. 7,314,886 to Chao et al., and U.S. Pat. No. 7,446,122 by Chao et al., which disclose methods of use of various pharmacologically active agents and pharmaceutical compositions in treating a number of diseases and conditions, including cancer, and methods of determining the therapeutic effectiveness of such pharmacologically active agents and pharmaceutical compositions, are all incorporated herein by this reference.

EXAMPLES

Example 1: Cannabinoids Decrease Nerve Growth Factor-Induced Muscle Sensitization through Peripheral Cannabinoid Receptors in Female Rats Introduction This study investigated whether peripheral application of cannabinoids can decrease nerve growth factor (NGF)-induced sensitization in female rat masseter muscle; a model which mimics the symptoms of myofacial temporomandibular disorders and fibromyalgia. Cannabinoid (CB) receptors CB1 and CB2 were expressed by trigeminal ganglion neurons that innervate the masseter muscle and also on their peripheral endings. Their expression was greater in TRPV1-positive ganglion neurons. Three days after intramuscular injection of NGF, ganglion neuron expression of CB1 and CB2, but not TPRV1, was decreased. Expression of CB1, but not CB2, was also found in satellite glial cells in the ganglion. In behavioral experiments, intramuscular injections (10 μl) of delta-9-tetrahydrocannabinol (THC, 1 mg/ml), cannabidiol (CBD, 5 mg/ml) and cannabinol (CBN, 1 mg/ml) decreased NGF-induced mechanical sensitization. No change in mechanical threshold was observed in the contralateral masseter muscles and no impairment of motor functions was found in behavioral inverted screen tests after intramuscular injections of THC, CBD or CBN. In anesthetized rats, the same concentrations of these cannabinoids increased the mechanical thresholds of masseter muscle mechanoreceptors. Co-administration of CB1 antagonist AM251 blocked the effect of THC on masseter muscle mechanoreceptors while the CB2 antagonist AM630 had no effect. These results show that reduced inhibitory input from the peripheral cannabinoid system may contribute to NGF-induced local myofacial sensitization of mechanoreceptors. Without wishing to be bound by theory, peripheral application of cannabinoids may counter this effect by activating the CB1 receptors on masseter muscle to provide analgesic relief without central side effects. The results of this study offer insights into development of myofacial pain disorders and whether peripheral cannabinoid receptors are targets for analgesia.

Materials and Methods

Animals

Female (259-350 g, n=55) Sprague-Dawley rats were used for all experiments. Animals were housed in groups of two with a 12-h light/dark cycle. Food and water were given ad libitum. All animal procedures were reviewed and approved by the University of British Columbia Animal Care Committee.

Drugs

THC, CBD, Cannabinol (CBN), Cannabichromene (CBC), 1-(2,4-dichlorophenyl)-5-(4-iodophenyl)-4-methyl-N-1-piperidinyl-1H-pyrazole-3-carboxamide (AM251) and [6-iodo-2-methyl-1-[2-(4-morpholinyl)ethyl]-1H-indol-3-yl](4-methoxyphenyl)-methanone (AM630) were purchased from Cayman Chemicals (Ann Arbor, USA). THC, CBD, AM251 and AM630 were dissolved in acetonitrile, while CBN and CBC were dissolved in methanol, all to a concentration of 10 mg/ml in a stock solution. Appropriate volumes of each solution were evaporated under nitrogen gas, and subsequently re-solubilized with 4% Tween 80 in isotonic saline to final concentrations used for injection.

Immunohistochemistry

To identify trigeminal ganglion neurons that innervate the masseter muscle, the fluorescent tracer dye Fast Blue (2%, Polysciences, Warrington, PA) was injected bilaterally into the masseter muscles of rats (n=5),7 days prior to euthanization. NGF (25 μg/ml, 10 μl, Sigma, St. Louis, MO) or vehicle (phosphate buffered saline, PBS, 10 μl) was injected into the left and right masseter muscles, respectively, three days before euthanization. Under deep isoflurane anesthesia, animals were perfused with 120 ml cold saline followed by 120 ml of paraformaldehyde (4%). Trigeminal ganglia and masseter muscles were removed, incubated in 20% and then 40% sucrose for 48h each to cryoprotect the tissue, and cut into 10 μm sections with a cryotome. Trigeminal ganglia sections were treated with 5% normal goat serum (NGS) in PBS for 1 h and incubated overnight with commercially available primary antibodies against CB1 (Santa Cruz Biotechnology, Dallas, Texas) and CB2 receptors (ABCAM, Cambridge, MA), TRPV1 channels (ABCAM, Cambridge, MA). Satellite glial cells were identified by primary antibody against glutamine synthetase (GS; ABCAM, Cambridge, MA). Masseter muscle sections were treated with primary antibodies against PGP9.5 (ABCAM, Cambridge, MA), CB1 and CB2 receptors as described above. The next morning sections were washed several times with PBS and then incubated for 1 h at room temperature in the dark in the presence of appropriate secondary antibodies with fluorescent tracers attached. After several washes in buffer, all sections were mounted on slides with covers slips and visualized with a Leica TCS SPE confocal microscope. Fast Blue positive cells were counted and photographed for estimation of cell diameter. Neurons were considered positive when the intensity of the fluorescent tracer signal exceeded the 95% confidence interval of the mean background intensity. The minimum accepted length for a labeled nerve fiber was 1 µm in the masseter muscle. Specificity of the antibodies was confirmed by omission of the primary antibodies. Pre-absorption of the primary antibody with the appropriate antigen was performed for the CB1 antibody in a previous study (22), while the specificity for the CB2 antibody was previously confirmed in knockout rats (23).

Behavioral Experiments
Administration of NGF and Cannabinoids

Three days before behavioral experiments, rats received an injection of NGF (25 µg/ml, 10 µl, Sigma, St. Louis, MO) or vehicle (phosphate buffered saline, PBS, 10 µl) into the left and right masseter muscles, respectively, under brief isoflurane anesthesia. NGF has been shown to induce local mechanical sensitization at the site of injection which lasts from 3h to 5 days after injection in the female rats (15). This is accompanied by an increase in NMDA receptor expression in peripheral trigeminal ganglion neurons with a peak at three days after injection (15). To determine the effects of peripheral application of cannabinoids on NGF-induced sensitization, cannabinoids (THC, CBD, CBN, CBC) or vehicle were injected into the left (NGF-injected) masseter muscle of rats under brief isoflurane anesthesia. The masseter muscle region was shaved prior to injection and the injection sites were marked with a permanent marker for subsequent identification. The concentration of NGF was selected based on the concentration used in previous human experimental pain studies and experiments in rats (15, 24, 25, 26, 27). The investigator was blinded to the identity of the treatment groups until after all data was collected.

Mechanical Threshold (MT)

MT was assessed with a rigid electronic von Frey hair (IITC Life Science, Woodland Hills, CA). Before NGF injection, rats were habituated to restraint in a towel. The electronic von Frey hair was applied perpendicularly to the masseter muscle and the force was gradually increased until the animal moved its head away from the stimulus. The mechanical test stimulus was applied at 1 min intervals for 5 min and the average was calculated for further analysis. MT was measured daily for 5 days prior to the start of the experiment to determine that measurements were stable. MT readings recorded prior to NGF injection were used as naïve baseline. After induction of the NGF-induced sensitization, behavioral testing was performed to evaluate the antinociceptive effects of THC, CBD, CBN and CBC, and the vehicle control groups (n=6/group) at 3 days after NGF injection. On the test day, a post-NGF injection baseline (NGF baseline) was recorded before injection of cannabinoid treatment groups. After treatment injections, MT was measured at 10, 30, 60, and 120 min after injection.

Inverted Screen Test

A modified version of the inverted screen test was performed to evaluate impaired motor function in rats (28, 29). Rats (n=4/group) were placed on a screen (185 mm×290 mm) with 5 mm diameter holes and the screen was slowly inverted 180 degrees until the rats were suspended upside down on the bottom of the screen. The animals were observed for their ability to climb to the top of the screen in the next 60 seconds and were assigned to a score: (0) animals successfully climbed to the top the screen; (1) held on the screen upside down; (2) or fell from the screen. The rats were trained how to perform the test daily for three days before they were tested. Baselines were measured at the beginning prior to treatment and the animals were re-tested at 10, 30, 60 and 120 min after treatment administration (THC, CBD and CBN).

In Vivo Electrophysiology

In vivo electrophysiology recordings of single ganglion neurons that innervate the craniofacial muscles were performed to investigate the mechanism of action of peripherally injected cannabinoids. Rats (n=6/group) from the behavioral experiments were used for subsequent in vivo electrophysiological experiments. Recordings were performed at least 7 days after the behavioral experiments and experiments were conducted on the PBS-injected masseter muscles (right side) of the rats to minimize potential residual effects of the previous cannabinoid treatments.

Rats were anesthetized with isoflurane (2-2.5% in oxygen 97-98%; AErrane; Baxter) and surgically prepared for electrophysiological recording. Heart rate, blood pressure and body temperature were monitored and a trachea tube was inserted for ventilation throughout the experiment. The hair of the face was shaved and the animal's head was positioned in a stereotaxic frame. A diagram of the experimental setup is shown in FIG. 1.

A parylene-coated tungsten microelectrode (0.10", 2 MΩ, A-M Systems Inc.) was lowered into the trigeminal ganglion through the brain via a small trephination in the skull. An incision was made over the neck to expose the brain stem, and the dura was removed to allow access for a stimulating electrode to contact the caudal brain stem. Mechanoreceptors innervating craniofacial muscles (masseter and temporalis) were identified by mechanical probing using a fine-tipped cotton swab. Antidromic collisions were performed to confirm projection of the muscle fiber to the caudal brain stem (16, 30).

A stimulating electrode (parylene-coated tungsten microelectrode, 0.10", 2 MΩ, A-M Systems Inc.) was lowered into the ipsilateral caudal brainstem and a constant-current electrical stimulus (100 µs biphasic pulse, 10-90 µA, 0.5 Hz) was applied to evoke antidromic action potentials. Orthodromic action potentials were evoked by mechanical stimulation of the tissue. Collision was demonstrated by disappearance of the antidromic spike. The straight line distance between the stimulating and recording electrodes was divided by the latency of the antidromic action potential to estimate conduction velocity. MT was assessed with an electronic von Frey hair (IITC Life Science) by applying mechanical stimuli at 1 min intervals for 10 min to obtain baseline threshold. After baseline measurement, treatment was administered and MT was reassessed at 10, 30, 60, and 120 minutes thereafter. At the end of the experiments, animals were euthanized with pentobarbital (Nembutal 100 mg/kg, Abbott Laboratories, Chicago, IL).

Data Analysis

For the immunohistochemistry experiment, the frequency of expression of CB1, CB2 and TRPV1, respectively, in trigeminal ganglion neurons between NGF and vehicle-injected sides was analyzed with a paired Student's t-test. For the behavioral and electrophysiological experiments, MT from NGF and vehicle-injected sides was analyzed with a two-way repeated measures analysis of variance (ANOVA) with time and treatment as factors. Relative mechanical activation threshold (Rel MT) was calculated as 100×Post-treatment MT/Baseline MT. Post hoc Holm Sidak's multiple comparison tests were used to compare post injection mechanical thresholds between treatment groups at each time point. One-way repeated measures ANOVA on ranks was used to analyze test scores in the inverted screen tests. A probability level of 0.05 was considered significant for all tests. Error bars represented standard error of the mean.

Results

Expression of Cannabinoid Receptors on Masseter Ganglion Neurons

Figure 4:
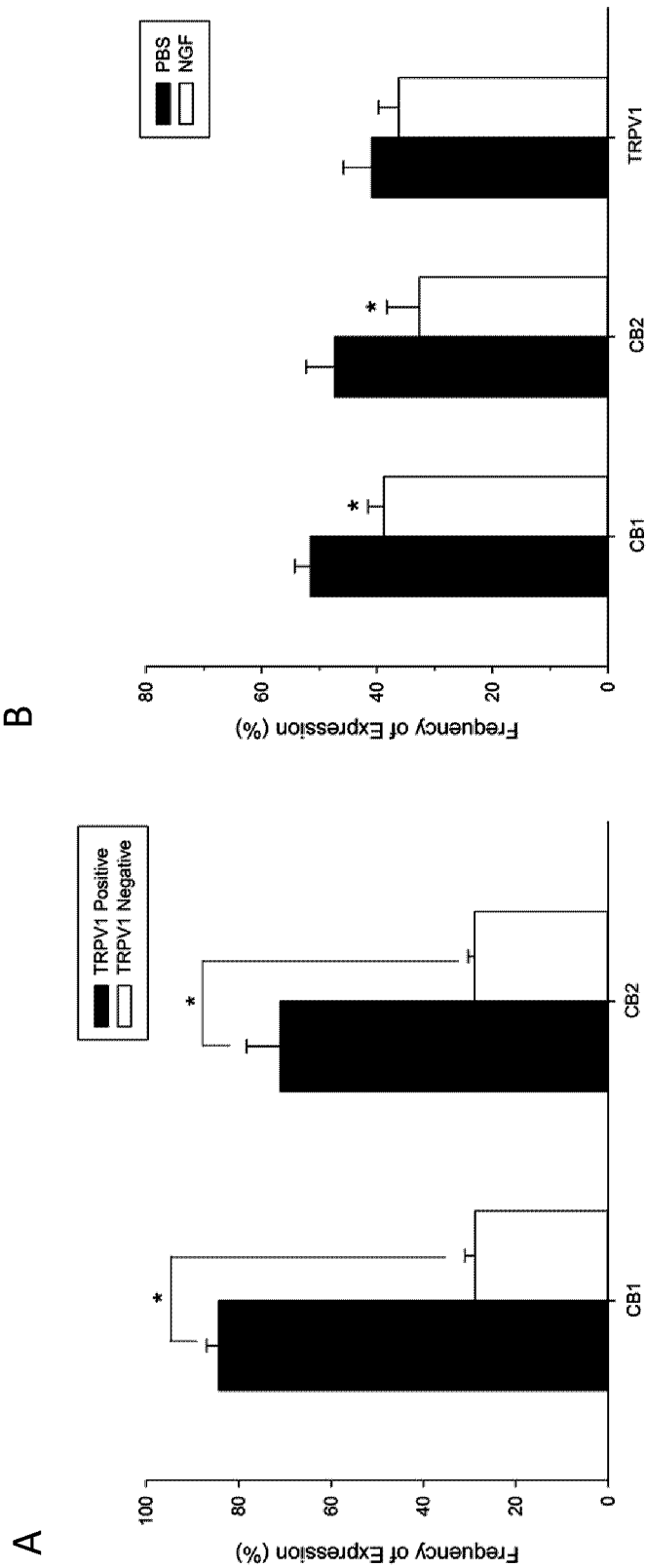
FIG. 4 is a bar graph. A illustrates the frequency of expression of CB1 and CB2 in TRPV1 positive and negative trigeminal ganglion neurons innervating the PBS-injected masseter muscles (n=5 rats). B: illustrates the frequency of expression of CB1, CB2 and TRPV1 in trigeminal ganglion neurons innervating the masseter muscle at 3 days after injection (n=5 rats). Asterisks denote a significant difference by paired Students t-tests ($p<0.05$). PBS—phosphate buffered saline. NGF nerve growth factor.

Expression of both cannabinoid receptors was observed in the trigeminal ganglion neurons that innervate the masseter muscle three days after injection of saline and NGF (FIG. 3A-D). Expression of CB1 and CB2 was greater in TRPV1-positive neurons (84.3±2.7% and 71.1±7.3%) than TRPV1-negative neurons (CB1: 28.8±2.2%, CB2: 28.9±1.4%) (FIG. 4A). Injection of NGF significantly reduced the expression of both receptors (FIG. 4B). On the saline-injected side, the frequency of expression of CB1 and CB2 was 52±3% and 47±5% in the masseter ganglion neurons, respectively. The frequency of expression of TRPV1 was 41±5%. On the NGF-injected side, the frequency of expression of CB1 and CB2 receptors was significantly reduced to 39±3% and 33±6%, respectively. No significant effect on TPRV1 expression was observed.

Figure 2:
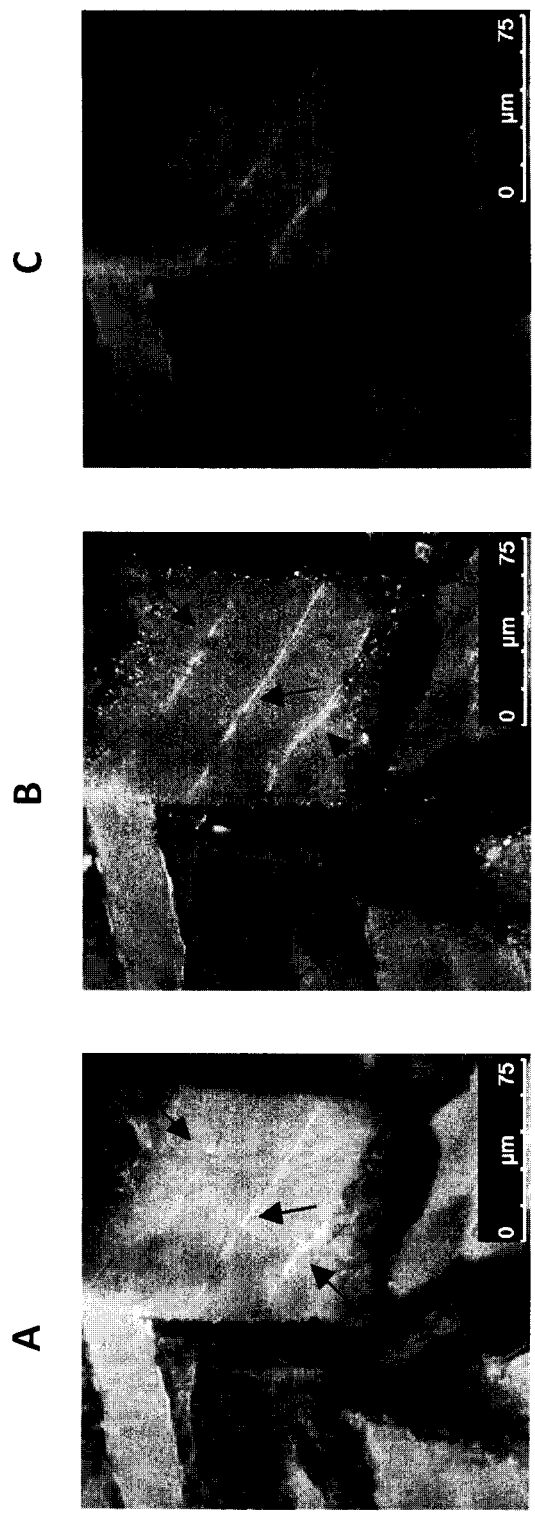
FIG. 2 is a series of photomicrographs showing co-expression of CB1 (B) and CB2 receptors (C) by nerve fibers that innervate the masseter muscle in a female rat. Nerve fibers were identified by immunopositivity to PGP9.5 (A).
Figure 3:
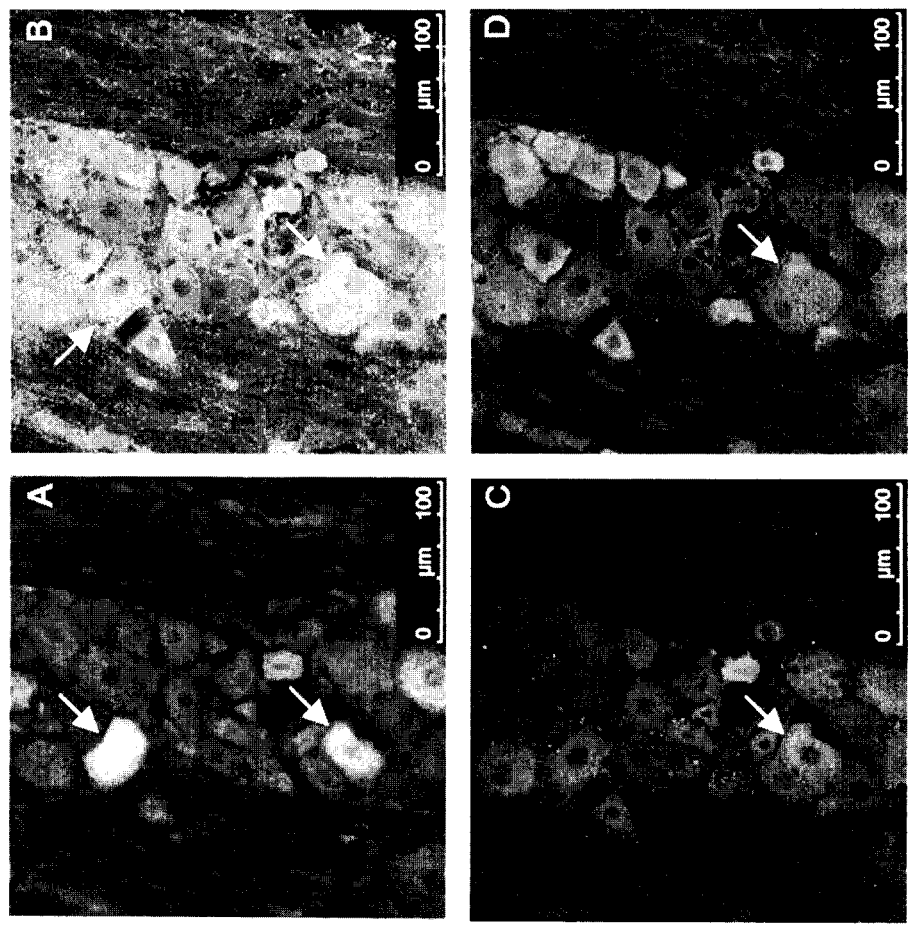
FIG. 3 is a series of photomicrographs showing co-expression of CB1, CB2 and TRPV1 by masseter ganglion neurons in a female rat. Masseter ganglion neurons were identified by intramuscular injection of fast blue (A; arrows) Immunopositivity for the CB1, CB2 and TRPV1 receptors is shown in B, C and D respectively.
Figure 5:
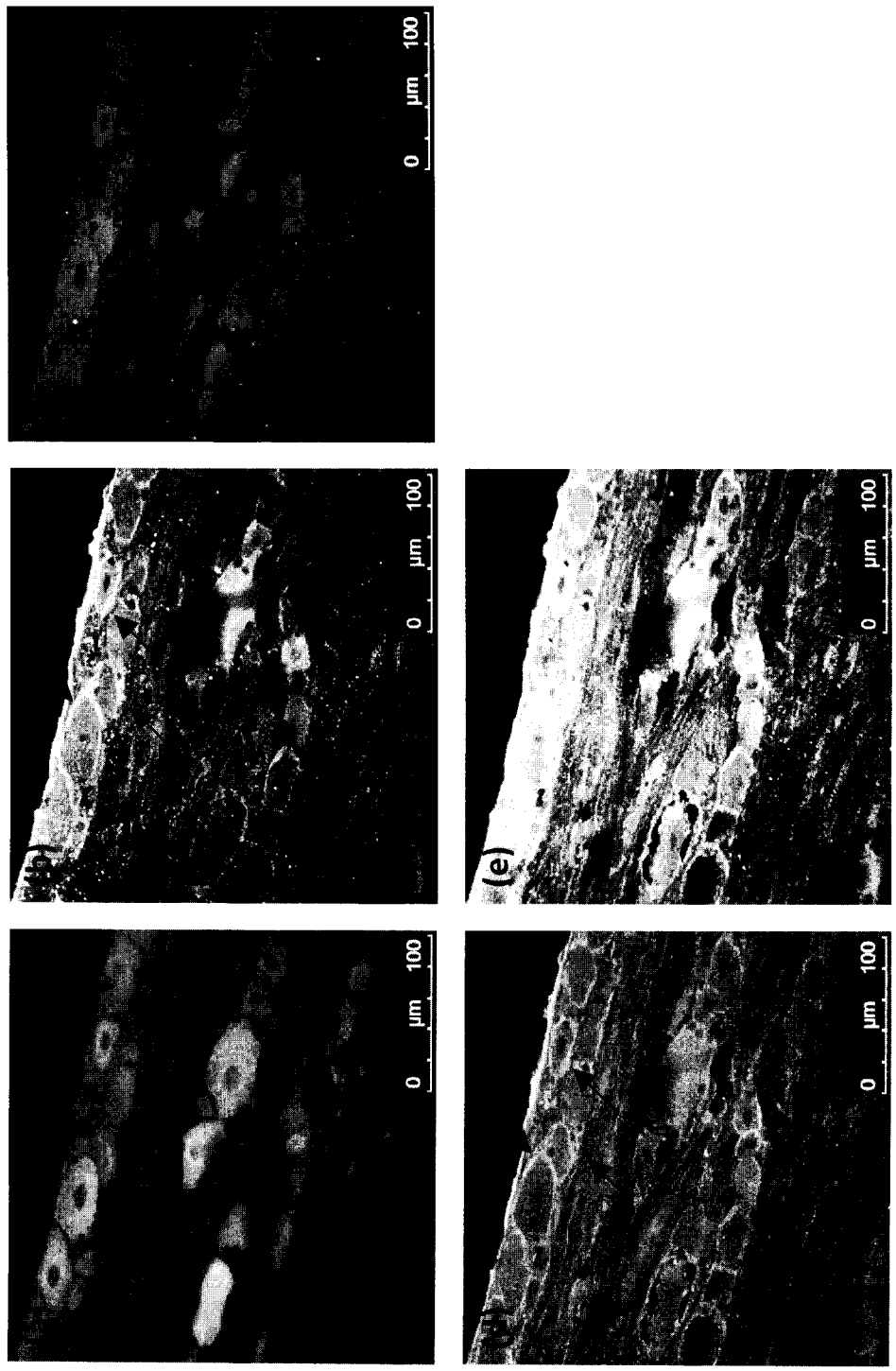
FIG. 5 is a photomicrograph showing expression of CB1 and glutamine synthetase, a marker for satellite glial cells, (SGC) by trigeminal ganglion neurons in a female rat. Expression of CB2 was not found in the SGCs. Masseter ganglion neurons were identified by intramuscular injection of fast blue (A) Immunopositivity for CB1, CB2 and glutamate synthetase (GS) is shown in (B), (C) and (D), respectively. The composite image is shown in (E). Arrows: A. Masseter ganglion neurons, B. SGCs, D. SGCs.

Expression of CB1 and CB2 were also found in the neuronal fibers in the masseter muscles, confirming their presence in the nerve endings of trigeminal ganglion neurons (FIG. 2). In the SGCs surrounding trigeminal ganglion neurons, expression of CB1, but not CB2 was observed (FIG. 5).

Effect of Intramuscular Injections of Cannabinoids on NGF-Induced Sensitization

Figure 6:
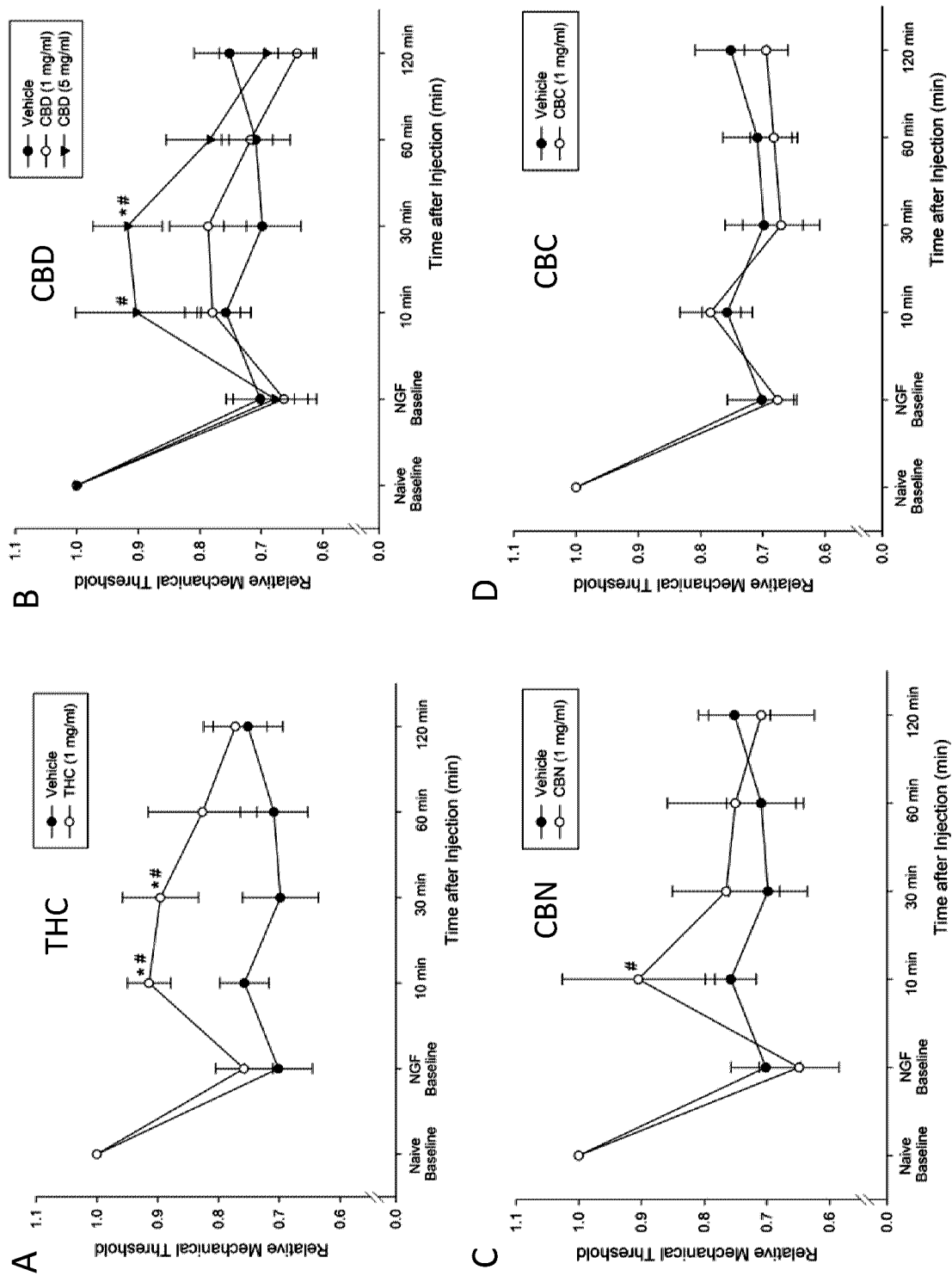
FIG. 6 illustrates the mean (±SE) mechanical withdrawal threshold of 6 female rats per treatment group following intramuscular injections of (A) THC (1 mg/ml), (B) CBD (1 and 5 mg/ml) and (C) CBN (1 mg/ml), (D) CBC (1 mg/ml) in behavioral experiments. Significant differences were observed for THC, CBD (5 mg/ml), and CBN compared to vehicle by 2-way repeated measures ANOVA. * indicates significant differences compared with the vehicle group and #indicates a significant difference compared to the NGF baseline within the treatment group (Holm Sidak multiple comparison test, $p<0.05$).
Figure 7:
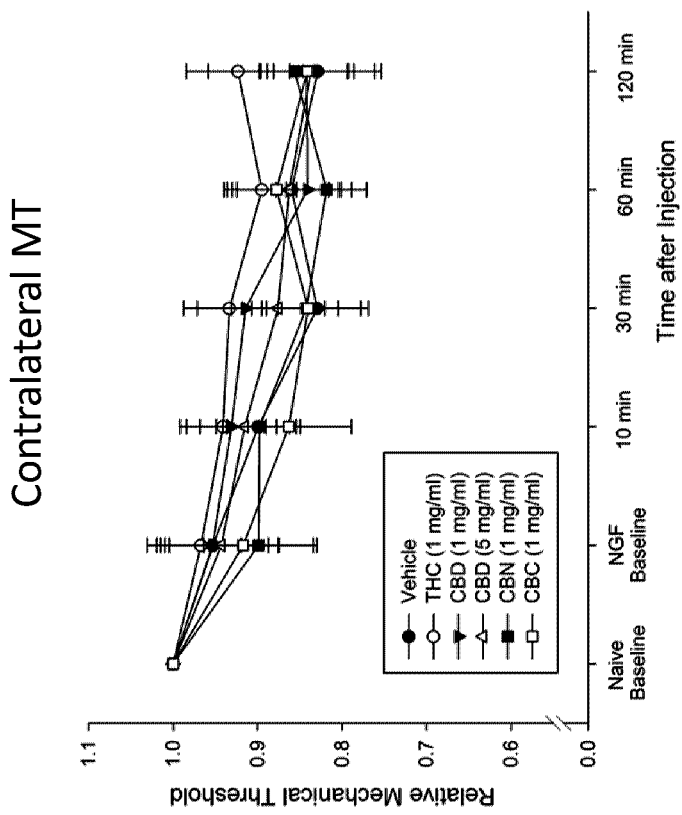
FIG. 7 illustrates relative mean mechanical threshold (MT) of contralateral masseter muscles after intramuscular cannabinoid injections in behavioral experiments (n=6/group). No significant differences between treatment groups were found by 2-way repeated measures ANOVA.

In the behavioral studies, intramuscular injection of NGF decreased masseter muscle MT at 3 days after injection by 31%, consistent with earlier studies (FIG. 6; 15). THC (1 mg/ml) significantly reversed NGF-induced sensitization at 10 and 30 min after injection (FIG. 6A). A similar concentration of CBD (1 mg/ml) had no effect on NGF-induced mechanical sensitization, but a much higher concentration of CBD (5 mg/ml) significantly reversed NGF-induced sensitization at 10 and 30 min after injection (FIG. 6B). A similar concentration of CBN (1 mg/ml) had a shorter lasting effect with a significant increase in MT at 10 min after injection compared to NGF baseline (FIG. 6C). No effect on MT was observed following intramuscular injection of CBC (1 mg/ml) injection (FIG. 6D). No effect of any injection was observed on the MT of contralateral masseter muscles for all treatment groups (FIG. 7). No impairment of motor functions was found in the inverted screen tests after intramuscular injections of THC, CBD, CBN and CBC (median score for all treatments was 0).

Figure 8:
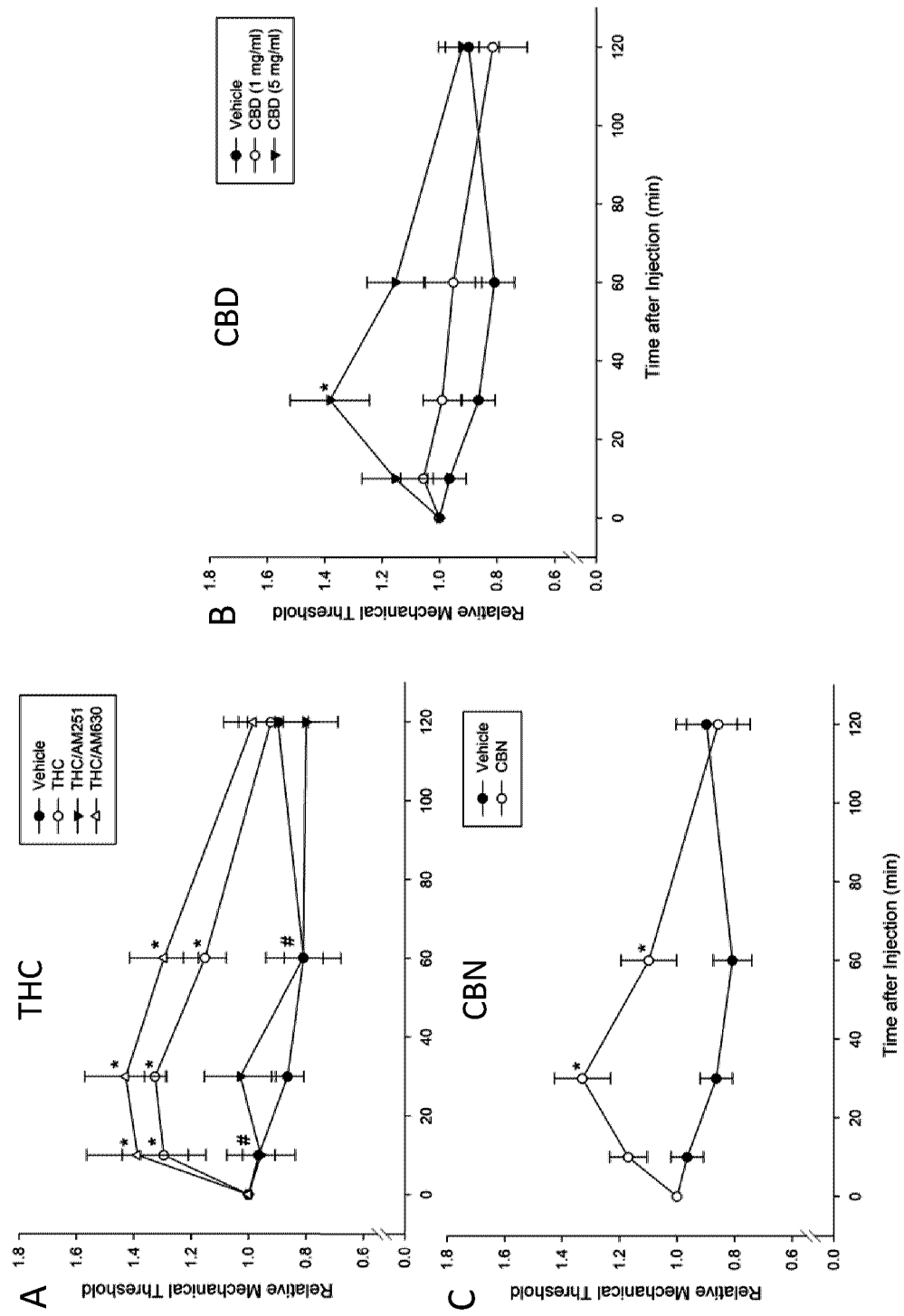
FIG. 8 illustrates the mean MT (±SE) of masseter muscle mechanoreceptors following intramuscular injections of (A) THC (1 mg/ml) and THC with AM251 or AM630 (1:0.5 and 1:1 mg/ml), (B) CBD (1 mg/ml) and (C) CBN (1 mg/ml) in electrophysiological experiments. Six mechanoreceptors are recorded for each treatment group. Significant differences were observed for THC, THC/AM630, CBD (5 mg/ml), and CBN compared to vehicle by 2-way repeated measures ANOVA. * indicates significant differences compared with the vehicle group and #indicates significant differences between THC and THC/AM251 treatment groups (Holm Sidak multiple comparison test, p<0.05). No significant difference was found when the vehicle and THC/AM251 treatment groups were compared.

Recordings from 42 masticatory muscle mechanoreceptors were undertaken. The median conduction velocity was 8.5 m/s ($25^{th}$ percentile: 4.9; $75^{th}$ percentile: 11.7) and the median mechanical threshold was 34.3 g ($25^{th}$ percentile: 17.7; $75^{th}$ percentile: 55.9). 74% was Aδ fibers (2-12 m/s), 21% was Aβ fibers (>12 m/s) and 5% was C fibers (<2 m/s). Intramuscular injection of THC (1 mg/ml) significantly increased the MT of mechanoreceptors at 10, 30 and 60 min after injection (FIG. 8A). CBD 5 mg/ml, but not 1 mg/ml, significantly increased MT, 30 min after injection (FIG. 8B). CBN 1 mg/ml significantly increased MT at 30 and 60 min after injection (FIG. 8C).

The results from the electrophysiology experiments for THC and CBD parallel the results from the behavioral experiments. As THC had the largest effect on afferent mechanical sensitivity, the effects of CB1 and CB2 selective antagonists were assessed for THC. Co-administration of THC and the CB1 antagonist AM251 attenuated the increase in MT mediated by THC alone and the combination was not significantly different from vehicle administration (FIG. 8A). Co-administration of THC and the CB2 antagonist AM630 was not different from THC alone (FIG. 8A). These results suggest intramuscular injection of THC increased MT of masseter muscle mechanoreceptors by acting through peripheral CB1 receptors.

Discussion

Many current drugs for the treatment of chronic pain are limited by intolerable central side effects and peripheral cannabinoid receptors have been proposed as potential targets with better efficacy and safety profile (12). In this study, expression of both CB1 and CB2 receptors was observed in trigeminal ganglion neurons innervating the masseter muscle, providing evidence that these receptors can be targets for craniofacial muscle pain. The reduction of CB1 and CB2 receptor expression after NGF injection suggests that this mechanism may contribute to NGF induced local myofacial sensitization. In the behavioral and electrophysiology experiments, intramuscular injection of cannabinoids reversed NGF-induced mechanical sensitization by temporarily increasing the mechanical thresholds of mechanoreceptors that innervate the masseter muscle. This effect was primarily mediated through the CB1 receptor. These results are consistent with earlier studies which found that local administration of THC reduced sensitization in muscle pain conditions (9, 10, 11, 12). Our results suggest that peripheral application of cannabinoids may be effective in the treatment of muscle pain disorders and may be a more desirable strategy than systemic administration due to their potential for central nervous system side effects.

CB1 receptors are primarily distributed throughout the central nervous system but have also been found on many peripheral tissues, while CB2 receptors are primarily expressed by cells with an immune function (31). However, a recent study also found their expression by human myofacial tissues (32). In the present study, CB1 and CB2 receptors were both observed in the trigeminal ganglion neurons innervating the masseter muscles as well as their nerve endings in the masseter muscles. Their expression was also higher in the TRPV1 expressing neurons than in the non TRPV1 expressing neurons. Since TRPV1 has been proposed as a nociceptor-specific transducer channel, these results suggested that CB1 and CB2 receptors may be preferentially expressed in putative nociceptors, highlighting their potential as peripheral targets of analgesia (33).

NGF is a neurotrophin essential for the growth and survival of sensory and sympathetic neurons (34, 35). In adults, it has also been found to play an important role during injury and nociception (35, 36). Previous studies showed that NGF may induce pain through increasing the expression of many excitatory receptors and substances associated with pain, including ion channels and receptors such as TRPV1, voltage-gated sodium channels, ASIC3 and P2X3 (36, 37, 38). NGF has also been found to increase the expression of the neuropeptides calcitonin gene related peptide (CGRP) and substance P (SP) as part of the phenotypic switch that is proposed to occur in sensory neurons following injury and inflammation (33, 39). We recently found that peripheral NMDA receptors may also be a part of the mechanism whereby NGF sensitizes muscle afferent fibers (16). In the present study, we found NGF decreased the expression of CB1 and CB2, on masseter ganglion neurons, suggesting that NGF may also induce sensitization, in part, by reducing endogenous peripheral inhibitory input. This result is in contrast to an earlier study where the expression of CB1 receptors increased after induction of CFA-induced inflammatory pain (40, 41). This may be understandable as NGF does not induce inflammation (27, 42) and may suggest that in chronic pain conditions where there is no obvious inflammation, pain may be mediated, in part, by a reduction of peripheral inhibitory input through the decrease in peripheral cannabinoid receptor expression.

Peripherally administered cannabinoids may compensate for the NGF-induced decrease in CB1 and CB2 expression to provide useful analgesia. However, one could argue that reduction of cannabinoid receptor expression may reduce the effectiveness of these compounds. However, approximately 40% of masseter ganglion neurons still expressed the CB1 receptor after NGF treatment. Conditional knockout of peripheral CB1 receptors in mice demonstrated that cannabinoid-induced analgesia is mediated primarily through peripheral CB1 receptors (43). This is also supported by our behavioral and electrophysiological results where cannabinoids with weaker binding affinity for the CB1 receptors, CBN ($\sim 1/10^{th}$) and CBD ($\sim 1/100^{th}$) had corresponding lesser effects than THC (44).

In the behavioral and electrophysiology experiments, THC, CBD and CBN were able to reverse the NGF-induced mechanical sensitization; THC through activation of CB1 receptors but not CB2 receptors. This was accompanied by no detectable contralateral effect on mechanical sensitivity or impaired motor functions in the inverted screen test, which indicates a local effect. These results suggest that although CB1 expression was reduced by NGF, activation of peripheral cannabinoid receptors was sufficient to provide effective local analgesia without systemic effects.

CB2 receptors may also be involved in the analgesic action of THC and other cannabinoids (11, 44). Indeed, CB2 receptors have been proposed as a target for neuroinflammation (46, 47). However, as NGF-induced mechanical sensitization is not associated with significant tissue inflammation, it might be expected that CB2 receptor activation would have a limited effect in this model of myofacial pain sensitivity (27).

In this study, non-THC cannabinoids CBD and CBN reversed NGF-induced sensitization in behavioral experiments by peripheral application. Although their effects were less robust when compared to THC, they could be advantageous since they have been found to have minimal psychotropic effects, which is a major limiting factor for THC (4, 5, 6). For CBD, significant effects on NGF-induced mechanical sensitization were only observed when the concentration was 5 times greater than that of THC. This difference is much less than would be expected based on the affinity of these two compounds for the CB1 receptor (44). It has also been proposed that CBD may act as an inverse agonist on CB1 receptors (44, 48). It is, therefore, possible that CBD may have effects on receptors other than CB1 when administered peripherally (49). For example, previous studies suggest CBD may have effects on GPR55 (50). GPR55 is an orphan G-protein coupled receptor which is predominantly expressed in the brain but is also found many tissues and organs (51). Lysophophatidylinositol has been proposed as endogenous ligand but it has also been found to bind to many cannabinoids (50, 51). Its physiological function is unclear but it has been proposed to play a role in regulation of energy intake, bone resorption, cancer and pain (51, 52).

*Cannabis* has been used to treat pain for centuries. Unfortunately, many pain sufferers do not derive benefit from its use or find its psychoactive effects too unpleasant to continue using it. Here we found that local administration of several cannabinoids could reverse mechanical sensitization in the masseter muscle through activation of the CB1 receptor without central side effects. Masticatory muscle pain is a common symptom of TMD and also fibromyalgia (19). Our results suggest that peripheral cannabinoid administration can be used for the treatment of chronic masticatory muscle pain.

REFERENCES

1. Maione S, Costa B, Di Marzo V. Endocannabinoids: a unique opportunity to develop analgesics. Pain 2013; 154: S87-93.
2. Robson P J. Therapeutic potential of cannabinoid medicines. Drug Testing and Analysis 2014; 6:24-30.
3. Ulugol A. The endocannabinoid system as a potential therapeutic target for pain modulation. Balkan Med J 2014; 31: 115-20.
4. Pertwee R G. Pharmacological actions of cannabinoids. Handb Exp Pharmacol 2005; 168:1-51.
5. Amar B Cannabinoids in medicine: A review of their therapeutic potential. J Ethnopharmacol 2006; 105:1-25.
6. Izzo A A, Borrelli F, Capasso R, Di Marzo V, Mechoulam R. Non-psychotropic plant cannabinoids: new therapeutic opportunities from an ancient herb. Trends Pharmacol Sci 2009; 30:515-27.
7. Price T J, Helesic G, Parghi D, Hargreaves K M, Flores C M. The neuronal distribution of cannabinoid receptor type 1 in the trigeminal ganglion of the rat. Neuroscience 2003; 120: 155-162.
8. Nadal X, La Porta C, Andreea Bura S, Maldonado R. Involvement of the opioid and cannabinoid systems in pain control: new insights from knockout studies. European Journal of Pharmacology 2013; 716: 142-157.
9. Johanek L M, Heitmiller D R, Turner M, Nader N, Hodges J, Simone D A. Cannabinoids attenuate capsaicin-evoked hyperalgesia through spinal and peripheral mechanisms. Pain 2001; 93:303-15.
10. Yu X H, Cao C Q, Martino G, Puma C, Morinville A, St-Onge S, Lessard E, Perkins M N, Laird J M. A peripherally restricted cannabinoid receptor agonist produces robust anti-nociceptive effects in rodent models of inflammatory and neuropathic pain. Pain 2010; 151:337-44.
11. Bagues A, Martin M I, Sanchez-Robles E M. Involvement of central and peripheral cannabinoid receptors on antinociceptive effect of tetrahyhrocannabinol in muscle pain. Eur J Pharmacol 2014; 745:69-75.
12. Romero-Sandoval E A, Asbill S, Paige C A, Byrd-Glover K. Peripherally Restricted Cannabinoids for the Treatment of Pain. Pharmaco Rahman A, Underwood M, Carnes D. Fibromyalgia. BMJ 2014; 348:g1224therapy 2015; 35:917-25.
13. Rahman A, Underwood M, Carnes D. Fibromyalgia. BMJ 2014; 348:g1224.
14. Clauw D J. Fibromyalgia: a clinical review. JAMA 2014; 311: 1547-1555.
15. Wong H, Kang I, Dong, X-D, Christidis N, Ernberg M, Svensson P, Cairns B E. NGF-induced mechanical sensitization of the masseter muscle is mediated through peripheral NMDA receptors. Neuroscience 2014; 269:232-244.

16. Wong H, Dong X-D, Cairns B E. Nerve growth factor alters the sensitivity of rat masseter muscle mechanoreceptors to NMDA receptor Cairns B E. The influence of gender and sex steroids on craniofacial nociception. Headache 2007; 47: 319-24. activation. J Neurophysiol 2014; 112: 2275-2282.

17. Cairns B E. The influence of gender and sex steroids on craniofacial nociception. Headache 2007; 47: 319-24.

18. Bush F M, Harkins S W, Harrington W G, Price D D. Analysis of gender effects on pain perception and symptom presentation in temporomandibular pain. Pain 1993; 53:73-80.

19. Cairns B E. Pathophysiology of TMD pain—basic mechanisms and their implications for pharmacotherapy. J Oral Rehabil 2010; 37:391-410.

20. Shaefer J R, Holland N, Whelan J S, Velly A M. Pain and temporomandibular disorders: a pharmaco-gender dilemma. Dent Clin North Am 2013; 57:233-62.

21. Mogil J S, Bailey AL Sex and gender differences in pain and analgesia. Progress in Brain Research 2010; 186: 141-157.

22. Sanford A E, Castillo E, Gannon R L. Cannabinoids and hamster circadian activity rhythms Brain Res 2008; 1222: 141-148.

23. Burston J J, Sagar D R, Shao P, Bai M, King E, Brailsford L, Turner J M, Hathway G J, Bennett A J, Walsh D A, Kendall D A, Lichtman A, Chapman V. Cannabinoid CB2 Receptors Regulate Central Sensitization and Pain Responses Associated with Osteoarthritis of the Knee Joint. PLoS One 2013; 8:e80440.

24. Svensson P, Cairns B E, Wang K, Arendt-Nielsen L. Injection of nerve growth factor into human masseter muscle evokes long-lasting mechanical allodynia and hyperalgesia. Pain 2003; 104:241-7.

25. Svensson P, Wang K, Arendt-Nielsen L, Cairns B E. Effects of NGF-induced muscle sensitization on proprioception and nociception. Exp Brain Res 2008; 189:1-10.

26. Svensson P, Wang M W, Dong X D, Kumar U, Cairns B E. Human nerve growth factor sensitizes masseter muscle nociceptors in female rats. Pain 2010; 148:473-80.

27. Mann M K, Dong X D, Svensson P, Cairns B E. Influence of intramuscular nerve growth factor injection on the response properties of rat masseter muscle afferent fibers. J Orofac Pain 2006; 20:325-36.

28. Coughenour L L, Mclean J R, Parker R B. A new device for the rapid measurement of impaired motor function in mice. Pharmacol Biochem Behav 1977; 6:351-3.

29. Maxwell D M, Brecht K M, Doctor B P, Wolfe A D. Comparison of antidote protection against soman by pyridostigmine, HI-6 and acetylcholinesterase. J Pharmacol Exp Ther 1993; 264:1085-9.

30. Cairns B E, Gambarota G, Svensson P, Arendt-Nielsen L, Berde C B. Glutamate-induced sensitization of rat masseter muscle fibers. Neuroscience 2002; 109(2):389-99.

31. Svizenská I, Dubový P, Sulcová A. Cannabinoid receptors 1 and 2 (CB1 and CB2), their distribution, ligands and functional involvement in nervous system structures—a short review. Pharmacol Biochem Behav. 2008; 90(4):501-11.

32. Fede C, Albertin G, Petrelli L, Sfriso M M, Biz C, De Caro R, Stecco C. Expression of the endocannabinoid receptors in human facial tissue. Eur J Histochem. 2016; 60(2): 2643.

33. Woolf C J, Ma Q. Nociceptors—noxious stimulus detectors. Neuron 2007; 55(3):353-64.

34. Bennett D L. Neurotrophic factors: important regulators of nociceptive function. Neuroscientist 2001; 7:13-7.

35. Pezet S, McMahon S B. Neurotrophins: mediators and modulators of pain. Annu Rev Neurosci 2006; 29:507-38.

36. Watson J J, Allen S J, Dawbarn D. Targeting nerve growth factor in pain: what is the therapeutic potential? BioDrugs 2008; 22:349-59.

37. McMahon S B, Bennett D L H. Trophic factors and pain. In: Wall P D, Melzack, R, editors. Textbook of pain. London: Churchill Livingstone, 1999.

38. Cheng J K, Ji R R. Intracellular signaling in primary sensory neurons and persistent pain. Neurochem Res 2008; 33-1970-78.

39. Latremoliere A, Woolf C J. Central sensitization: a generator of pain hypersensitivity by central neural plasticity. J Pain 2009; 10(9):895-926.

40. Amaya F, Shimosato G, Kawasaki Y, Hashimoto S, Tanaka Y, Ji R R, Tanaka M. Induction of CB1 cannabinoid receptor by inflammation in primary afferent neurons facilitates antihyperalgesic effect of peripheral CB1 agonist. Pain 2006; 124:175-83.

41. Niu K Y, Zhang Y, Ro J Y. Effects of gonadal hormones on the peripheral cannabinoid receptor 1 (CB1R) system under a myositis condition in rats. Pain 2012; 153: 2283-91.

42. Apfel S C, Arezzo J C, Brownlee M, Federoff H, Kessler J A. Nerve growth factor administration protects against experimental diabetic sensory neuropathy. Brain Res 1994; 634:7-12.

43. Agarwal N, Pacher P, Tegeder I, Amaya F, Constantin C E, Brenner G J, Rubino T, Michalski C W, Marsicano G, Monory K, Mackie K, Marian C, Batkai S, Parolaro D, Fischer M J, Reeh P, Kunos G, Kress M, Lutz B, Woolf C J, Kuner R. Cannabinoids mediate analgesia largely via peripheral type 1 cannabinoid receptors in nociceptors. Nat Neurosci 2007; 10:870-9.

44. Pertwee R G. The diverse CB1 and CB2 receptor pharmacology of three plant cannabinoids: delta9-tetrahydrocannabinol, cannabidiol and delta9-tetrahydrocannabivarin. Br J Pharmacol 2008; 153:199-215.

45. Quartilho A, Mata H P, Ibrahim M M, Vanderah T W, Porreca F, Makriyannis A, Malan T P Jr. Inhibition of inflammatory hyperalgesia by activation of peripheral CB2 cannabinoid receptors. Anesthesiology 2003; 99:955-60.

46. Adhikary S, Li H, Heller J, Skarica M, Zhang M, Ganea D, Tuma R F. Modulation of inflammatory responses by a cannabinoid-2-selective agonist after spinal cord injury. J Neurotrauma 2011; 28:2417-27.

47. Ashton J C, Glass M. The cannabinoid CB2 receptor as a target for inflammation-dependent neurodegeneration. Curr Neuropharmacol 2007; 5:73-80.

48. Thomas A, Baillie G L, Phillips A M, Razdan R K, Ross R A, Pertwee R G. Cannabidiol displays unexpectedly high potency as an antagonist of CB1 and CB2 receptor agonists in vitro. Br J Pharmacol 2007; 150:613-23.

49. Petrosino S, Ligresti A, Di Marzo V. Endocannabinoid chemical biology: a tool for the development of novel therapies. Curr Opin Chem Biol. 2009; 13(3):309-20.

50. Ryberg E, Larsson N, Sjögren S, Hjorth S, Hermansson N O, Leonova J, Elebring T, Nilsson K, Drmota T, Greasley P J. The orphan receptor GPR55 is a novel cannabinoid receptor. Br J Pharmacol 2007; 152:1092-101.

51. Shore D M, Reggio P H. The therapeutic potential of orphan GPCRs, GPR35 and GPR55. Front Pharmacol. 2015; 6:69.

52. Marichal-Cancino B A, Fajardo-Valdéz A, Ruiz-Contreras A E, Méndez-Díaz M, Prospéro-Garcia O. Advances in the Physiology of GPR55 in the Central Nervous System. Curr Neuropharmacol. 2016 Jul. 29.

53. Devesa I, Ferrer-Montiel A. Neurotrophins, endocannabinoids and thermo-transient receptor potential: a threesome in pain signaling. Eur J Neurosci 2014; 39:353-62.

54. Wang Z Y, McDowell T, Wang P, Alvarez R, Gomez T, Bjorling D E. Activation of CB1 inhibits NGF-induced sensitization of TRPV1 in adult mouse afferent neurons. Neuroscience 2014; 277:679-89.

55. Farquhar-Smith W P, Rice A S. A novel neuroimmune mechanism in cannabinoid-mediated attenuation of nerve growth factor-induced hyperalgesia. Anesthesiology 2003; 99:1391-401.

Figure 9:
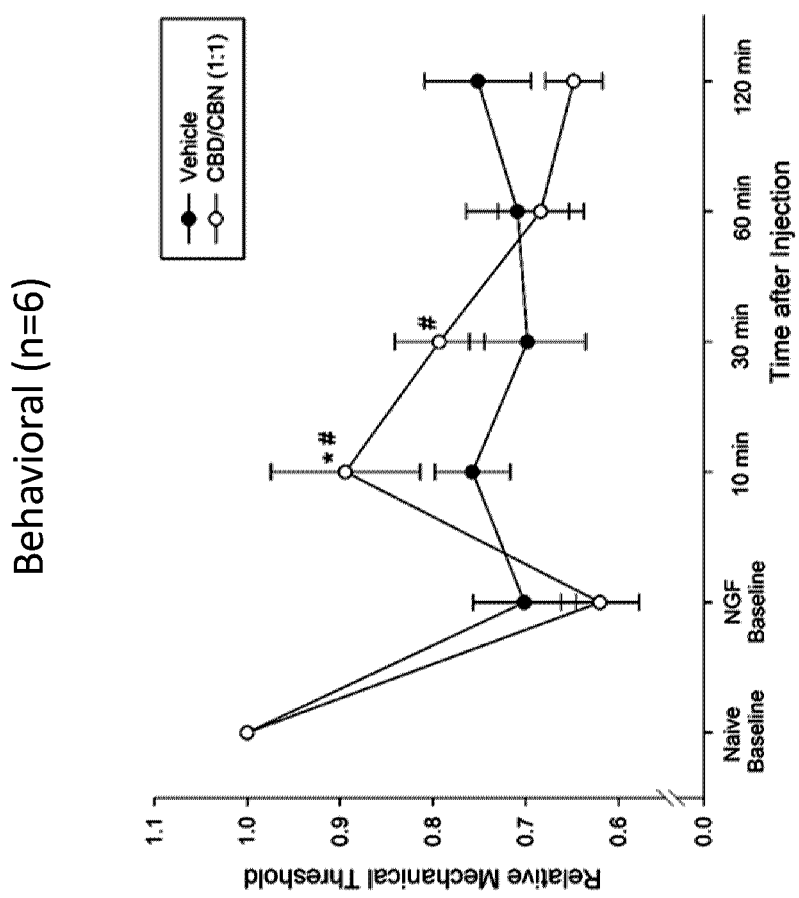
FIG. 9 illustrates mean MT of 6 female rats per treatment group following intramuscular injections of CBD/CBN (1:1 mg/ml) in behavioral experiments. Significant differences were observed by 2-way repeated measures ANOVA. The *s indicate significant differences compared with the vehicle group and #s indicate a significant difference compared to the NGF baseline within the treatment group (Holm Sidak multiple comparison test, p<0.05).
Figure 10:
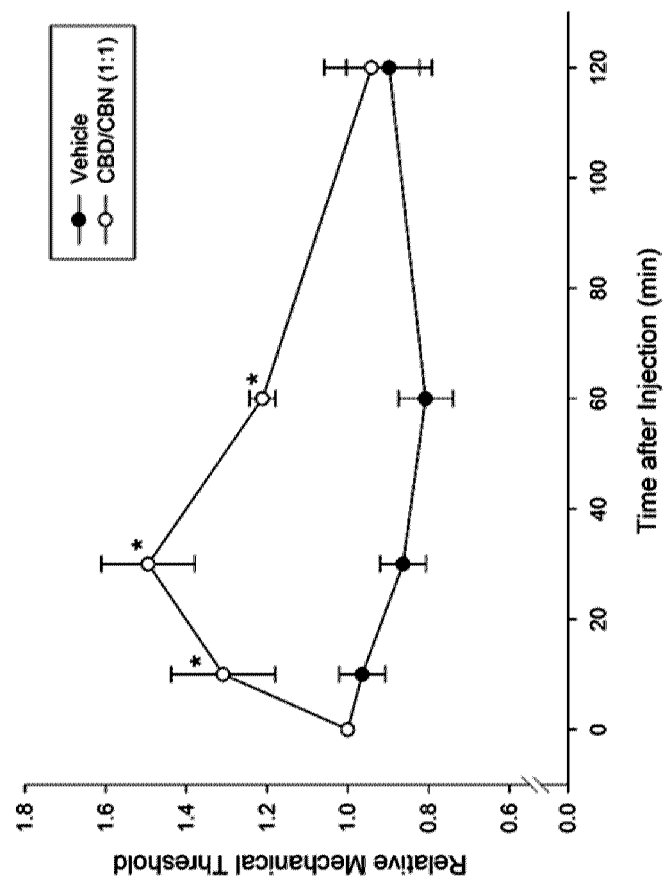
FIG. 10 illustrates the mean MT (±SE) of mechanoreceptors innervating the masseter muscle following intramuscular injections of CBD/CBN (1:1 mg/ml) in electrophysiological experiments. Significant differences were observed by 2-way repeated measures ANOVA. Asterisks indicate significant differences compared with the vehicle group (Holm Sidak multiple comparison test, p<0.05).
Figure 11:
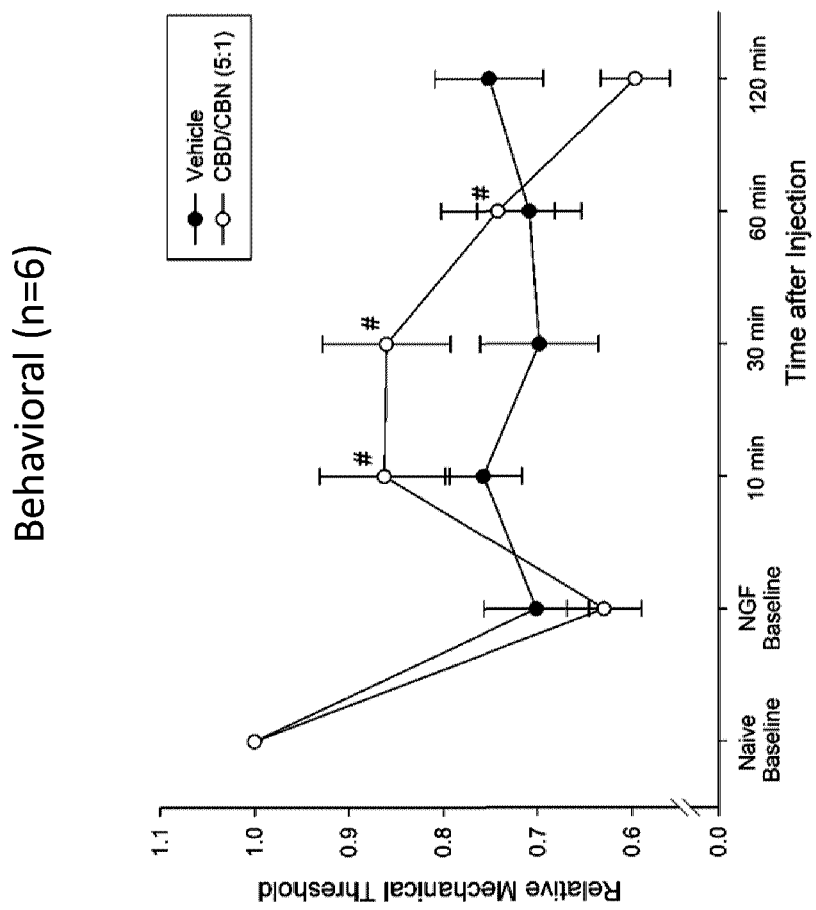
FIG. 11 illustrates relative mean MT of 6 female rats per treatment group following intramuscular injections of CBD/CBN (5:1 mg/ml) in behavioral experiments. No significant difference was observed between treatments by 2-way repeated measures ANOVA. Significant difference was observed for CBD/CBN at 10 30, and 60 minutes post injection. #s indicate a significant difference compared to the NGF baseline within the same treatment group (Holm Sidak multiple comparison test, p<0.05).
Figure 12:
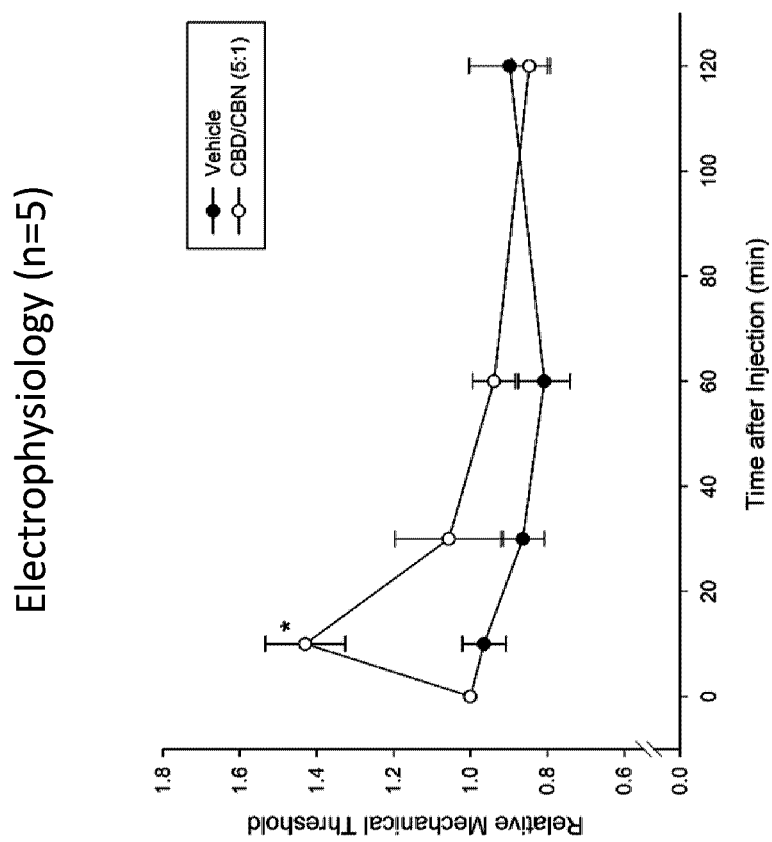
FIG. 12 illustrates mean MT (±SE) of mechanoreceptors innervating the masseter muscle following intramuscular injections of CBD/CBN (5:1 mg/ml) in electrophysiological experiments. Significant differences were observed by 2-way repeated measures ANOVA. * indicates significant differences compared with the vehicle group (Holm Sidak multiple comparison test, p<0.05).
Figure 13:
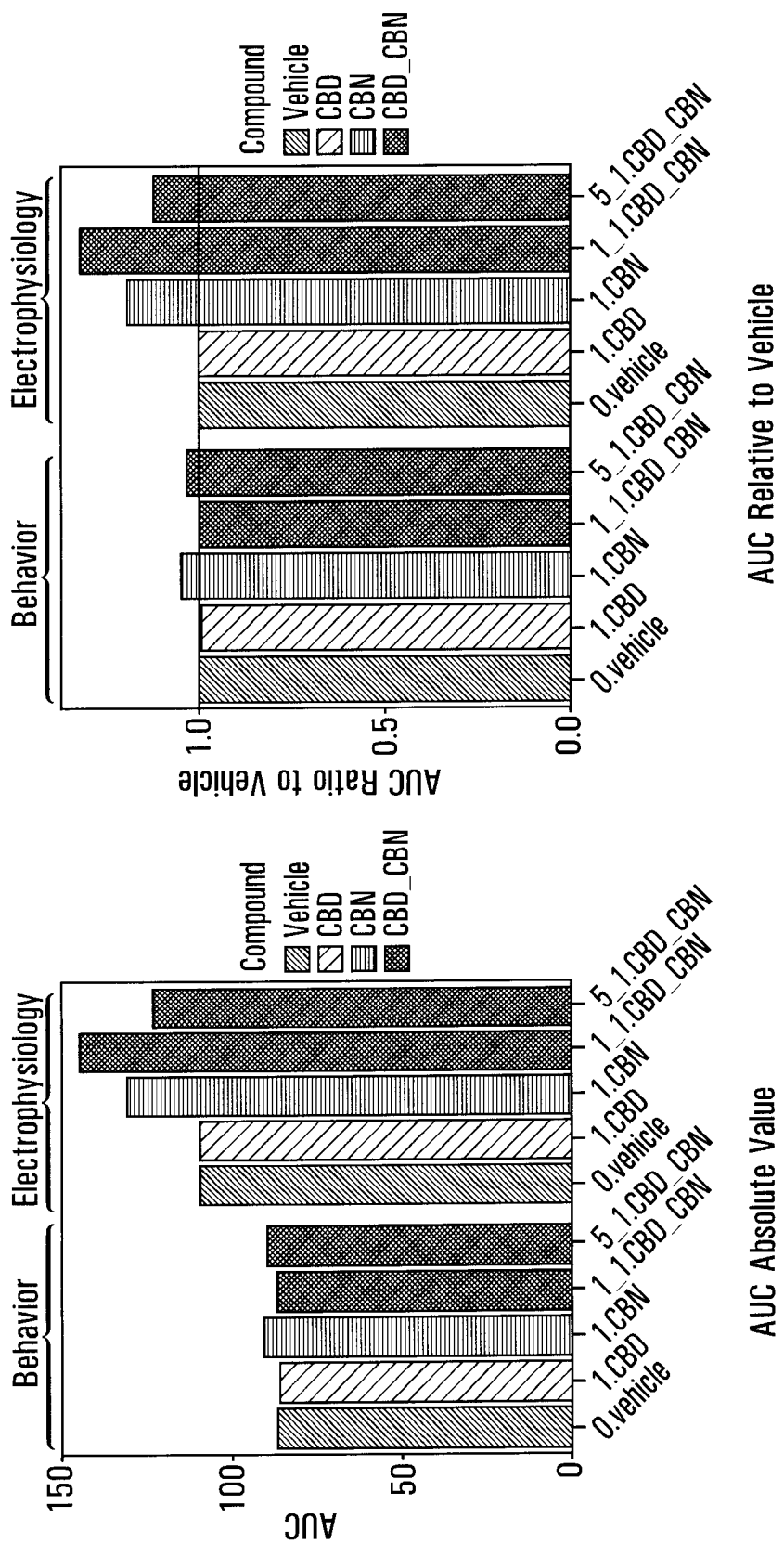
FIG. 13 illustrates area under curve (AUC) analysis of the data shown in FIGS. 9-12.

Example 2: Cannabinoid Mixtures Show Increased Efficacy in Decreasing Pain Sensitization Cannabinoid mixtures were studied to investigate their effect on mechanical thresholds of peripheral pain fibers by behavioral (FIG. 9 and FIG. 11) and electrophysiological observations (FIG. 10 and FIG. 12). The behavioral experiments were performed using essentially identical methods and compositions in Example 1 to produce FIG. 6, except where indicated herein. The electrophysiological experiments were performed using essentially identical methods and compositions in Example 1 to produce FIG. 8, except where indicated herein. Intramuscular injection of a 1:1 mixture of $\Delta^2$-cannabidiol to cannabinol at 1 mg/mL, a significant difference between vehicle and mixture was observed in both the behavioral (FIG. 9) and electrophysiological (FIG. 10) tests. Intramuscular injection of a 5 mg/mL to 1 mg/L ratio of $\Delta^2$-cannabidiol to cannabinol resulted in a greater increase in relative mechanical threshold as observed by behavioral (FIG. 11) and electrophysiological (FIG. 12) tests.

The data were also subjected to area under the curve (AUC) analysis. AUC analysis of the electrophysiological data revealed that administration of CBN, CBD:CBN at 1:1, and CBD:CBN at 5:1 resulted in a reduction in pain response as compared to the other indicated treatments, with CBD:CBN 1:1 exhibiting superior in vivo efficacy.

Example 3: Topical Delivery Shows Reduced Neuropathic Pain

Figure 14:
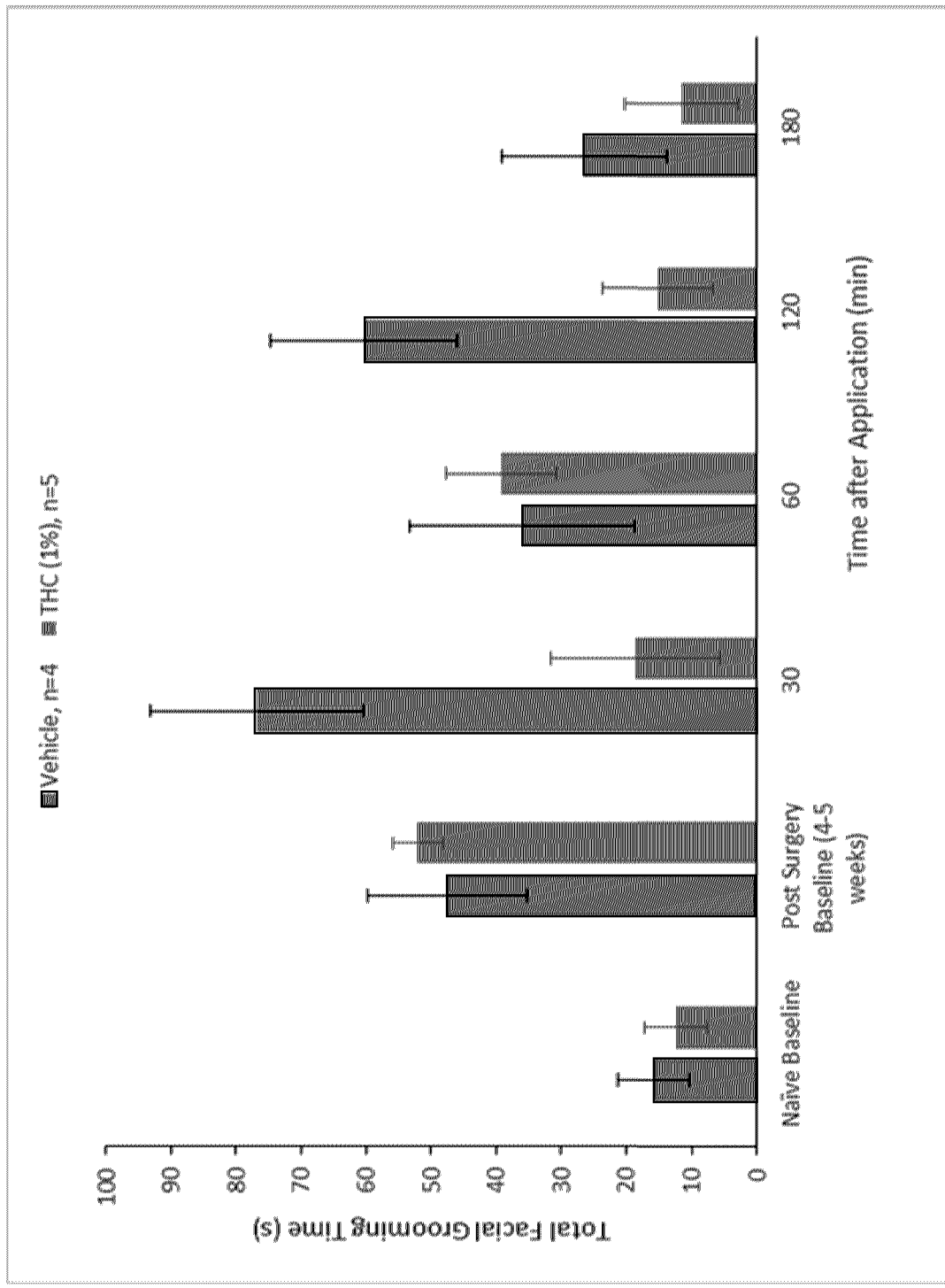
FIG. 14 illustrates the effect of topical THC (1%) in a mental nerve ligation model. Neuropathic pain behavior was measured by observing total facial grooming in naïve and post-surgical mice after application of vehicle or THC.
Figure 15:
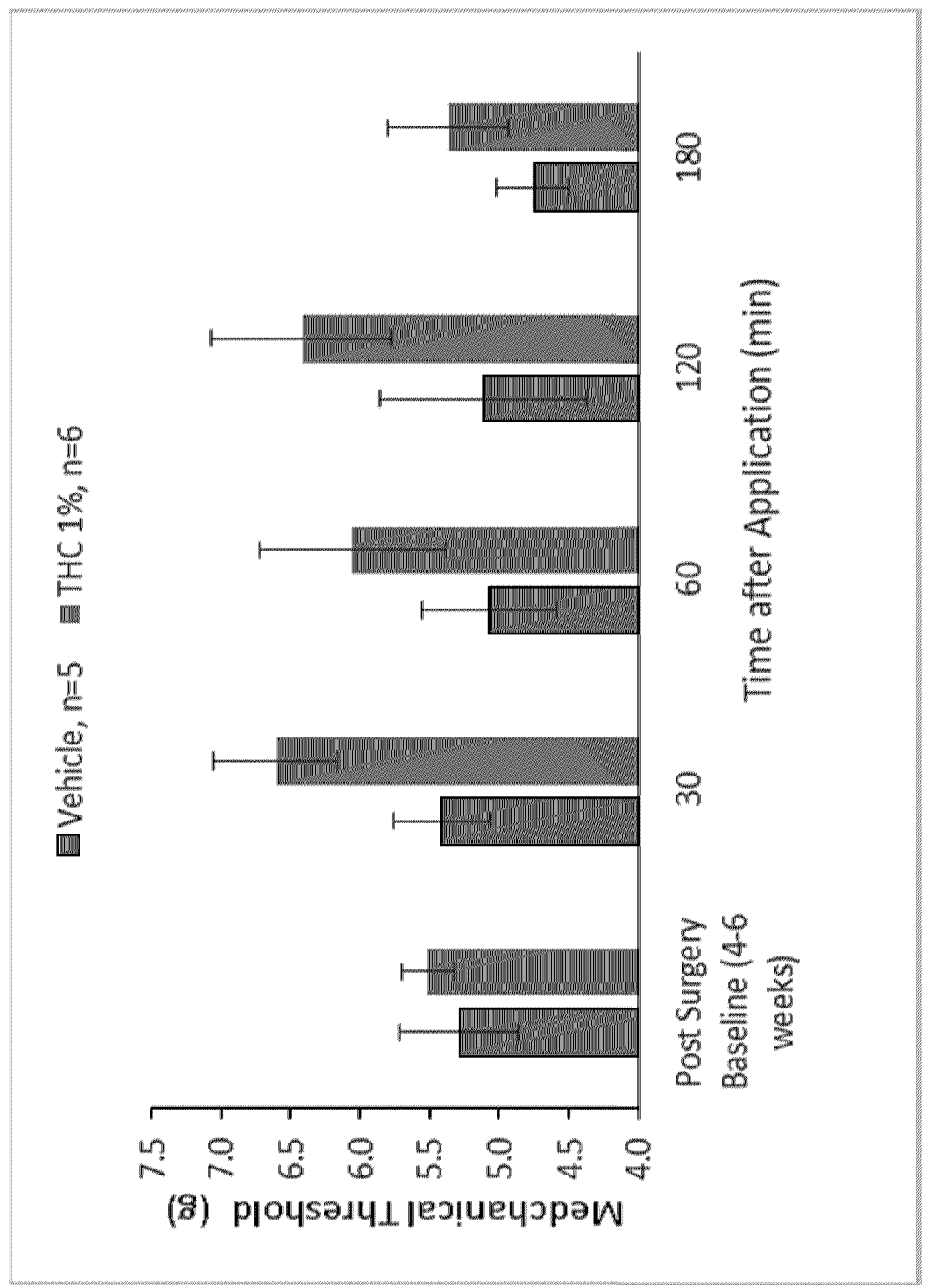
FIG. 15 illustrates the effect of topical THC (1%) in a mental nerve ligation model. Neuropathic pain behavior was measured by observing mechanical threshold response in naïve and post-surgical mice after application of vehicle or THC.

In proof-of-concept study, topical THC (1% in a PLO-gel cream base) reduced neuropathic pain behavior (facial grooming, FIG. 14) and reversed mechanical allodynia in the lower lip skin in the mental nerve ligation model (FIG. 15).

Example 4: Topical Formulations Show Delivery to Basal Cell Layer of Skin

To deliver the topical therapy the present inventors developed a Labrasol, Plo-gel formulation (Poloxomer 407, Lecithin, and isopropyl palmitate, 0.6% cannabinoid). The formulation was applied to the center part of the circle and is rubbed to the porcine skin using a scalpel. The sample was mounted to the top of Franz diffusion cell with the outer layer of the skin facing upward. the receptor medium of Franz cell was filled with phosphate buffer. Then the cap of the cell was mounted and clamped. This construct was placed inside the incubator/shaker for 18 hours at 32° C.

A skin penetration profile of cannabinoid compounds showed that after 18 h most of the cannabinoid compounds were located at the basal cell layers of skin.

Figure 16:
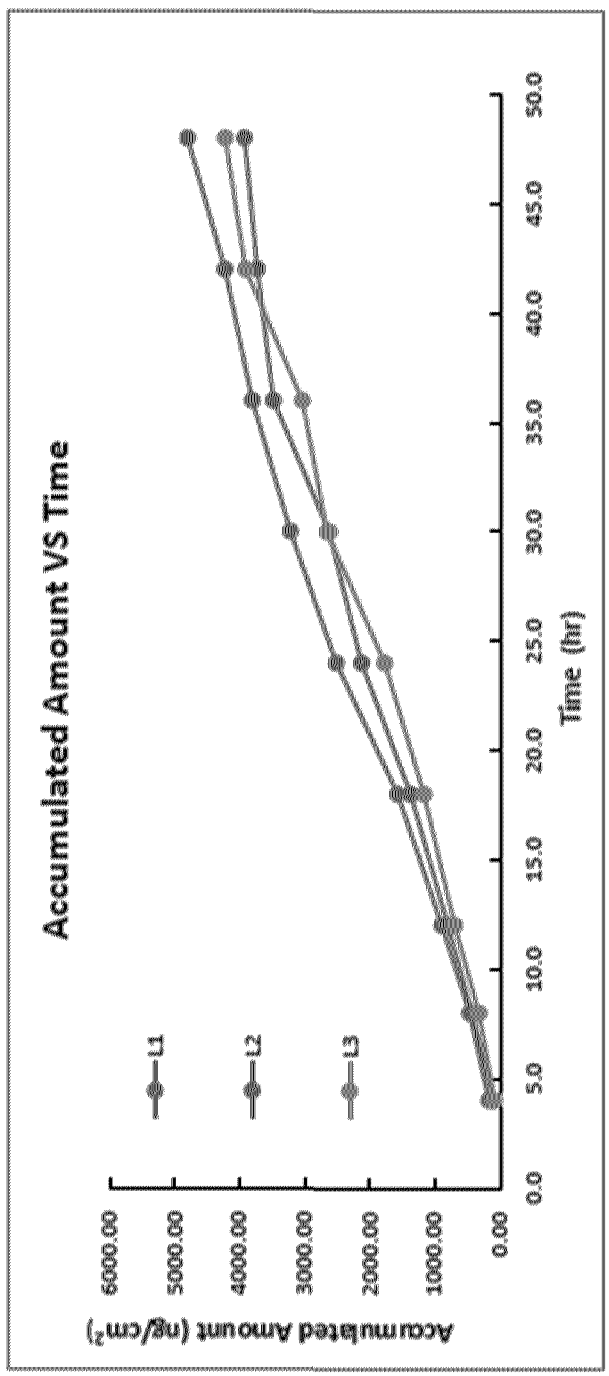
FIG. 16 illustrates rapid and sustained permeation of CBD through human cadaver skin when topically applied as a 10:1 mixture of CBD:CBN in pharmaceutical formulation L as described in Table 1. The cannabinoid mixture in the formulation is applied at a dose of 5 mg/cm$^2$.
Figure 17:
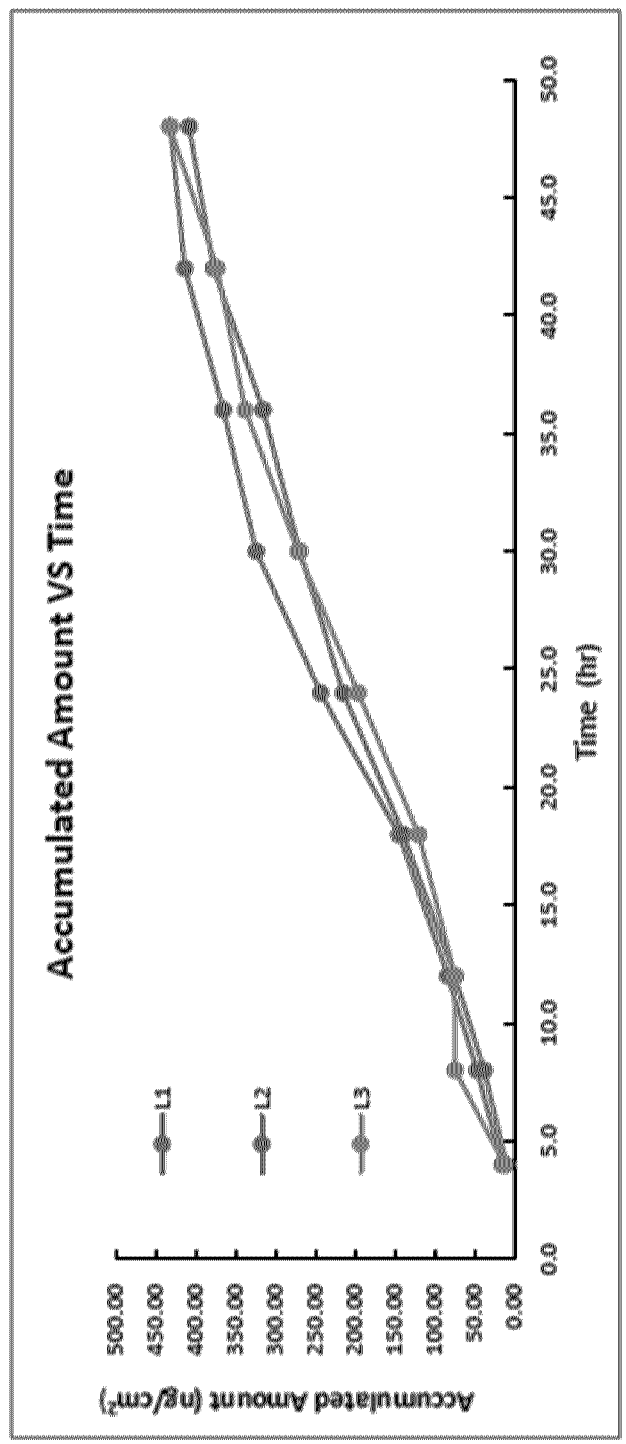
FIG. 17 illustrates rapid and sustained permeation of CBN through human cadaver skin when topically applied as a 10:1 mixture of CBD:CBN in pharmaceutical formulation L as described in Table 1. The cannabinoid mixture in the formulation is applied at a dose of 5 mg/cm$^2$.

Example 5: Topical Formulations Show Rapid and Sustained Delivery Through Basal Cell Layer of Human Skin Formulations A-P were prepared according to the proportions described in Table 1. Briefly, the cannabinoids were dissolved in a lipophilic phase with gentle heat (~40° C.) and stirring and then cooled to room temperature. The hydrophilic phase was prepared by mixing poloxamer and water at a refrigerated temperature (~2-8° C.), which facilitated maintenance of a liquid state. The lipophilic phase and hydrophilic phase were then combined with vigorous stirring. Formulations A-L were tested for delivery through the stratum corneum by Franz diffusion cell assay as described above using human cadaver skin. Cannabinoid in the receiver solution was detected using LC/MS. The presence of detectable quantities of cannabinoid in the receiver solution indicated permeation. FIGS. 16-17. Formulations M-P are also tested using the Franz diffusion cell assay.

TABLE 1

| Formulation | Lipophilic Phase | Hydrophilic Phase | Result |
|---|---|---|---|
| A | 20% 1:1 lecithin:Isopropyl palmitate | 80% (containing 30% poloxamer) | Stiff gel; dries skin No permeation |
| B | 35% 1:1 lecithin:Isopropyl palmitate | 65% (containing 30% poloxamer) | Creamier gel; doesn't dry skin No permeation |
| D | 30% 1:1 lecithin:isopropyl myristate | 70% (containing 20% poloxamer) | No permeation |
| E | 35% 1:3 lecithin:isopropyl myristate | 65% (containing 20% poloxamer) | No permeation |
| F | 35% isopropyl myristate | 65% (containing 20% poloxamer) | Only CBN in receiving chamber Gel very thin, unstable |
| G | 35% 1:3 lecithin:isopropyl palmitate | 65% (containing 20% poloxamer) | Both drugs detected in receiving chamber Both drugs in skin |
| K | 25% 1:3 lecithin:isopropyl palmitate And 10% Transcutol | 65% (containing 20% poloxamer) | Preliminary data shows both drugs in receiver solution and consistent flux |
| L | 25% 1:3 lecithin:isopropyl palmitate And 10% Labrasol | 65% (containing 20% poloxamer) | Preliminary data shows both drugs in receiver solution and consistent flux FIGS. 16-17 |
| M | 35% 1:6 lecithin:isopropyl palmitate | 65% (containing 20% poloxamer) | |
| N | 25% 1:3: lecithin isopropyl palmitate And 10% Transcutol | 65% (containing 20% poloxamer) | |
| P | 25% 1:3: lecithin isopropyl palmitate And 10% Labrasol | 65% (containing 20% poloxamer) | |

The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed.

Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein.

In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. The disclosures of all articles and references, including patent publications, are incorporated herein by reference.

What is claimed is:

1. A pharmaceutical composition for treating pain, the pharmaceutical composition comprising:
   a. a therapeutically effective quantity of a mixture of one or more cannabidiols and cannabinol in a ratio of 5:1 μM,
      wherein the therapeutically effective quantity of the mixture is an amount that induces no or substantially no psychoactive effect when administered by topical administration and is sufficient to reduce or reverse pain and/or central sensitization; and
   b. at least one pharmaceutically acceptable carrier for topical administration of the pharmaceutical composition, wherein the pharmaceutical carrier comprises caprylocaproyl polyoxy-8 glycerides, poloxamer 407, lecithin, and isopropyl palmitate, and wherein the pharmaceutical composition is a topical formulation.

2. The pharmaceutical composition of claim 1, wherein said therapeutically effective quantity is an amount sufficient to increase a mechanical threshold in peripheral nerve fibers of the area treated by topical administration, reduce or eliminate hyperalgesia in the area treated by topical administration, or reduce or eliminate allodynia in the area treated by topical administration.

3. The pharmaceutical composition of claim 1, wherein the one or more cannabidiols are selected from the group consisting of: (i) $\Delta^5$-cannabidiol (2-(6-isopropenyl-3-methyl-5-cyclohexen-1-yl)-5-pentyl-1,3-benzenediol); (ii) $\Delta^4$-cannabidiol (2-(6-isopropenyl-3-methyl-4-cyclohexen-1-yl)-5-pentyl-1,3-benzenediol); (iii) $\Delta^3$-cannabidiol (2-(6-isopropenyl-3-methyl-3-cyclohexen-1-yl)-5-pentyl-1,3-benzenediol); (iv) $\Delta^{3,7}$-cannabidiol (2-(6-isopropenyl-3-methylenecyclohex-1-yl)-5-pentyl-1,3-benzenediol); (v) $\Delta^2$-cannabidiol(2-(6-isopropenyl-3-methyl-2-cyclohexen-1-yl)-5-pentyl-1,3benzenediol); and (vi) $\Delta^1$-cannabidiol (2-(6-isopropenyl-3-methyl-1-cyclohexen-1-yl)-5-pentyl-1,3benzenediol); and (vii) $\Delta^6$-cannabidiol (2-(6-isopropenyl-3-methyl-6-cyclohexen-1-yl)-5-pentyl-1,3-benzenediol).

4. The pharmaceutical composition of claim 1, comprising an additional therapeutically active agent selected from the group consisting of a topical anti-inflammatory agent, and a topical steroid, or further comprising a therapeutically effective quantity of a terpenoid, wherein the terpenoid is selected from the group consisting of borneol, carvophyllene, 1,8-cineol, p-cymene, fenchone, α-humulene, kaempferol, limonene, linoleic acid, α-linolenic acid, luteolin, β-myrcene, oleic acid, orientin, α-pinene, phytol, quercetin, selinene, sitosterol, terpinenol-4, N-trans-caffeoyltyramine, N-trans-coumaroyltyramine, N-trans-ferruloyltyramine, and vitexin.

5. The pharmaceutical composition of claim 4, wherein the terpenoid is borneol, 3-myrcene, or a combination of borneol and 3-myrcene.

6. A method for treating pain in a subject in need thereof, the method comprising topical application of a pharmaceutical composition according to claim 1 to a mammalian subject in need thereof.

7. The method of claim 6, wherein said pain is muscle pain.

* * * * *